US012759985B2

(12) United States Patent
Kysil et al.

(10) Patent No.: US 12,759,985 B2
(45) Date of Patent: Oct. 13, 2026

(54) COMPOUNDS HAVING 5-(2-FLUORO-6-HYDROXYPHENYL)-1,2,5-THIADIAZOLIDIN-3-ONE 1,1-DIOXIDE AS INHIBITORS OF PROTEIN KINASE PHOSPHATASE ENZYMES

(71) Applicant: Ness Therapeutics, Inc., San Diego, CA (US)

(72) Inventors: Volodymyr Kysil, San Diego, CA (US); Vladislav Zenonovich Parchinsky, Moscow (RU); Alexei Pushechnikov, San Diego, CA (US); Alexandre Vasilievich Ivachtchenko, Hallandale Beach, FL (US); Nikolay Savchuk, San Diego, CA (US)

(73) Assignee: Mondego Bio, LDA, Cantanhede (PT)

( * ) Notice: Subject to any disclaimer, the term of this patent is extended or adjusted under 35 U.S.C. 154(b) by 379 days.

(21) Appl. No.: 18/534,527

(22) Filed: Dec. 8, 2023

(65) Prior Publication Data

US 2024/0262801 A1 Aug. 8, 2024

(51) Int. Cl.

| | |
|---|---|
| ***C07D 285/10*** | (2006.01) |
| ***A61K 31/433*** | (2006.01) |
| ***A61K 31/4439*** | (2006.01) |
| ***A61K 31/454*** | (2006.01) |
| ***A61K 31/4709*** | (2006.01) |
| ***A61K 31/4725*** | (2006.01) |
| ***A61K 31/496*** | (2006.01) |
| ***A61K 31/5377*** | (2006.01) |
| ***C07D 417/12*** | (2006.01) |

(52) U.S. Cl.

CPC .......... *C07D 285/10* (2013.01); *A61K 31/433* (2013.01); *A61K 31/4439* (2013.01); *A61K 31/454* (2013.01); *A61K 31/4709* (2013.01); *A61K 31/4725* (2013.01); *A61K 31/496* (2013.01); *A61K 31/5377* (2013.01); *C07D 417/12* (2013.01)

(58) Field of Classification Search

None

See application file for complete search history.

(56) References Cited

U.S. PATENT DOCUMENTS

| | | | |
|---|---|---|---|
| 2010/0305036 A1 | 12/2010 | Barnes et al. | |
| 2020/0299246 A1 | 9/2020 | Halvorsen et al. | |

FOREIGN PATENT DOCUMENTS

| | | | |
|---|---|---|---|
| WO | WO-2007067612 A1 * | 6/2007 | ................ A61P 3/06 |
| WO | WO-2020186199 A1 * | 9/2020 | ................ A61P 3/04 |
| WO | WO-2022056281 A1 * | 3/2022 | ........... C07D 417/14 |

* cited by examiner

*Primary Examiner* — Jeffrey S Lundgren
*Assistant Examiner* — Anthony Joseph Seitz
(74) *Attorney, Agent, or Firm* — Sergey Alyabyev

(57) ABSTRACT

The present invention is generally directed to inhibitors of protein tyrosine phosphatase enzymes useful in the treatment of diseases and disorders modulated by said enzymes and having the Formula (I):

(I)

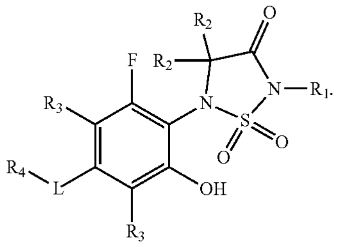

15 Claims, No Drawings

Specification includes a Sequence Listing.

SEQUENCE LISTING

```
Sequence total quantity: 1
SEQ ID NO: 1            moltype = AA  length = 641
FEATURE                 Location/Qualifiers
source                  1..641
                        mol_type = protein
                        organism = synthetic construct
SEQUENCE: 1
MSPILGYWKI KGLVQPTRLL LEYLEEKYEE HLYERDEGDK WRNKKFELGL EFPNLPYYID  60
GDVKLTQSMA IIRYIADKHN MLGGCPKERA EISMLEGAVL DIRYGVSRIA YSKDFETLKV  120
DFLSKLPEML KMFEDRLCHK TYLNGDHVTH PDFMLYDALD VVLYMDPMCL DAFPKLVCFK  180
KRIEAIPQID KYLKSSKYIA WPLQGWQATF GGGDHPPKSD LVPRGSMPTT IEREFEELDT  240
QRRWQPLYLE IRNESHDYPH RVAKFPENRN RNRYRDVSPY DHSRVKLQNA ENDYINASLV  300
DIEEAQRSYI LTQGPLPNTC CHFWLMVWQQ KTKAVVMLNR IVEKESVKCA QYWPTDDQEM  360
LFKETGFSVK LLSEDVKSYY TVHLLQLENI NSGETRTISH FHYTTWPDFG VPESPASFLN  420
FLFKVRESGS LNPDHGPAVI HCSAGIGRSG TFSLVDTCLV LMEKGDDINI KQVLLNMRKY  480
RMGLIQTPDQ LRFSYMAIIE GAKCIKGDSS IQKRWKELSK EDLSPAFDHS PNKIMTEKYN  540
GNRIGLEEEK LTGDRCTGLS SKMQDTMEEN SESALRKRIR EDRKATTAQK VQQMKQRLNE  600
NERKRKRWLY WQPILTKMGF MSVILVGAFV GWTLFFQQNA L                    641
```

COMPOUNDS HAVING 5-(2-FLUORO-6-HYDROXYPHENYL)-1,2,5-THIADIAZOLIDIN-3-ONE 1,1-DIOXIDE AS INHIBITORS OF PROTEIN KINASE PHOSPHATASE ENZYMES

CROSS-REFERENCE TO RELATED APPLICATIONS

This application is a national stage of International Patent Application Ser. No. PCT/US2022/032572 filed Jun. 7, 2022 and entitled "Compounds Having 5-(2-fluor-6-hydroxyphenyl)-1,2,5-thiadiazolidin-3-one 1,1dioxide as Inhibitors of Protein Tyrosine Phosphatase Enzymes", which claims priority to and the benefit of U.S. Provisional Patent Application Ser. No. 63/209,274 filed Jun. 10, 2021 and entitled "Compounds Having 5-(2-fluoro-6-hydroxyphenyl)-1,2,5-thiadiazolidin-3-one 1,1-dioxide as Inhibitors of Protein Tyrosine Phosphatase Enzymes", the disclosures of which are incorporated herein by reference in their entirety for all purposes.

FIELD OF INVENTION

The present invention is directed to inhibitors of protein tyrosine phosphatase enzymes, such as protein tyrosine phosphatase non-receptor type 1 (PTPN1) and protein tyrosine phosphatase non-receptor type 2 (PTPN2). The inhibitors described herein can be useful in the treatment of diseases or disorders associated with protein tyrosine phosphatase enzymes, such as cancer and metabolic diseases. In particular, the invention is concerned with compounds and pharmaceutical compositions inhibiting protein tyrosine phosphatase enzymes, methods of treating diseases or disorders associated with protein tyrosine phosphatase enzymes, and methods of synthesizing these compounds.

INCORPORATION BY REFERENCE OF SEQUENCE LISTING

The contents of the file named "Ness 21.0001 Sequence Listing XML", which was created on Jun. 9, 2021, and is 3 KB in size are hereby incorporated by reference in their entirety.

BACKGROUND OF THE INVENTION

Cancer immunotherapy regimens targeting immune evasion mechanisms including checkpoint blockade (e.g. PD-1/PD-L1 and CTLA-4 blocking antibodies) have been shown to be effective in treating a variety of cancers, dramatically improving outcomes in some population's refractory to conventional therapies. However, incomplete clinical responses and the development of intrinsic or acquired resistance will continue to limit the patient populations who could benefit from checkpoint blockade.

Protein tyrosine phosphatase non-receptor type 2 (PTPN2), also known as T cell protein tyrosine phosphatase (TC-PTP), is an intracellular member of the class 1 subfamily of phospho-tyrosine specific phosphatases that control multiple cellular regulatory processes by removing phosphate groups from tyrosine substrates. PTPN2 is ubiquitously expressed, but expression is highest in hematopoietic and placental cells (Mosinger, B. Jr. et al., Proc Natl Acad Sci USA 89:499-503; 1992). In humans, PTPN2 expression is controlled post-transcriptionally by the existence of two splice variants: a 45 kDa form that contains a nuclear localization signal at the C-terminus upstream of the splice junction, and a 48 kDa canonical form which has a C-terminal ER retention motif (Tillmann U. et al., Mol Cell Biol 14:3030-3040; 1994). The 45 kDa isoform can passively transfuse into the cytosol under certain cellular stress conditions. Both isoforms share an N-terminal phospho-tyrosine phosphatase catalytic domain. PTPN2 negatively regulates signaling of non-receptor tyrosine kinases (e.g. JAK1, JAK3), receptor tyrosine kinases (e.g. INSR, EGFR, CSF1R, PDGFR), transcription factors (e.g. STAT1, STAT3, STAT5a/b), and Src family kinases (e.g. Fyn, Lck). As a critical negative regulator of the JAK-STAT pathway, PTPN2 functions to directly regulate signaling through cytokine receptors, including IFNγ. The PTPN2 catalytic domain shares 74% sequence homology with PTPN1 (also called PTP1B), and shares similar enzymatic kinetics (Romsicki Y. et al., Arch Biochem Biophys 414:40-50; 2003).

Data from a loss of function in in vivo genetic screen using CRISPR/Cas9 genome editing in a mouse B16F10 transplantable tumor model show that deletion of PTPN2 gene in tumor cells improved response to the immunotherapy regimen of a GM-CSF secreting vaccine (GVAX) plus PD-1 checkpoint blockade (Manguso R. T. et al., Nature 547:413-418; 2017). Loss of PTPN2-sensitized tumors to immunotherapy by enhancing IFNγ-mediated effects on antigen presentation and growth suppression. The same screen also revealed that genes known to be involved in immune evasion, including PD-L1 and CD47, were also depleted under immunotherapy selective pressure, while genes involved in the IFNγ signaling pathway, including IFNGR, JAK1, and STAT1, were enriched. These observations point to a role for therapeutic strategies that enhance IFNγ-sensing and signaling in enhancing the efficacy of cancer immunotherapy regimens. Thus, PTPN1 inhibitors are expected to be useful for the treatment of cancer and for cancer immunotherapy.

Protein tyrosine phosphatase non-receptor type 1 (PTPN1), also known as protein tyrosine phosphatase-1B (PTP1B), has been shown to play a key role in insulin and leptin signaling and is a primary mechanism for down-regulating both the insulin and leptin receptor signaling pathways (Kenner K. A. et al., *J Biol Chem* 271: 19810-19816, 1996). Animals deficient in PTPN1 have improved glucose regulation and lipid profiles and are resistant to weight gain when treated with a high fat diet (Elchebly M. et al., *Science* 283: 1544-1548, 1999). Thus, PTPN1 inhibitors are expected to be useful for the treatment of type 2 diabetes, obesity, and metabolic syndrome.

There is a need for therapeutic agents that can inhibit PTPN1 and PTPN2. This invention is intended to fill this unmet need associated with current protein tyrosine phosphatase enzyme inhibition therapy.

SUMMARY OF THE INVENTION

A first aspect of the invention relates to compounds of Formula (I):

(I)

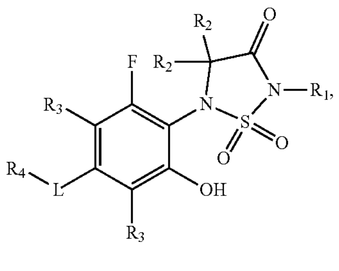

and pharmaceutically acceptable salts, stereoisomers, solvates, or tautomers thereof, wherein:

L is selected from a bond, —C(O)—, —C(O)$NR_L$—, —C(O)O—, —$NR_L$—, —$NR_L$C(O)—, —$NR_LSO_2$—, —O—, —OC(O)—, —$S(O)_2NR_L$—, —S—, and —$S(O)_2$—;

$R_L$ is selected from hydrogen, deuterium, $C_1$-$C_6$ alkyl, $C_2$-$C_6$ alkenyl, and $C_2$-$C_6$ alkynyl;

$R_1$ is selected from hydrogen, deuterium, $C_1$-$C_6$ alkyl, $C_2$-$C_6$ alkenyl, and $C_2$-$C_6$ alkynyl;

each $R_2$ is independently selected from hydrogen, deuterium, halo, —OH, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, and $C_1$-$C_6$ haloalkoxy;

each $R_3$ is independently selected from hydrogen, deuterium, halo, —OH, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, and $C_1$-$C_6$ haloalkoxy;

$R_4$ is selected from —$N(R_5)_2$, $C_1$-$C_6$ alkyl, $C_2$-$C_6$ alkenyl, $C_2$-$C_6$ alkynyl, $C_3$-$C_{10}$ cycloalkyl, aryl, 3- to 10-membered heterocyclyl, and heteroaryl, wherein the alkyl, alkenyl, alkynyl, cycloalkyl, aryl, heterocyclyl, and heteroaryl are optionally substituted with one or more $R_6$;

each $R_5$ is independently selected from hydrogen, deuterium, $C_1$-$C_6$ alkyl, $C_2$-$C_6$ alkenyl, $C_2$-$C_6$ alkynyl, $C_3$-$C_{10}$ cycloalkyl, aryl, 3- to 10-membered heterocyclyl, and heteroaryl, wherein the alkyl, alkenyl, alkynyl, cycloalkyl, aryl, heterocyclyl, and heteroaryl are optionally substituted with one or more $R_6$;

or two $R_5$, together with the nitrogen atom to which they are attached, come together to form 3- to 10-membered heterocyclyl or heteroaryl, optionally substituted with one or more $R_6$;

each $R_6$ is independently selected from —C(O)$R_7$, —C(O)$NR_NR_7$, —C(O)O$R_7$, —$NR_NR_7$, —$NR_N$C(O)$R_7$, —OC(O)$R_7$, —$S(O)_2R_7$, halo, —CN, —$NO_2$, —OH, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, aryl, 3- to 10-membered heterocyclyl, and heteroaryl, wherein the alkyl, alkenyl, alkynyl, alkoxy, cycloalkyl, aryl, heterocyclyl, and heteroaryl are optionally substituted with one or more $R_7$;

each $R_7$ is independently selected from —C(O)O$R_8$, halo, —OH, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, aryl, 3- to 10-membered heterocyclyl, and heteroaryl, wherein the alkyl, alkenyl, alkynyl, alkoxy, cycloalkyl, aryl, heterocyclyl, and heteroaryl are optionally substituted with one or more $R_8$;

each $R_8$ is independently selected from —S(O)$R_9$, halo, —CN, —OH, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, aryl, 3- to 10-membered heterocyclyl, and heteroaryl, wherein the alkyl, alkenyl, alkynyl, alkoxy, cycloalkyl, aryl, heterocyclyl, and heteroaryl are optionally substituted with one or more $R_9$;

each $R_9$ is independently selected from halo, —CN, —OH, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, aryl, 3- to 10-membered heterocyclyl, and heteroaryl, wherein the alkyl, alkenyl, alkynyl, alkoxy, cycloalkyl, aryl, heterocyclyl, and heteroaryl are optionally substituted with one or more $R_{10}$;

each $R_{10}$ is independently selected from halo, —CN, —OH, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, aryl, 3- to 10-membered heterocyclyl, and heteroaryl, wherein the alkyl, alkenyl, alkynyl, alkoxy, cycloalkyl, aryl, heterocyclyl, and heteroaryl are optionally substituted with one or more $R_1$;

each $R_1$ is independently selected from halo, —CN, —OH, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, and $C_1$-$C_6$ haloalkoxy;

each $R_N$ is independently selected from hydrogen, deuterium, $C_1$-$C_6$ alkyl, $C_2$-$C_6$ alkenyl, and $C_2$-$C_6$ alkynyl; and wherein, when L is a bond, then $R_4$ is aryl.

Another aspect of the invention is directed to pharmaceutical compositions comprising a compound of Formula (I), or a pharmaceutically acceptable salt, hydrate, solvate, prodrug, stereoisomer, or tautomer thereof, and a pharmaceutically acceptable carrier. The pharmaceutical acceptable carrier may further include an excipient, diluent, or surfactant.

Another aspect of the invention relates to a method of treating a disease or disorder associated with modulation of protein tyrosine phosphatase enzymes, such as protein tyrosine phosphatase non-receptor type 1 (PTPN1) and protein tyrosine phosphatase non-receptor type 2 (PTPN2). The method comprises administering to a patient in need of a treatment for diseases or disorders associated with modulation of protein tyrosine phosphatase enzymes an effective amount of a compound of Formula (I), or a pharmaceutically acceptable salt, hydrate, solvate, prodrug, stereoisomer, tautomer, or pharmaceutical composition thereof.

Another aspect of the invention is directed to a method of inhibiting protein tyrosine phosphatase enzymes, including, but not limited to, protein tyrosine phosphatase non-receptor type 1 (PTPN1) and protein tyrosine phosphatase non-receptor type 2 (PTPN2). The method involves administering to a patient in need thereof an effective amount of a compound of Formula (I), or a pharmaceutically acceptable salt, hydrate, solvate, prodrug, stereoisomer, tautomer, or pharmaceutical composition thereof.

Another aspect of the invention is directed to a method of treating or preventing a disease or disorder disclosed herein in a subject in need thereof. The method involves administering to a patient in need of the treatment an effective amount of a compound of Formula (I), or a pharmaceutically acceptable salt, hydrate, solvate, prodrug, stereoisomer, tautomer, or pharmaceutical composition thereof.

Another aspect of the present invention relates to compounds of Formula (I), or pharmaceutically acceptable salts, hydrates, solvates, prodrugs, stereoisomers, tautomers, or pharmaceutical compositions thereof, for use in the manufacture of a medicament for inhibiting protein tyrosine phosphatase enzymes, such as protein tyrosine phosphatase non-receptor type 1 (PTPN1) and protein tyrosine phosphatase non-receptor type 2 (PTPN2).

Another aspect of the present invention relates to compounds of Formula (I), or pharmaceutically acceptable salts, hydrates, solvates, prodrugs, stereoisomers, tautomers, or pharmaceutical compositions thereof, for use in the manufacture of a medicament for treating or preventing a disease or disorder disclosed herein.

Another aspect of the present invention relates to the use of compounds of Formula (I), or pharmaceutically acceptable salts, hydrates, solvates, prodrugs, stereoisomers, tautomers, or pharmaceutical compositions thereof, in the treatment of a disease associated with inhibiting protein tyrosine phosphatase enzymes, such as protein tyrosine phosphatase non-receptor type 1 (PTPN1) and protein tyrosine phosphatase non-receptor type 2 (PTPN2).

Another aspect of the present invention relates to the use of compounds of Formula (I), or pharmaceutically acceptable salts, hydrates, solvates, prodrugs, stereoisomers, tautomers, or pharmaceutical compositions thereof, in the treatment of a disease or disorder disclosed herein.

The present invention further provides methods of treating a disease or disorder associated with modulation of protein tyrosine phosphatase enzymes, including cancer and metabolic diseases, comprising administering to a patient suffering from at least one of said diseases or disorders a compound of Formula (I), or a pharmaceutically acceptable salt, hydrate, solvate, prodrug, stereoisomer, tautomer, or pharmaceutical composition thereof.

The present invention provides inhibitors of protein tyrosine phosphatase enzymes that are therapeutic agents in the treatment of diseases such as cancer and metabolic diseases.

The present invention further provides compounds and compositions with an improved efficacy and safety profile relative to known protein tyrosine phosphatase enzyme inhibitors. The present disclosure also provides agents with novel mechanisms of action toward protein tyrosine phosphatase enzymes in the treatment of various types of diseases, including cancer and metabolic diseases.

In some aspects, the present disclosure provides a compound obtainable by, or obtained by, a method for preparing compounds described herein (e.g., a method comprising one or more steps described in General Procedures A-C).

In some aspects, the present disclosure provides an intermediate as described herein, being suitable for use in a method for preparing a compound as described herein (e.g., the intermediate is selected from the intermediates described in Examples 1-112 and A-C).

In some aspects, the present disclosure provides a method of preparing compounds of the present disclosure.

In some aspects, the present disclosure provides a method of preparing compounds of the present disclosure, comprising one or more steps described herein.

Unless otherwise defined, all technical and scientific terms used herein have the same meaning as commonly understood by one of ordinary skill in the art to which this disclosure belongs. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting. In the case of conflict between the chemical structures and names of the compounds disclosed herein, the chemical structures will control.

Other features and advantages of the disclosure will be apparent from the following detailed description and claims.

DETAILED DESCRIPTION OF THE INVENTION

The present disclosure relates to compounds and compositions that are capable of inhibiting the activity protein tyrosine phosphatase enzymes, including, but not limited to, protein tyrosine phosphatase non-receptor type 1 (PTPN1) and protein tyrosine phosphatase non-receptor type 2 (PTPN2). The disclosure features methods of treating, preventing or ameliorating a disease or disorder in which protein tyrosine phosphatase enzymes play a role by administering to a patient in need thereof a therapeutically effective amount of a compound of Formula (I), or a pharmaceutically acceptable salt, hydrate, solvate, prodrug, stereoisomer, or tautomer thereof. The methods of the present invention can be used in the treatment of a variety of protein tyrosine phosphatase enzyme-mediated diseases and disorders by inhibiting the activity of protein tyrosine phosphatase enzymes. Inhibition of protein tyrosine phosphatase enzyme can be an effective approach to the treatment, prevention, or amelioration of diseases including, but not limited to, cancer and metabolic diseases. Decreasing protein tyrosine phosphatase enzyme activity can suppress cancer mutagenesis, dampen tumor evolution, and/or decrease the probability of adverse outcomes, such as drug resistance and/or metastases.

In a first aspect of the invention, the compounds of Formula (I) are described:

(I)

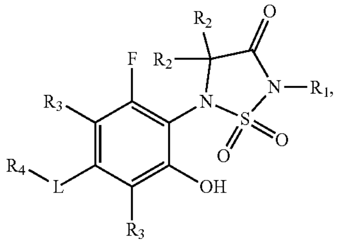

and pharmaceutically acceptable salts, hydrates, solvates, prodrugs, stereoisomers, and tautomers thereof, wherein L, $R_1$, $R_2$, $R_3$, and $R_4$ are described herein.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

The term "optionally substituted" is understood to mean that a given chemical moiety (e.g., an alkyl group) can (but is not required to) be bonded other substituents (e.g., heteroatoms). For instance, an alkyl group that is optionally substituted can be a fully saturated alkyl chain (i.e., a pure hydrocarbon). Alternatively, the same optionally substituted alkyl group can have substituents different from hydrogen. For instance, it can, at any point along the chain be bounded to a halogen atom, a hydroxyl group, or any other substituent described herein. Thus, the term "optionally substituted" means that a given chemical moiety has the potential to contain other functional groups, but does not necessarily have any further functional groups. Suitable substituents used in the optional substitution of the described groups include, without limitation, halogen, oxo, —OH, —CN, —COOH, —$CH_2$CN, —O—($C_1$-$C_6$) alkyl, ($C_1$-$C_6$) alkyl, ($C_1$-$C_6$) alkoxy, ($C_1$-$C_6$) haloalkyl, ($C_1$-$C_6$)haloalkoxy, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)$(OH)_2$, —OC(O)($C_1$-$C_6$) alkyl, —C(O)($C_1$-$C_6$) alkyl, —OC(O)O($C_1$-$C_6$) alkyl, —$NH_2$, —NH(($C_1$-$C_6$) alkyl), —N(($C_1$-$C_6$) alkyl$)_2$, —NHC(O)($C_1$-$C_6$) alkyl, —C(O)NH($C_1$-$C_6$) alkyl, —S$(O)_2$($C_1$-$C_6$) alkyl, —S(O)NH($C_1$-$C_6$) alkyl, and S(O)N(($C_1$-$C_6$) alkyl$)_2$. The substituents can themselves be optionally substituted. "Optionally substituted" as used herein also refers to substituted or unsubstituted whose meaning is described below.

As used herein, the term "substituted" means that the specified group or moiety bears one or more suitable substituents wherein the substituents may connect to the specified group or moiety at one or more positions. For example, an aryl substituted with a cycloalkyl may indicate that the cycloalkyl connects to one atom of the aryl with a bond or by fusing with the aryl and sharing two or more common atoms.

As used herein, the term "unsubstituted" means that the specified group bears no substituents.

Unless otherwise specifically defined, the term "aryl" refers to cyclic, aromatic hydrocarbon groups that have 1 to 3 aromatic rings, including monocyclic or bicyclic groups such as phenyl, biphenyl, or naphthyl. Where containing two aromatic rings (bicyclic, etc.), the aromatic rings of the aryl group may be joined at a single point (e.g., biphenyl), or fused (e.g., naphthyl). The aryl group may be optionally substituted by one or more substituents, e.g., 1 to 5 substituents, at any point of attachment. Exemplary substituents include, but are not limited to, —H, -halogen, —O—($C_1$-$C_6$) alkyl, ($C_1$-$C_6$) alkyl, —O—($C_2$-$C_6$) alkenyl, —O—($C_2$-$C_6$) alkynyl, ($C_2$-$C_6$) alkenyl, ($C_2$-$C_6$) alkynyl, —OH, —OP(O)$(OH)_2$, —OC(O)($C_1$-$C_6$) alkyl, —C(O)($C_1$-$C_6$) alkyl, —OC(O)O($C_1$-$C_6$) alkyl, —$NH_2$, NH(($C_1$-$C_6$) alkyl), N(($C_1$-$C_6$) alkyl$)_2$, —S$(O)_2$—($C_1$-$C_6$) alkyl, —S(O)NH($C_1$-$C_6$) alkyl, and —S(O)N(($C_1$-$C_6$) alkyl$)_2$. The substituents can themselves be optionally substituted. Furthermore, when containing two fused rings, the aryl groups herein defined may have a saturated or partially unsaturated ring fused with a fully unsaturated aromatic ring. Exemplary ring systems of these aryl groups include, but are not limited to, phenyl, biphenyl, naphthyl, anthracenyl, phenalenyl, phenanthrenyl, indanyl, indenyl, tetrahydronaphthalenyl, tetrahydrobenzoannulenyl, and the like.

Unless otherwise specifically defined, "heteroaryl" means a monovalent monocyclic or polycyclic aromatic radical of 5 to 24 ring atoms, containing one or more ring heteroatoms selected from N, O, S, P, Se, or B, the remaining ring atoms being C. Heteroaryl as herein defined also means a bicyclic heteroaromatic group wherein the heteroatom is selected from N, O, S, P, Se, or B. Heteroaryl as herein defined also means a tricyclic heteroaromatic group containing one or more ring heteroatoms selected from N, O, S, P, Se, or B. The aromatic radical is optionally substituted independently with one or more substituents described herein. Examples include, but are not limited to, furyl, thienyl, pyrrolyl, pyridyl, pyrazolyl, pyrimidinyl, imidazolyl, isoxazolyl, oxazolyl, oxadiazolyl, pyrazinyl, indolyl, thiophen-2-yl, quinolinyl, benzopyranyl, isothiazolyl, thiazolyl, thiadiazole, indazole, benzimidazolyl, thieno[3,2-b]thiophene, triazolyl, triazinyl, imidazo[1,2-b]pyrazolyl, furo[2,3-c]pyridinyl, imidazo[1,2-a]pyridinyl, indazolyl, pyrrolo[2,3-c]pyridinyl, pyrrolo[3,2-c]pyridinyl, pyrazolo[3,4-c]pyridinyl, thieno[3,2-c]pyridinyl, thieno[2,3-c]pyridinyl, thieno[2,3-b]pyridinyl, benzothiazolyl, indolyl, indolinyl, indolinonyl, dihydrobenzothiophenyl, dihydrobenzofuranyl, benzofuran, chromanyl, thiochromanyl, tetrahydroquinolinyl, dihydrobenzothiazine, quinolinyl, isoquinolinyl, 1,6-naphthyridinyl, benzo[de]isoquinolinyl, pyrido[4,3-b][1,6]naphthyridinyl, thieno[2,3-b]pyrazinyl, quinazolinyl, tetrazolo[1,5-a]pyridinyl, [1,2,4]triazolo[4,3-a]pyridinyl, isoindolyl, pyrrolo[2,3-b]pyridinyl, pyrrolo[3,4-b]pyridinyl, pyrrolo[3,2-b]pyridinyl, imidazo[5,4-b]pyridinyl, pyrrolo[1,2-a]pyrimidinyl, tetrahydro pyrrolo[1,2-a]pyrimidinyl, 3,4-dihydro-2H-1$\lambda^2$-pyrrolo[2,1-b]pyrimidine, dibenzo[b,d]thiophene, pyridin-2-one, furo[3,2-c]pyridinyl, furo[2,3-c]pyridinyl, 1H-pyrido[3,4-b][1,4]thiazinyl, benzoxazolyl, benzisoxazolyl, furo[2,3-b]pyridinyl, benzothiophenyl, 1,5-naphthyridinyl, furo[3,2-b]pyridine, [1,2,4]triazolo[1,5-a]pyridinyl, benzo [1,2,3]triazolyl, imidazo[1,2-a]pyrimidinyl, [1,2,4]triazolo[4,3-b]pyridazinyl, benzo[c][1,2,5]thiadiazolyl, benzo[c][1,2,5]oxadiazole, 1,3-dihydro-2H-benzo[d]imidazol-2-one, 3,4-dihydro-2H-pyrazolo [1,5-b][1,2]oxazinyl, 4,5,6,7-tetrahydropyrazolo[1,5-a]pyridinyl, thiazolo[5,4-d]thiazolyl, imidazo[2,1-b][1,3,4]thiadiazolyl, thieno[2,3-b]pyrrolyl, 3H-indolyl, and derivatives thereof. Furthermore, when containing two or more fused rings, the heteroaryl groups defined herein may have one or more saturated or partially unsaturated ring fused with a fully unsaturated aromatic ring, e.g., a 5-membered heteroaromatic ring containing 1 to 3 heteroatoms selected from N, O, S, P, Se, or B, or a 6-membered heteroaromatic ring containing 1 to 3 nitrogens, wherein the saturated or partially unsaturated ring includes 0 to 4 heteroatoms selected from N, O, S, P, Se, or B, and is optionally substituted with one or more oxo. In heteroaryl ring systems containing more than two fused rings, a saturated or partially unsaturated ring may further be fused with a saturated or partially unsaturated ring described herein. Exemplary ring systems of these heteroaryl groups include, for example, indolinyl, indolinonyl, dihydrobenzothiophenyl, dihydrobenzofuran, chromanyl, thiochromanyl, tetrahydroquinolinyl, dihydrobenzothiazine, 3,4-dihydro-1H-isoquinolinyl, 2,3-dihydrobenzofuranyl, benzofuranonyl, indolinyl, oxindolyl, indolyl, 1,6-dihydro-7H-pyrazolo[3,4-c]pyridin-7-onyl, 7,8-dihydro-6H-pyrido[3,2-b]pyrrolizinyl, 8H-pyrido[3,2-b]pyrrolizinyl, 1,5,6,7-tetrahydrocyclopenta[b]pyrazolo[4,3-e]pyridinyl, 7,8-dihydro-6H-pyrido[3,2-b]pyrrolizine, pyrazolo[1,5-a]pyrimidin-7(4H)-only, 3,4-dihydropyrazino[1,2-a]indol-1(2H)-onyl, or benzo[c][1,2]oxaborol-1(3H)-olyl.

"Halogen" or "halo" refers to fluorine, chlorine, bromine, or iodine.

"Alkyl" refers to a straight or branched chain saturated hydrocarbon containing 1-12 carbon atoms. Examples of a ($C_1$-$C_6$) alkyl group include, but are not limited to, methyl, ethyl, propyl, butyl, pentyl, hexyl, isopropyl, isobutyl, sec-butyl, tert-butyl, isopentyl, neopentyl, and isohexyl.

"Alkoxy" refers to a straight or branched chain saturated hydrocarbon containing 1-12 carbon atoms containing a terminal "O" in the chain, i.e., —O(alkyl). Examples of alkoxy groups include without limitation, methoxy, ethoxy, propoxy, butoxy, t-butoxy, or pentoxy groups.

"Alkenyl" refers to a straight or branched chain unsaturated hydrocarbon containing 2-12 carbon atoms. The "alkenyl" group contains at least one double bond in the chain. The double bond of an alkenyl group can be unconjugated or conjugated to another unsaturated group. Examples of alkenyl groups include ethenyl, propenyl, n-butenyl, iso-butenyl, pentenyl, or hexenyl. An alkenyl group can be unsubstituted or substituted. Alkenyl, as herein defined, may be straight or branched.

"Alkynyl" refers to a straight or branched chain unsaturated hydrocarbon containing 2-12 carbon atoms. The "alkynyl" group contains at least one triple bond in the chain. Examples of alkenyl groups include ethynyl, propargyl, n-butynyl, iso-butynyl, pentynyl, or hexynyl. An alkynyl group can be unsubstituted or substituted.

The term "alkylene" or "alkylenyl" refers to a divalent alkyl radical. Any of the above-mentioned monovalent alkyl groups may be an alkylene by abstraction of a second hydrogen atom from the alkyl. As herein defined, alkylene may also be a $C_1$-$C_6$ alkylene. An alkylene may further be a $C_1$-$C_4$ alkylene. Typical alkylene groups include, but are not limited to, $—CH_2—CH(CH_3)—$, $—C(CH_3)_2—$, $—CH_2CH_2—$, $—CH_2CH(CH_3)—$, $—CH_2C(CH_3)_2—$, $—CH_2CH_2CH_2—$, $—CH_2CH_2CH_2CH_2—$, and the like.

"Cycloalkyl" means a saturated or partially unsaturated hydrocarbon monocyclic or polycyclic (e.g., fused, bridged, or spiro rings) system having 3 to 30 carbon atoms (e.g., $C_3$-$C_{12}$, $C_3$-$C_{10}$, or $C_3$-$C_8$). Examples of cycloalkyl groups include, without limitations, cyclopropyl, cyclobutyl, cyclopentyl, cyclohexyl, cycloheptanyl, cyclooctanyl, norboranyl, norborenyl, bicyclo[2.2.2]octanyl, bicyclo[2.2.2]octenyl, decahydronaphthalenyl, octahydro-1H-indenyl, cyclopentenyl, cyclohexenyl, cyclohexa-1,4-dienyl, cyclohexa-1,3-dienyl, 1,2,3,4-tetrahydronaphthalenyl, octahydropentalenyl, 3a,4,5,6,7,7a-hexahydro-1H-indenyl, 1,2,3,3a-tetrahydropentalenyl, bicyclo[3.1.0]hexanyl, bicyclo[2.1.0]pentanyl, spiro[3.3]heptanyl, bicyclo[2.2.1]heptanyl, bicyclo[2.2.1]hept-2-enyl, bicyclo[2.2.2]octanyl, 6-methylbicyclo[3.1.1]heptanyl, 2,6,6-trimethylbicyclo[3.1.1]heptanyl, adamantyl, and derivatives thereof. In the case of polycyclic cycloalkyl, only one of the rings in the cycloalkyl needs to be non-aromatic.

"Heterocyclyl", "heterocycle" or "heterocycloalkyl" refers to a saturated or partially unsaturated 3-10 membered monocyclic, 7-12 membered bicyclic (fused, bridged, or spiro rings), or 11-14 membered tricyclic ring system (fused, bridged, or spiro rings) having one or more heteroatoms (such as O, N, S, P, Se, or B), e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur, unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, dihydropyranyl, pyranyl, morpholinyl, tetrahydrothiopyranyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl, 1,4-dioxaspiro[4.5]decanyl, 1-oxaspiro[4.5]decanyl, 1-azaspiro[4.5]decanyl, 3'H-spiro[cyclohexane-1,1'-isobenzofuran]-yl, 7'H-spiro[cyclohexane-1,5'-furo[3,4-b]pyridin]-yl, 3'H-spiro[cyclohexane-1,1'-furo[3,4-c]pyridin]-yl, 3-azabicyclo[3.1.0]hexanyl, 3-azabicyclo[3.1.0]hexan-3-yl, 1,4,5,6-tetrahydropyrrolo[3,4-c]pyrazolyl, 3,4,5,6,7,8-hexahydropyrido[4,3-d]pyrimidinyl, 4,5,6,7-tetrahydro-1H-pyrazolo[3,4-c]pyridinyl, 5,6,7,8-tetrahydropyrido[4,3-d]pyrimidinyl, 2-azaspiro[3.3]heptanyl, 2-methyl-2-azaspiro[3.3]heptanyl, 2-azaspiro[3.5]nonanyl, 2-methyl-2-azaspiro[3.5]nonanyl, 2-azaspiro[4.5]decanyl, 2-methyl-2-azaspiro[4.5]decanyl, 2-oxa-azaspiro[3.4]octanyl, 2-oxa-azaspiro[3.4]octan-6-yl, and the like.

The term "haloalkyl" as used herein refers to an alkyl group, as defined herein, which is substituted one or more halogen. Examples of haloalkyl groups include, but are not limited to, trifluoromethyl, difluoromethyl, pentafluoroethyl, trichloromethyl, etc.

The term "haloalkoxy" as used herein refers to an alkoxy group, as defined herein, which is substituted one or more halogen. Examples of haloalkoxy groups include, but are not limited to, trifluoromethoxy, difluoromethoxy, pentafluoroethoxy, trichloromethoxy, etc.

The term "cyano" as used herein means a substituent having a carbon atom joined to a nitrogen atom by a triple bond, i.e., C≡N.

The term "amine" as used herein refers to primary ($R—NH_2$, $R≠H$), secondary ($R_2—NH$, $R_2≠H$) and tertiary ($R_3—N$, $R≠H$) amines. A substituted amine is intended to mean an amine where at least one of the hydrogen atoms has been replaced by the substituent.

The term "amino" as used herein means a substituent containing at least one nitrogen atom. Specifically, $—NH_2$, —NH(alkyl) or alkylamino, $—N(alkyl)_2$ or dialkylamino, amide-, carbamide-, urea, and sulfamide substituents are included in the term "amino".

The term "solvate" refers to a complex of variable stoichiometry formed by a solute and solvent. Such solvents for the purpose of the invention may not interfere with the biological activity of the solute. Examples of suitable solvents include, but are not limited to, water, MeOH, EtOH, and AcOH. Solvates wherein water is the solvent molecule are typically referred to as hydrates. Hydrates include compositions containing stoichiometric amounts of water, as well as compositions containing variable amounts of water.

The term "isomer" refers to compounds that have the same composition and molecular weight but differ in physical and/or chemical properties. The structural difference may be in constitution (geometric isomers) or in the ability to rotate the plane of polarized light (stereoisomers). With regard to stereoisomers, the compounds of Formula (I) may have one or more asymmetric carbon atom and may occur as racemates, racemic mixtures and as individual enantiomers or diastereomers.

The present invention also contemplates isotopically labelled compounds of Formula I (e.g., those labeled with $^2H$ and $^{14}C$). Deuterated (i.e., $^2H$ or D) and carbon-14 (i.e., $^{14}C$) isotopes are particularly preferred for their ease of preparation and detectability. Further, substitution with heavier isotopes such as deuterium may afford certain therapeutic advantages resulting from greater metabolic stability (e.g., increased in vivo half-life or reduced dosage requirements) and hence may be preferred in some circumstances. Isotopically labelled compounds of Formula I can generally be prepared by following procedures analogous to those disclosed in the Schemes and/or in the Examples herein below, by substituting an appropriate isotopically labelled reagent for a non-isotopically labelled reagent.

The disclosure also includes pharmaceutical compositions comprising an effective amount of a disclosed compound and a pharmaceutically acceptable carrier. Representative "pharmaceutically acceptable salts" include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumerate, fiunarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

A "patient" or "subject" is a mammal, e.g., a human, mouse, rat, guinea pig, dog, cat, horse, cow, pig, or non-human primate, such as a monkey, chimpanzee, baboon or rhesus.

An "effective amount" when used in connection with a compound is an amount effective for treating or preventing a disease or disorder in a subject as described herein.

The term "carrier", as used in this disclosure, encompasses carriers, excipients, and diluents and means a material, composition or vehicle, such as a liquid or solid filler, diluent, excipient, solvent or encapsulating material, involved in carrying or transporting a pharmaceutical agent from one organ, or portion of the body, to another organ, or portion of the body of a subject.

The term "treating" with regard to a subject, refers to improving at least one symptom of the subject's disorder. Treating includes curing, improving, or at least partially ameliorating the disorder.

The term "disorder" is used in this disclosure to mean, and is used interchangeably with, the terms disease, condition, or illness, unless otherwise indicated.

The term "administer", "administering", or "administration" as used in this disclosure refers to either directly administering a disclosed compound or pharmaceutically acceptable salt of the disclosed compound or a composition to a subject, or administering a prodrug derivative or analog of the compound or pharmaceutically acceptable salt of the compound or composition to the subject, which can form an equivalent amount of active compound within the subject's body.

The term "prodrug," as used in this disclosure, means a compound which is convertible in vivo by metabolic means (e.g., by hydrolysis) to a disclosed compound.

The present invention relates to compounds or pharmaceutically acceptable salts, hydrates, solvates, prodrugs, stereoisomers, or tautomers thereof, capable of inhibiting protein tyrosine phosphatase enzymes, such as protein tyrosine phosphatase non-receptor type 1 (PTPN1) and protein tyrosine phosphatase non-receptor type 2 (PTPN2), which are useful for the treatment of diseases and disorders associated with modulation of an protein tyrosine phosphatase enzyme. The invention further relates to compounds, or pharmaceutically acceptable salts, hydrates, solvates, prodrugs, stereoisomers, or tautomers thereof, which can be useful for inhibiting protein tyrosine phosphatase enzyme.

In some embodiments, the compounds of Formula (I) have the structure of Formula I-A-1, I-A-2, or I-A-3:

(I-A-1)

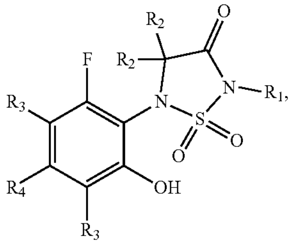

(I-A-2)

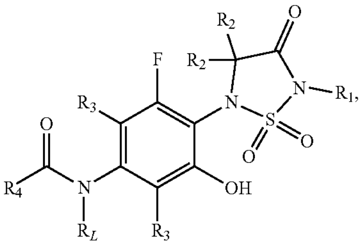

or (I-A-3)

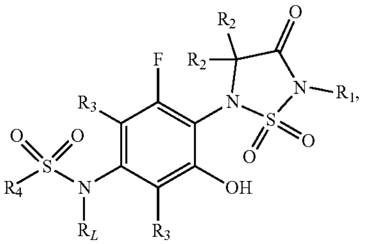

and pharmaceutically acceptable salts, stereoisomers, solvates, prodrugs, or tautomers thereof.

In some embodiments, the compounds of Formula (I) have the structure of Formula I-A-1.

In some embodiments, the compounds of Formula (I) have the structure of Formula I-A-2.

In some embodiments, the compounds of Formula (I) have the structure of Formula I-A-3.

In some embodiments, the compounds of Formula (I) have the structure of Formula I-A-2-A:

(I-A-2-A)

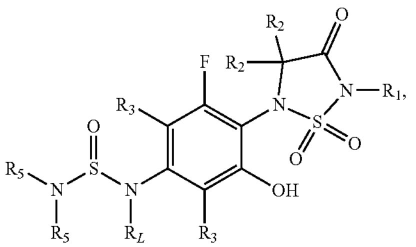

and pharmaceutically acceptable salts, stereoisomers, solvates, prodrugs, or tautomers thereof.

In some embodiments, the compounds of Formula (I) have the structure of Formula I-B:

(I-B)

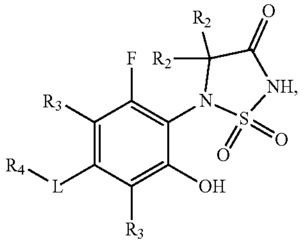

and pharmaceutically acceptable salts, stereoisomers, solvates, prodrugs, or tautomers thereof.

In some embodiments, the compounds of Formula (I) have the structure of Formula I-C:

(I-C)

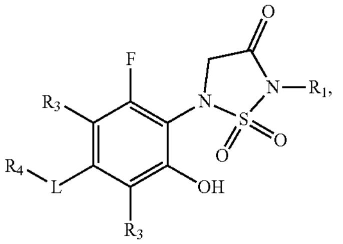

and pharmaceutically acceptable salts, stereoisomers, solvates, prodrugs, or tautomers thereof.

In some embodiments, the compounds of Formula (I) have the structure of Formula I-D:

(I-D)

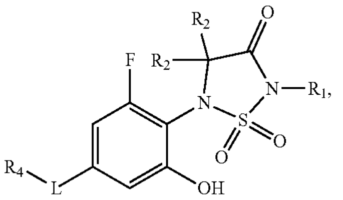

and pharmaceutically acceptable salts, stereoisomers, solvates, prodrugs, or tautomers thereof.

In some embodiments, the compounds of Formula (I) have the structure of Formula I-E:

(I-E)

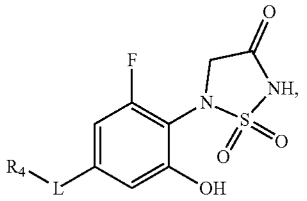

and pharmaceutically acceptable salts, stereoisomers, solvates, prodrugs, or tautomers thereof.

In some embodiments, the compounds of Formula (I) have the structure of Formula I-F-1 or I-F-2:

(I-F-1)

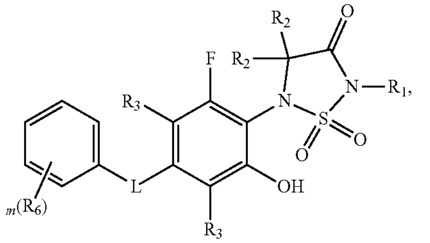

or (I-F-2)

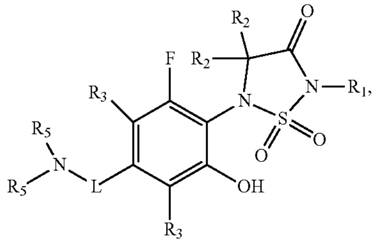

and pharmaceutically acceptable salts, stereoisomers, solvates, prodrugs, or tautomers thereof, wherein m is an integer selected from 0, 1, 2, 3, 4, and 5.

In some embodiments, the compounds of Formula (I) have the structure of Formula I-F-1.

In some embodiments, the compounds of Formula (I) have the structure of Formula I-F-2.

In some embodiments, the compounds of Formula (I) have the structure of Formula I-F-2-A or I-F-2-B:

(I-F-2-A)

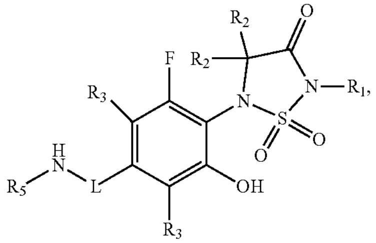

or (I-F-2-B)

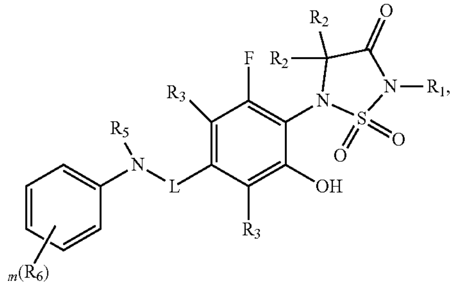

and pharmaceutically acceptable salts, stereoisomers, solvates, prodrugs, or tautomers thereof, wherein m is an integer selected from 0, 1, 2, 3, 4, and 5.

In some embodiments, the compounds of Formula (I) have the structure of Formula I-F-2-A.

In some embodiments, the compounds of Formula (I) have the structure of Formula-F-2-B.

In some embodiments, the compounds of Formula (I) have the structure of Formula I-G:

(I-G)

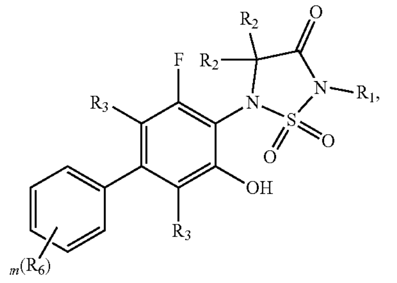

and pharmaceutically acceptable salts, stereoisomers, solvates, prodrugs, or tautomers thereof, wherein m is an integer selected from 0, 1, 2, 3, 4, and 5.

In some embodiments, m is 0. In some embodiments, m is 1. In some embodiments, m is 2. In some embodiments, m is 3. In some embodiments, m is 4. In some embodiments, m is 5.

In some embodiments, L is bond. In some embodiments, L is —C(O)—. In some embodiments, L is —C(O)NR$_L$—. In some embodiments, L is —C(O)O—. In some embodiments, L is —NR$_L$—. In some embodiments, L is —NR$_L$C(O)—. In some embodiments, L is —NR$_L$SO$_2$—. In some embodiments, L is —O—. In some embodiments, L is —OC(O)—. In some embodiments, L is —S(O)$_2$NR$_L$—. In some embodiments, L is —S—. In some embodiments, L is —S(O)$_2$—.

In some embodiments, $R_L$ is hydrogen. In some embodiments, $R_L$ is deuterium. In some embodiments, $R_L$ is $C_1$-$C_6$ alkyl. In some embodiments, $R_L$ is methyl. In some embodiments, $R_L$ is ethyl. In some embodiments, $R_L$ is propyl. In some embodiments, $R_L$ is isopropyl. In some embodiments, $R_L$ is butyl. In some embodiments, $R_L$ is isobutyl. In some embodiments, $R_L$ is sec-butyl. In some embodiments, $R_L$ is tert-butyl. In some embodiments, $R_L$ is pentyl. In some embodiments, $R_L$ is isopentyl. In some embodiments, $R_L$ is sec-pentyl. In some embodiments, $R_L$ is neopentyl. In some embodiments, $R_L$ is hexyl. In some embodiments, $R_L$ is isohexyl. In some embodiments, $R_L$ is $C_2$-$C_6$ alkenyl. In some embodiments, $R_L$ is $C_2$-$C_6$ alkynyl.

In some embodiments, $R_1$ is hydrogen. In some embodiments, $R_1$ is deuterium. In some embodiments, $R_1$ is $C_1$-$C_6$ alkyl. In some embodiments, $R_1$ is methyl. In some embodiments, $R_1$ is ethyl. In some embodiments, $R_1$ is propyl. In some embodiments, $R_1$ is isopropyl. In some embodiments, $R_1$ is butyl. In some embodiments, $R_1$ is isobutyl. In some embodiments, $R_1$ is sec-butyl. In some embodiments, $R_1$ is tert-butyl. In some embodiments, $R_1$ is pentyl. In some embodiments, $R_1$ is isopentyl. In some embodiments, $R_1$ is sec-pentyl. In some embodiments, $R_1$ is neopentyl. In some embodiments, $R_1$ is hexyl. In some embodiments, $R_1$ is isohexyl. In some embodiments, $R_1$ is $C_2$-$C_6$ alkenyl. In some embodiments, $R_1$ is $C_2$-$C_6$ alkynyl.

In some embodiments, at least one $R_2$ is hydrogen. In some embodiments, at least one $R_2$ is deuterium. In some embodiments, at least one $R_2$ is halo. In some embodiments, at least one $R_2$ is fluoro. In some embodiments, at least one $R_2$ is chloro. In some embodiments, at least one $R_2$ is bromo. In some embodiments, at least one $R_2$ is iodo. In some embodiments, at least one $R_2$ is —OH. In some embodiments, at least one $R_2$ is —CN. In some embodiments, at least one $R_2$ is —NO$_2$. In some embodiments, at least one $R_2$ is $C_1$-$C_6$ alkyl. In some embodiments, at least one v is methyl. In some embodiments, at least one $R_2$ is ethyl. In some embodiments, at least one $R_2$ is propyl. In some embodiments, at least one $R_2$ is isopropyl. In some embodiments, at least one $R_2$ is butyl. In some embodiments, at least one $R_2$ is isobutyl. In some embodiments, at least one $R_2$ is sec-butyl. In some embodiments, at least one $R_2$ is tert-butyl. In some embodiments, at least one $R_2$ is pentyl. In some embodiments, at least one $R_2$ is isopentyl. In some embodiments, at least one $R_2$ is sec-pentyl. In some embodiments, at least one $R_2$ is neopentyl. In some embodiments, at least one $R_2$ is hexyl. In some embodiments, at least one $R_2$ is isohexyl. In some embodiments, at least one $R_2$ is $C_2$-$C_6$ alkenyl. In some embodiments, at least one $R_2$ is $C_2$-$C_6$ alkynyl. In some embodiments, at least one $R_2$ is $C_1$-$C_6$ haloalkyl. In some embodiments, at least one $R_2$ is $C_1$-$C_6$ alkoxy. In some embodiments, at least one $R_2$ is $C_1$-$C_6$ haloalkoxy.

In some embodiments, each $R_2$ is hydrogen.

In some embodiments, at least one $R_3$ is hydrogen. In some embodiments, at least one $R_3$ is deuterium. In some embodiments, at least one $R_3$ is halo. In some embodiments, at least one $R_3$ is fluoro. In some embodiments, at least one $R_3$ is chloro. In some embodiments, at least one $R_3$ is bromo. In some embodiments, at least one $R_3$ is iodo. In some embodiments, at least one $R_3$ is —OH. In some embodiments, at least one $R_3$ is —CN. In some embodiments, at least one $R_3$ is —NO$_3$. In some embodiments, at least one $R_3$ is $C_1$-$C_6$ alkyl. In some embodiments, at least one $R_3$ is methyl. In some embodiments, at least one $R_3$ is ethyl. In some embodiments, at least one $R_3$ is propyl. In some embodiments, at least one $R_3$ is isopropyl. In some embodiments, at least one $R_3$ is butyl. In some embodiments, at least one $R_3$ is isobutyl. In some embodiments, at least one $R_3$ is sec-butyl. In some embodiments, at least one $R_3$ is tert-butyl. In some embodiments, at least one $R_3$ is pentyl. In some embodiments, at least one $R_3$ is isopentyl. In some embodiments, at least one $R_3$ is sec-pentyl. In some embodiments, at least one $R_3$ is neopentyl. In some embodiments, at least one $R_3$ is hexyl. In some embodiments, at least one $R_3$ is isohexyl. In some embodiments, at least one $R_3$ is $C_2$-$C_6$ alkenyl. In some embodiments, at least one $R_3$ is $C_3$-$C_6$ alkynyl. In some embodiments, at least one $R_3$ is $C_1$-$C_6$ haloalkyl. In some embodiments, at least one $R_3$ is $C_1$-$C_6$ alkoxy. In some embodiments, at least one $R_3$ is $C_1$-$C_6$ haloalkoxy.

In some embodiments, each $R_3$ is hydrogen.

In some embodiments, $R_1$, each $R_2$, and each $R_3$ are hydrogen.

In some embodiments, $R_4$ is —N(R$_5$)$_2$. In some embodiments, $R_4$ is $C_1$-$C_6$ alkyl. In some embodiments, $R_4$ is $C_1$-$C_6$ alkyl substituted with one or more $R_6$. In some embodiments, $R_4$ is methyl. In some embodiments, $R_4$ is ethyl. In some embodiments, $R_4$ is propyl. In some embodiments, $R_4$ is isopropyl. In some embodiments, $R_4$ is butyl. In some embodiments, $R_4$ is isobutyl. In some embodiments, $R_4$ is sec-butyl. In some embodiments, $R_4$ is tert-butyl. In some embodiments, $R_4$ is pentyl. In some embodiments, $R_4$ is isopentyl. In some embodiments, $R_4$ is sec-pentyl. In some embodiments, $R_4$ is neopentyl. In some embodiments, $R_4$ is hexyl. In some embodiments, $R_4$ is isohexyl. In some embodiments, $R_4$ is $C_2$-$C_6$ alkenyl. In some embodiments, $R_4$ is $C_2$-$C_6$ alkenyl substituted with one or more $R_6$. In some embodiments, $R_4$ is $C_2$-$C_6$ alkynyl. In some embodiments, $R_4$ is $C_2$-$C_6$ alkynyl substituted with one or more $R_6$. In some embodiments, $R_4$ is $C_3$-$C_{10}$ cycloalkyl. In some embodiments, $R_4$ is $C_3$-$C_{10}$ cycloalkyl substituted with one or more $R_6$. In some embodiments, $R_4$ is cyclopropyl. In some embodiments, $R_4$ is cyclopropyl substituted with one or more $R_6$. In some embodiments, $R_4$ is cyclopentyl. In some embodiments, $R_4$ is cyclopropyl substituted with one or more $R_6$. In some embodiments, $R_4$ is cyclohexyl. In some embodiments, $R_4$ is cyclohexyl substituted with one or more $R_6$. In some embodiments, $R_4$ is cycloheptyl. In some embodiments, $R_4$ is cycloheptyl substituted with one or more $R_6$. In some embodiments, $R_4$ is adamantyl. In some embodiments, $R_4$ is adamantly substituted with one or more $R_6$. In some embodiments, $R_4$ is aryl. In some embodiments, $R_4$ is aryl substituted with one or more $R_6$. In some embodiments, $R_4$ is phenyl. In some embodiments, $R_4$ is phenyl substituted with one or more $R_6$. In some embodiments, $R_4$ is 3- to 10-membered heterocyclyl. In some embodiments, $R_4$ is 3- to 10-membered heterocyclyl substituted with one or more $R_6$. In some embodiments, $R_4$ is tetrahydrofuranyl. In some embodiments, $R_4$ is tetrahydrofuranyl substituted with one or more $R_6$. In some embodiments, $R_4$ is piperidinyl. In some embodiments, $R_4$ is piperidinyl substituted with one or more $R_6$. In some embodiments, $R_4$ is piperazinyl. In some embodiments, $R_4$ is piperazinyl substituted with one or more $R_6$. In some embodiments, $R_4$ is morpholinyl. In some embodiments, $R_4$ is morpholinyl substituted with one or more $R_6$. In some embodiments, $R_4$ is heteroaryl. In some embodiments, $R_4$ is heteroaryl substituted with one or more $R_6$. In some embodiments, $R_4$ is pyrazolyl. In some embodiments, $R_4$ is pyrazolyl substituted with one or more $R_6$. In some embodiments, $R_4$ is pyridinyl. In some embodiments, $R_4$ is pyridinyl substituted with one or more $R_6$. In some embodiments, $R_4$ is benzimidazolyl. In some embodiments, $R_4$ is benzimidazolyl substituted with one or more $R_6$. In some embodiments, $R_4$ is dihydroisoquinolinyl. In some embodiments, $R_4$ is dihydroisoquinolinyl substituted with one or more $R_6$. In some embodiments, $R_4$ is tetrahydroquinolinyl. In some embodiments, $R_4$ is tetrahydroquinolinyl substituted with one or more $R_6$.

In some embodiments, at least one $R_5$ is hydrogen. In some embodiments, at least one $R_5$ is deuterium. In some embodiments, at least one $R_5$ is $C_1$-$C_6$ alkyl. In some embodiments, at least one $R_5$ is $C_1$-$C_6$ alkyl substituted with one or more $R_6$. In some embodiments, at least one $R_5$ is methyl. In some embodiments, at least one $R_5$ is ethyl. In some embodiments, at least one $R_5$ is propyl. In some embodiments, at least one $R_5$ is isopropyl. In some embodiments, at least one $R_5$ is butyl. In some embodiments, at least one $R_5$ is isobutyl. In some embodiments, at least one $R_5$ is sec-butyl. In some embodiments, at least one $R_5$ is tert-butyl. In some embodiments, at least one $R_5$ is pentyl. In some embodiments, at least one $R_5$ is isopentyl. In some embodiments, at least one $R_5$ is sec-pentyl. In some embodiments, at least one $R_5$ is neopentyl. In some embodiments, at least one $R_5$ is hexyl. In some embodiments, at least one $R_5$ is isohexyl. In some embodiments, at least one $R_5$ is $C_2$-$C_6$ alkenyl. In some embodiments, at least one $R_5$ is $C_2$-$C_6$ alkenyl substituted with one or more $R_6$. In some embodiments, at least one $R_5$ is $C_2$-$C_6$ alkynyl. In some embodiments, at least one $R_5$ is $C_2$-$C_6$ alkynyl substituted with one or more $R_6$. In some embodiments, at least one $R_5$ is $C_3$-$C_{10}$ cycloalkyl. In some embodiments, at least one $R_5$ is $C_3$-$C_{10}$ cycloalkyl substituted with one or more $R_6$. In some embodiments, at least one $R_5$ is cyclopropyl. In some embodiments, at least one $R_5$ is cyclopropyl substituted with one or more $R_6$. In some embodiments, at least one $R_5$ is cyclopentyl. In some embodiments, at least one $R_5$ is cyclopropyl substituted with one or more $R_6$. In some embodiments, at least one $R_5$ is cyclohexyl. In some embodiments, at least one $R_5$ is cyclohexyl substituted with one or more $R_6$. In some embodiments, at least one $R_5$ is cycloheptyl. In some embodiments, at least one $R_5$ is cycloheptyl substituted with one or more $R_6$. In some embodiments, at least one $R_5$ is adamantyl. In some embodiments, at least one $R_5$ is adamantly substituted with one or more $R_6$. In some embodiments, at least one $R_5$ is aryl. In some embodiments, at least one $R_5$ is aryl substituted with one or more $R_6$. In some embodiments, at least one $R_5$ is phenyl. In some embodiments, at least one $R_5$ is phenyl substituted with one or more $R_6$. In some embodiments, at least one $R_5$ is 3- to 10-membered heterocyclyl. In some embodiments, at least one $R_5$ is 3- to 10-membered heterocyclyl substituted with one or more $R_6$. In some embodiments, at least one $R_5$ is tetrahydrofuranyl. In some embodiments, at least one $R_5$ is tetrahydrofuranyl substituted with one or more $R_6$. In some embodiments, at least one $R_5$ is piperidinyl. In some embodiments, at least one $R_5$ is piperidinyl substituted with one or more $R_6$. In some embodiments, at least one $R_5$ is piperazinyl. In some embodiments, at least one $R_5$ is piperazinyl substituted with one or more $R_6$. In some embodiments, at least one $R_5$ is morpholinyl. In some embodiments, at least one $R_5$ is morpholinyl substituted with one or more $R_6$. In some embodiments, at least one $R_5$ is heteroaryl. In some embodiments, at least one $R_5$ is heteroaryl substituted with one or more $R_6$. In some embodiments, at least one $R_5$ is pyrazolyl. In some embodiments, at least one $R_5$ is pyrazolyl substituted with one or more $R_6$. In some embodiments, at least one $R_5$ is pyridinyl. In some embodiments, at least one $R_5$ is pyridinyl substituted with one or more $R_6$. In some embodiments, at least one $R_5$ is benzimidazolyl. In some embodiments, at least one $R_5$ is benzimidazolyl substituted with one or more $R_6$. In some embodiments, at least one $R_5$ is dihydroisoquinolinyl. In some embodiments, at least one $R_5$ is dihydroisoquinolinyl substituted with one or more $R_6$. In some embodiments, at least one $R_5$ is tetrahydroquinolinyl. In some embodiments, at least one $R_5$ is tetrahydroquinolinyl substituted with one or more $R_6$.

In some embodiments, $R_4$ is —$N(R_5)_2$ and at least one $R_5$ is hydrogen.

In some embodiments, $R_4$ is —$N(R_5)_2$ and at least one $R_5$ is $C_1$-$C_6$ alkyl.

In some embodiments, $R_4$ is —$N(R_5)_2$ and at least one $R_5$ is $C_3$-$C_{10}$ cycloalkyl optionally substituted with one or more $R_6$.

In some embodiments, $R_4$ is —$N(R_5)_2$ and at least one $R_5$ is aryl optionally substituted with one or more $R_6$.

In some embodiments, $R_4$ is —$N(R_5)_2$ and at least one $R_5$ is phenyl optionally substituted with one or more $R_6$.

In some embodiments, $R_4$ is —$N(R_5)_2$ and at least one $R_5$ is 3- to 10-membered heterocyclyl optionally substituted with one or more $R_6$.

In some embodiments, $R_4$ is —$N(R_5)_2$ and at least one $R_5$ is heteroaryl optionally substituted with one or more $R_6$.

In some embodiments, $R_4$ is —$N(R_5)_2$ and at least one $R_5$ is pyridinyl optionally substituted with one or more $R_6$.

In some embodiments, two $R_5$, together with the nitrogen atom to which they are attached, come together to form 3- to 10-membered heterocyclyl. In some embodiments, two $R_5$, together with the nitrogen atom to which they are attached, come together to form 3- to 10-membered heterocyclyl substituted with one or more $R_6$. In some embodiments, two $R_5$, together with the nitrogen atom to which they are attached, come together to form heteroaryl.

In some embodiments, two $R_5$, together with the nitrogen atom to which they are attached, come together to form heteroaryl substituted with one or more $R_6$.

In some embodiments, at least one $R_6$ is —$C(O)R_7$. In some embodiments, at least one $R_6$ is —$C(O)NR_NR_7$. In some embodiments, at least one $R_6$ is —C(O)OR$_7$. In some embodiments, at least one $R_6$ is —NR$_N$R$_7$. In some embodiments, at least one $R_6$ is —NR$_N$C(O)R$_7$. In some embodiments, at least one $R_6$ is —OC(O)R$_7$. In some embodiments, at least one $R_6$ is —S(O)$_2$R$_7$. In some embodiments, at least one $R_6$ is halo. In some embodiments, at least one $R_6$ is fluoro. In some embodiments, at least one $R_6$ is chloro. In some embodiments, at least one $R_6$ is bromo. In some embodiments, at least one $R_6$ is iodo. In some embodiments, at least one $R_6$ is —OH. In some embodiments, at least one $R_6$ is —CN. In some embodiments, at least one $R_6$ is —$NO_3$. In some embodiments, at least one $R_6$ is $C_1$-$C_6$ alkyl. In some embodiments, at least one $R_6$ is $C_1$-$C_6$ alkyl substituted with one or more $R_7$. In some embodiments, at least one $R_6$ is methyl. In some embodiments, at least one $R_6$ is ethyl. In some embodiments, at least one $R_6$ is propyl. In some embodiments, at least one $R_6$ is isopropyl. In some embodiments, at least one $R_6$ is butyl. In some embodiments, at least one $R_6$ is isobutyl. In some embodiments, at least one $R_6$ is sec-butyl. In some embodiments, at least one $R_6$ is tert-butyl. In some embodiments, at least one $R_6$ is pentyl. In some embodiments, at least one $R_6$ is isopentyl. In some embodiments, at least one $R_6$ is sec-pentyl. In some embodiments, at least one $R_6$ is neopentyl. In some embodiments, at least one $R_6$ is hexyl. In some embodiments, at least one $R_6$ is isohexyl. In some embodiments, at least one $R_6$ is $C_2$-$C_6$ alkenyl. In some embodiments, at least one $R_6$ is $C_2$-$C_6$ alkenyl substituted with one or more $R_7$. In some embodiments, at least one $R_6$ is $C_2$-$C_6$ alkynyl. In some embodiments, at least one $R_6$ is $C_2$-$C_6$ alkynyl substituted with one or more $R_7$. In some embodiments, at least one $R_6$ is $C_1$-$C_6$ haloalkyl. In some embodiments, at least one $R_6$ is $C_1$-$C_6$ alkoxy. In some embodiments, at least one $R_6$ is $C_1$-$C_6$ haloalkoxy. In some embodiments, at least one $R_6$ is $C_3$-$C_{10}$ cycloalkyl. In some embodiments, at least one $R_6$ is $C_3$-$C_{10}$ cycloalkyl substituted with one or more $R_7$. In some embodiments, at least one $R_6$ is cyclopropyl. In some embodiments, at least one $R_6$ is cyclopropyl substituted with one or more $R_7$. In some embodiments, at least one $R_6$ is cyclopentyl. In some embodiments, at least one $R_6$ is cyclopropyl substituted with one or more $R_7$. In some embodiments, at least one $R_6$ is cyclohexyl. In some embodiments, at least one $R_6$ is cyclohexyl substituted with one or more $R_7$. In some embodiments, at least one $R_6$ is cycloheptyl. In some embodiments, at least one $R_6$ is cycloheptyl substituted with one or more $R_7$. In some embodiments, at least one $R_6$ is adamantyl. In some embodiments, at least one $R_6$ is adamantly substituted with one or more $R_7$. In some embodiments, at least one $R_6$ is aryl. In some embodiments, at least one $R_6$ is aryl substituted with one or more $R_7$. In some embodiments, at least one $R_6$ is phenyl. In some embodiments, at least one $R_6$ is phenyl substituted with one or more $R_7$. In some embodiments, at least one $R_6$ is 3- to 10-membered heterocyclyl. In some embodiments, at least one $R_6$ is 3- to 10-membered heterocyclyl substituted with one or more $R_7$. In some embodiments, at least one $R_6$ is tetrahydrofuranyl. In some embodiments, at least one $R_6$ is tetrahydrofuranyl substituted with one or more $R_7$. In some embodiments, at least one $R_6$ is piperidinyl. In some embodiments, at least one $R_6$ is piperidinyl substituted with one or more $R_7$. In some embodiments, at least one $R_6$ is piperazinyl. In some embodiments, at least one $R_6$ is piperazinyl substituted with one or more $R_7$. In some embodiments, at least one $R_6$ is morpholinyl. In some embodiments, at least one $R_6$ is morpholinyl substituted with one or more $R_7$. In some embodiments, at least one $R_6$ is heteroaryl. In some embodiments, at least one $R_6$ is heteroaryl substituted with one or more $R_7$. In some embodiments, at least one $R_6$ is pyrazolyl. In some embodiments, at least one $R_6$ is pyrazolyl substituted with one or more $R_7$. In some embodiments, at least one $R_6$ is pyridinyl. In some embodiments, at least one $R_6$ is pyridinyl substituted with one or more $R_7$. In some embodiments, at least one $R_6$ is benzimidazolyl. In some embodiments, at least one $R_6$ is benzimidazolyl substituted with one or more $R_7$. In some embodiments, at least one $R_6$ is dihydroisoquinolinyl. In some embodiments, at least one $R_6$ is dihydroisoquinolinyl substituted with one or more $R_7$. In some embodiments, at least one $R_6$ is tetrahydroquinolinyl. In some embodiments, at least one $R_6$ is tetrahydroquinolinyl substituted with one or more $R_7$.

In some embodiments, at least one $R_6$ is —NR$_N$R$_7$ and $R_N$ is hydrogen.

In some embodiments, at least one $R_6$ is selected from fluoro, chloro, —$CH_3$, —$CH(CH_3)_2$, —$C(CH_3)_3$, —$CHF_2$, —$CF_3$, —OH, —$OCH_3$, —$OCH_2CH_3$, —$OCF_3$,

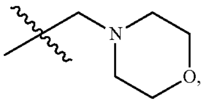
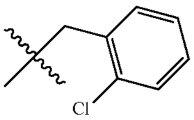
,
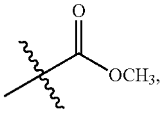
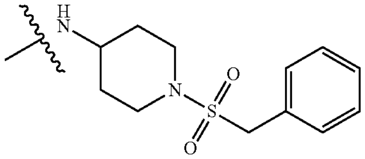
,
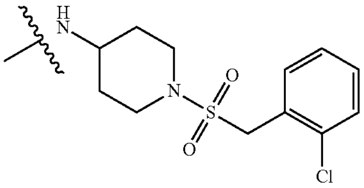
,
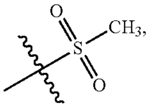
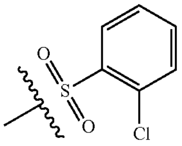
,
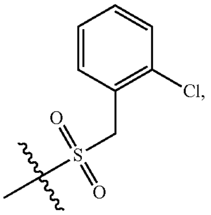
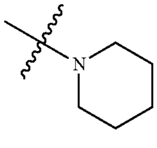
,
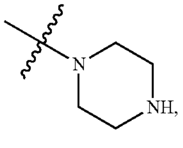
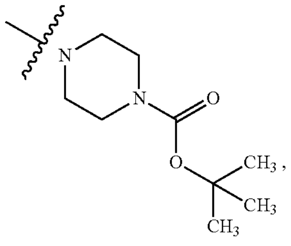
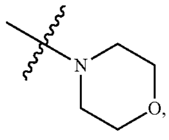

-continued

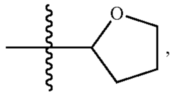, and 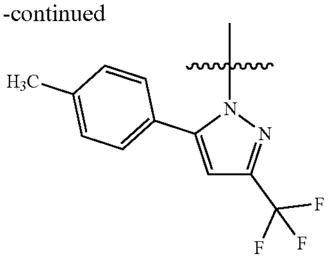.

In some embodiments, at least one $R_7$ is —C(O)O$R_8$. In some embodiments, at least one $R_7$ is halo. In some embodiments, at least one $R_7$ is fluoro. In some embodiments, at least one $R_7$ is chloro. In some embodiments, at least one $R_7$ is bromo. In some embodiments, at least one $R_7$ is iodo. In some embodiments, at least one $R_7$ is —OH. In some embodiments, at least one $R_7$ is —CN. In some embodiments, at least one $R_7$ is —$NO_3$. In some embodiments, at least one $R_7$ is $C_1$-$C_6$ alkyl. In some embodiments, at least one $R_7$ is $C_1$-$C_6$ alkyl substituted with one or more $R_8$. In some embodiments, at least one $R_7$ is methyl. In some embodiments, at least one $R_7$ is ethyl. In some embodiments, at least one $R_7$ is propyl. In some embodiments, at least one $R_7$ is isopropyl. In some embodiments, at least one $R_7$ is butyl. In some embodiments, at least one $R_7$ is isobutyl. In some embodiments, at least one $R_7$ is sec-butyl. In some embodiments, at least one $R_7$ is tert-butyl. In some embodiments, at least one $R_7$ is pentyl. In some embodiments, at least one $R_7$ is isopentyl. In some embodiments, at least one $R_7$ is sec-pentyl. In some embodiments, at least one $R_7$ is neopentyl. In some embodiments, at least one $R_7$ is hexyl. In some embodiments, at least one $R_7$ is isohexyl. In some embodiments, at least one $R_7$ is $C_2$-$C_6$ alkenyl. In some embodiments, at least one $R_7$ is $C_2$-$C_6$ alkenyl substituted with one or more $R_8$. In some embodiments, at least one $R_7$ is $C_2$-$C_6$ alkynyl. In some embodiments, at least one $R_7$ is $C_2$-$C_6$ alkynyl substituted with one or more $R_8$. In some embodiments, at least one $R_7$ is $C_1$-$C_6$ haloalkyl. In some embodiments, at least one $R_7$ is $C_1$-$C_6$ alkoxy. In some embodiments, at least one $R_7$ is $C_1$-$C_6$ haloalkoxy. In some embodiments, at least one $R_7$ is $C_3$-$C_{10}$ cycloalkyl. In some embodiments, at least one $R_7$ is $C_3$-$C_{10}$ cycloalkyl substituted with one or more $R_8$. In some embodiments, at least one $R_7$ is aryl. In some embodiments, at least one $R_7$ is aryl substituted with one or more $R_8$. In some embodiments, at least one $R_7$ is phenyl. In some embodiments, at least one $R_7$ is phenyl substituted with one or more $R_8$. In some embodiments, at least one $R_7$ is 3- to 10-membered heterocyclyl. In some embodiments, at least one $R_7$ is 3- to 10-membered heterocyclyl substituted with one or more $R_8$. In some embodiments, at least one $R_7$ is heteroaryl. In some embodiments, at least one $R_7$ is heteroaryl substituted with one or more $R_8$.

In some embodiments, at least one $R_8$ is —S(O)$R_9$. In some embodiments, at least one $R_8$ is halo. In some embodiments, at least one $R_8$ is fluoro. In some embodiments, at least one $R_8$ is chloro. In some embodiments, at least one $R_8$ is bromo. In some embodiments, at least one $R_8$ is iodo. In some embodiments, at least one $R_8$ is —OH. In some embodiments, at least one $R_8$ is —CN. In some embodiments, at least one $R_8$ is —$NO_3$. In some embodiments, at least one $R_8$ is $C_1$-$C_6$ alkyl. In some embodiments, at least one $R_8$ is $C_1$-$C_6$ alkyl substituted with one or more $R_9$. In some embodiments, at least one $R_8$ is methyl. In some embodiments, at least one $R_8$ is ethyl. In some embodiments, at least one $R_8$ is propyl. In some embodiments, at least one $R_8$ is isopropyl. In some embodiments, at least one $R_8$ is butyl. In some embodiments, at least one $R_8$ is isobutyl. In some embodiments, at least one $R_8$ is sec-butyl. In some embodiments, at least one $R_8$ is tert-butyl. In some embodiments, at least one $R_8$ is pentyl. In some embodiments, at least one $R_8$ is isopentyl. In some embodiments, at least one $R_8$ is sec-pentyl. In some embodiments, at least one $R_8$ is neopentyl. In some embodiments, at least one $R_8$ is hexyl. In some embodiments, at least one $R_8$ is isohexyl. In some embodiments, at least one $R_8$ is $C_2$-$C_6$ alkenyl. In some embodiments, at least one $R_8$ is $C_2$-$C_6$ alkenyl substituted with one or more $R_9$. In some embodiments, at least one $R_8$ is $C_2$-$C_6$ alkynyl. In some embodiments, at least one $R_8$ is $C_2$-$C_6$ alkynyl substituted with one or more $R_9$. In some embodiments, at least one $R_8$ is $C_1$-$C_6$ haloalkyl. In some embodiments, at least one $R_8$ is $C_1$-$C_6$ alkoxy. In some embodiments, at least one $R_8$ is $C_1$-$C_6$ haloalkoxy. In some embodiments, at least one $R_8$ is $C_3$-$C_{10}$ cycloalkyl. In some embodiments, at least one $R_8$ is $C_3$-$C_{10}$ cycloalkyl substituted with one or more $R_9$. In some embodiments, at least one $R_8$ is aryl. In some embodiments, at least one $R_8$ is aryl substituted with one or more $R_9$. In some embodiments, at least one $R_8$ is phenyl. In some embodiments, at least one $R_8$ is phenyl substituted with one or more $R_9$. In some embodiments, at least one $R_8$ is 3- to 10-membered heterocyclyl. In some embodiments, at least one $R_8$ is 3- to 10-membered heterocyclyl substituted with one or more $R_9$. In some embodiments, at least one $R_8$ is heteroaryl. In some embodiments, at least one $R_8$ is heteroaryl substituted with one or more $R_9$.

In some embodiments, at least one $R_9$ is halo. In some embodiments, at least one $R_9$ is fluoro. In some embodiments, at least one $R_9$ is chloro. In some embodiments, at least one $R_9$ is bromo. In some embodiments, at least one $R_9$ is iodo. In some embodiments, at least one $R_9$ is —OH. In some embodiments, at least one $R_9$ is —CN. In some embodiments, at least one $R_9$ is —$NO_3$. In some embodiments, at least one $R_9$ is $C_1$-$C_6$ alkyl. In some embodiments, at least one $R_9$ is $C_1$-$C_6$ alkyl substituted with one or more $R_{10}$. In some embodiments, at least one $R_9$ is methyl. In some embodiments, at least one $R_9$ is ethyl. In some embodiments, at least one $R_9$ is propyl. In some embodiments, at least one $R_9$ is isopropyl. In some embodiments, at least one $R_9$ is butyl. In some embodiments, at least one $R_9$ is isobutyl. In some embodiments, at least one $R_9$ is sec-butyl. In some embodiments, at least one $R_9$ is tert-butyl. In some embodiments, at least one $R_9$ is pentyl. In some embodiments, at least one $R_9$ is isopentyl. In some embodiments, at least one $R_9$ is sec-pentyl. In some embodiments, at least one $R_9$ is neopentyl. In some embodiments, at least one $R_9$ is hexyl. In some embodiments, at least one $R_9$ is isohexyl. In some embodiments, at least one $R_9$ is $C_2$-$C_6$ alkenyl. In some embodiments, at least one $R_9$ is $C_2$-$C_6$ alkenyl substituted with one or more $R_{10}$. In some embodiments, at least one $R_9$ is $C_2$-$C_6$ alkynyl. In some embodiments, at least one $R_9$ is $C_2$-$C_6$ alkynyl substituted with one or more $R_{10}$. In some embodiments, at least one $R_9$ is $C_1$-$C_6$ haloalkyl. In some embodiments, at least one $R_9$ is $C_1$-$C_6$ alkoxy. In some embodiments, at least one $R_9$ is $C_1$-$C_6$ haloalkoxy. In some embodiments, at least one $R_9$ is $C_3$-$C_{10}$ cycloalkyl. In some embodiments, at least one $R_9$ is $C_3$-$C_{10}$ cycloalkyl substituted with one or more $R_{10}$. In some embodiments, at least one $R_9$ is aryl. In some embodiments, at least one $R_9$ is aryl substituted with one or more $R_{10}$. In some embodiments, at least one $R_9$ is phenyl. In some embodiments, at least one $R_9$ is phenyl substituted with one or more $R_{10}$. In some embodiments, at least one $R_9$ is 3- to 10-membered heterocyclyl. In some embodiments, at least one $R_9$ is 3- to 10-membered heterocyclyl substituted with one or more $R_{10}$. In some embodiments, at least one $R_9$ is heteroaryl. In some embodiments, at least one $R_9$ is heteroaryl substituted with one or more $R_{10}$.

In some embodiments, at least one $R_{10}$ is halo. In some embodiments, at least one $R_{10}$ is fluoro. In some embodiments, at least one $R_{10}$ is chloro. In some embodiments, at least one $R_{10}$ is bromo. In some embodiments, at least one $R_{10}$ is iodo. In some embodiments, at least one $R_{10}$ is —OH. In some embodiments, at least one $R_{10}$ is —CN. In some embodiments, at least one $R_{10}$ is —$NO_3$. In some embodiments, at least one $R_{10}$ is $C_1$-$C_6$ alkyl. In some embodiments, at least one $R_{10}$ is $C_1$-$C_6$ alkyl substituted with one or more $R_{11}$. In some embodiments, at least one $R_{10}$ is methyl. In some embodiments, at least one $R_{10}$ is ethyl. In some embodiments, at least one $R_{10}$ is propyl. In some embodiments, at least one $R_{10}$ is isopropyl. In some embodiments, at least one $R_{10}$ is butyl. In some embodiments, at least one $R_{10}$ is isobutyl. In some embodiments, at least one $R_{10}$ is sec-butyl. In some embodiments, at least one $R_{10}$ is tert-butyl. In some embodiments, at least one $R_{10}$ is pentyl. In some embodiments, at least one $R_{10}$ is isopentyl. In some embodiments, at least one $R_{10}$ is sec-pentyl. In some embodiments, at least one $R_{10}$ is neopentyl. In some embodiments, at least one $R_{10}$ is hexyl. In some embodiments, at least one $R_{10}$ is isohexyl. In some embodiments, at least one $R_{10}$ is $C_2$-$C_6$ alkenyl. In some embodiments, at least one $R_{10}$ is $C_2$-$C_6$ alkenyl substituted with one or more Ru. In some embodiments, at least one $R_{10}$ is $C_2$-$C_6$ alkynyl. In some embodiments, at least one $R_{10}$ is $C_2$-$C_6$ alkynyl substituted with one or more Ru. In some embodiments, at least one $R_{10}$ is $C_1$-$C_6$ haloalkyl. In some embodiments, at least one $R_{10}$ is $C_1$-$C_6$ alkoxy. In some embodiments, at least one $R_{10}$ is $C_1$-$C_6$ haloalkoxy. In some embodiments, at least one $R_{10}$ is $C_3$-$C_{10}$ cycloalkyl. In some embodiments, at least one $R_{10}$ is $C_3$-$C_{10}$ cycloalkyl substituted with one or more Ru. In some embodiments, at least one $R_{10}$ is aryl. In some embodiments, at least one $R_{10}$ is aryl substituted with one or more $R_{11}$. In some embodiments, at least one $R_{10}$ is phenyl. In some embodiments, at least one $R_{10}$ is phenyl substituted with one or more Ru. In some embodiments, at least one $R_{10}$ is 3- to 10-membered heterocyclyl. In some embodiments, at least one $R_{10}$ is 3- to 10-membered heterocyclyl substituted with one or more $R_1$. In some embodiments, at least one $R_{10}$ is heteroaryl. In some embodiments, at least one $R_{10}$ is heteroaryl substituted with one or more Ru.

In some embodiments, at least one $R_{10}$ is halo. In some embodiments, at least one $R_{10}$ is fluoro. In some embodiments, at least one $R_{10}$ is chloro. In some embodiments, at least one $R_{10}$ is bromo. In some embodiments, at least one $R_{10}$ is iodo. In some embodiments, at least one $R_{10}$ is —OH. In some embodiments, at least one $R_{10}$ is —CN. In some embodiments, at least one $R_{10}$ is —$NO_3$. In some embodiments, at least one $R_{10}$ is $C_1$-$C_6$ alkyl. In some embodiments, at least one $R_{10}$ is $C_1$-$C_6$ alkyl substituted with one or more $R_{11}$. In some embodiments, at least one $R_{10}$ is methyl. In some embodiments, at least one $R_{10}$ is ethyl. In some embodiments, at least one $R_{10}$ is propyl. In some embodiments, at least one $R_{10}$ is isopropyl. In some embodiments, at least one $R_{10}$ is butyl. In some embodiments, at least one $R_{10}$ is isobutyl. In some embodiments, at least one $R_{10}$ is sec-butyl. In some embodiments, at least one $R_{10}$ is tert-butyl. In some embodiments, at least one $R_{10}$ is pentyl. In some embodiments, at least one $R_{10}$ is isopentyl. In some embodiments, at least one $R_{10}$ is sec-pentyl. In some embodiments, at least one $R_{10}$ is neopentyl. In some embodiments, at least one $R_{10}$ is hexyl. In some embodiments, at least one $R_{10}$ is isohexyl. In some embodiments, at least one $R_{10}$ is $C_2$-$C_6$ alkenyl. In some embodiments, at least one $R_{10}$ is $C_2$-$C_6$ alkenyl substituted with one or more Ru. In some embodiments, at least one $R_{10}$ is $C_2$-$C_6$ alkynyl. In some embodiments, at least one $R_{10}$ is $C_2$-$C_6$ alkynyl substituted with one or more Ru. In some embodiments, at least one $R_{10}$ is $C_1$-$C_6$ haloalkyl. In some embodiments, at least one $R_{10}$ is $C_1$-$C_6$ alkoxy. In some embodiments, at least one $R_{10}$ is $C_1$-$C_6$ haloalkoxy.

In some embodiments, $R_N$ is hydrogen. In some embodiments, $R_N$ is deuterium. In some embodiments, $R_N$ is $C_1$-$C_6$ alkyl. In some embodiments, $R_N$ is methyl. In some embodiments, $R_N$ is ethyl. In some embodiments, $R_N$ is propyl. In some embodiments, $R_N$ is isopropyl. In some embodiments, $R_N$ is butyl. In some embodiments, $R_N$ is isobutyl. In some embodiments, $R_N$ is sec-butyl. In some embodiments, $R_N$ is tert-butyl. In some embodiments, $R_N$ is pentyl. In some embodiments, $R_N$ is isopentyl. In some embodiments, $R_N$ is sec-pentyl. In some embodiments, $R_N$ is neopentyl. In some embodiments, $R_N$ is hexyl. In some embodiments, $R_N$ is isohexyl. In some embodiments, $R_N$ is $C_2$-$C_6$ alkenyl. In some embodiments, $R_N$ is $C_2$-$C_6$ alkynyl.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is aryl.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is aryl substituted with $C_1$-$C_6$ alkoxy.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is $C_3$-$C_{10}$ cycloalkyl.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is $C_1$-$C_6$ alkyl substituted with 3- to 10-membered heterocyclyl.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is $C_1$-$C_6$ alkyl substituted with $C_1$-$C_6$ alkoxy.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is $C_1$-$C_6$ alkyl substituted with aryl.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is $C_1$-$C_6$ alkyl.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is heterocyclyl, substituted with $C_1$-$C_6$ alkyl.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is an optionally substituted $C_3$-$C_{10}$ cycloalkyl.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is a 1-, 2-, 3-, or 4-piperidine optionally substituted with $C_1$-$C_6$ alkyl.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is 4-piperidine substituted on N with a $C_1$-$C_6$ alkyl carboxylate.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is a $C_1$-$C_6$ alkylene substituted with 1-(2-azaspiro[4.5] decan-4-yl) substituent.

In some embodiments, L is —$NR_LC(O)$—, $R_L$ is hydrogen, $R_1$ is hydrogen, each $R_2$ is hydrogen, each $R_3$ is hydrogen, $R_4$ is —$N(R_5)_2$, one $R_5$ is hydrogen, and the other $R_5$ is a spirocyclic heterocyclyl, optionally substituted with $C_1$-$C_6$ alkyl or a $C_1$-$C_6$ alkyl carboxylate.

Non-limiting illustrative compounds of the present disclosure include:

5-(3-fluoro-5-hydroxy-3'-methoxybiphenyl-4-yl)-1,2,5-thiadiazolidin-3-one 1,1-dioxide;
5-(3,3'-difluoro-5-hydroxybiphenyl-4-yl)-1,2,5-thiadiazolidin-3-one 1,1-dioxide;
5-(3-fluoro-5-hydroxy-4'-methoxybiphenyl-4-yl)-1,2,5-thiadiazolidin-3-one 1,1-dioxide;
5-(3,3',5'-trifluoro-5-hydroxybiphenyl-4-yl)-1,2,5-thiadiazolidin-3-one 1,1-dioxide;
5-(2'-ethoxy-3-fluoro-5-hydroxybiphenyl-4-yl)-1,2,5-thiadiazolidin-3-one 1,1-dioxide;
5-(3-fluoro-5-hydroxy-2'-methylbiphenyl-4-yl)-1,2,5-thiadiazolidin-3-one 1,1-dioxide;
5-(2',3-difluoro-5-hydroxybiphenyl-4-yl)-1,2,5-thiadiazolidin-3-one 1,1-dioxide;
5-(3,4'-difluoro-5-hydroxybiphenyl-4-yl)-1,2,5-thiadiazolidin-3-one 1,1-dioxide;
5-(3-fluoro-5-hydroxy-3'-methylbiphenyl-4-yl)-1,2,5-thiadiazolidin-3-one 1,1-dioxide;
5-(3-fluoro-5-hydroxy-4'-methylbiphenyl-4-yl)-1,2,5-thiadiazolidin-3-one 1,1-dioxide;
5-[3'-({1-[(2-chlorobenzyl)sulfonyl]piperidin-4-yl}amino)-3-fluoro-5-hydroxybiphenyl-4-yl]-1,2,5-thiadiazolidin-3-one 1,1-dioxide;
5-(3'-{[1-(benzylsulfonyl)piperidin-4-yl]amino}-3-fluoro-5-hydroxybiphenyl-4-yl)-1,2,5-thiadiazolidin-3-one 1,1-dioxide;
N-[4-(1,1-dioxido-4-oxo-1,2,5-thiadiazolidin-2-yl)-3-fluoro-5-hydroxyphenyl]benzamide;
N-[4-(1,1-dioxido-4-oxo-1,2,5-thiadiazolidin-2-yl)-3-fluoro-5-hydroxyphenyl]-3,4-dimethoxybenzamide;
N-[4-(1,1-dioxido-4-oxo-1,2,5-thiadiazolidin-2-yl)-3-fluoro-5-hydroxyphenyl]-4-methoxybenzamide;
4-tert-butyl-N-[4-(1,1-dioxido-4-oxo-1,2,5-thiadiazolidin-2-yl)-3-fluoro-5-hydroxyphenyl]benzamide;
N-[4-(1,1-dioxido-4-oxo-1,2,5-thiadiazolidin-2-yl)-3-fluoro-5-hydroxyphenyl]benzenesulfonamide;
N-[4-(1,1-dioxido-4-oxo-1,2,5-thiadiazolidin-2-yl)-3-fluoro-5-hydroxyphenyl]-4-methylbenzenesulfonamide;
N-[4-(1,1-dioxido-4-oxo-1,2,5-thiadiazolidin-2-yl)-3-fluoro-5-hydroxyphenyl]-4-[5-(4-methylphenyl)-3-(trifluoromethyl)-1H-pyrazol-1-yl]benzenesulfonamide;
N-[4-(1,1-dioxido-4-oxo-1,2,5-thiadiazolidin-2-yl)-3-fluoro-5-hydroxyphenyl]-4-fluorobenzenesulfonamide;
N-[4-(1,1-dioxido-4-oxo-1,2,5-thiadiazolidin-2-yl)-3-fluoro-5-hydroxyphenyl]-2-fluorobenzenesulfonamide;
N-[4-(1,1-dioxido-4-oxo-1,2,5-thiadiazolidin-2-yl)-3-fluoro-5-hydroxyphenyl]-3-methylbenzenesulfonamide;
N-[4-(1,1-dioxido-4-oxo-1,2,5-thiadiazolidin-2-yl)-3-fluoro-5-hydroxyphenyl]-2-methylbenzenesulfonamide;
4-tert-butyl-N-[4-(1,1-dioxido-4-oxo-1,2,5-thiadiazolidin-2-yl)-3-fluoro-5-hydroxyphenyl]benzenesulfonamide;
N-[4-(1,1-dioxido-4-oxo-1,2,5-thiadiazolidin-2-yl)-3-fluoro-5-hydroxyphenyl]-4-methoxybenzenesulfonamide;
N-[4-(1,1-dioxido-4-oxo-1,2,5-thiadiazolidin-2-yl)-3-fluoro-5-hydroxyphenyl]-3,4-dimethoxybenzenesulfonamide;
1-(difluoromethyl)-N-[4-(1,1-dioxido-4-oxo-1,2,5-thiadiazolidin-2-yl)-3-fluoro-5-hydroxyphenyl]-5-methyl-TH-pyrazole-4-sulfonamide;
N-[4-(1,1-dioxido-4-oxo-1,2,5-thiadiazolidin-2-yl)-3-fluoro-5-hydroxyphenyl]butane-1-sulfonamide;
N-[4-(1,1-dioxido-4-oxo-1,2,5-thiadiazolidin-2-yl)-3-fluoro-5-hydroxyphenyl]-N'-phenylsulfuric diamide;
N-{1-[(2-chlorobenzyl)sulfonyl]piperidin-4-yl}-N'-[4-(1,1-dioxido-4-oxo-1,2,5-thiadiazolidin-2-yl)-3-fluoro-5-hydroxyphenyl]sulfuric diamide;
N'-[4-(1,1-dioxido-4-oxo-1,2,5-thiadiazolidin-2-yl)-3-fluoro-5-hydroxyphenyl]-N-methyl-N-phenylsulfuric diamide;
N-cyclohexyl-N'-[4-(1,1-dioxido-4-oxo-1,2,5-thiadiazolidin-2-yl)-3-fluoro-5-hydroxyphenyl]-N-methylsulfuric diamide;
N-(3-chlorophenyl)-N'-[4-(1,1-dioxido-4-oxo-1,2,5-thiadiazolidin-2-yl)-3-fluoro-5-hydroxyphenyl]-N-methylsulfuric diamide;
N-(3,4-dimethoxybenzyl)-N'-[4-(1,1-dioxido-4-oxo-1,2,5-thiadiazolidin-2-yl)-3-fluoro-5-hydroxyphenyl]-N-phenylsulfuric diamide;
1-[4-(1,1-dioxido-4-oxo-1,2,5-thiadiazolidin-2-yl)-3-fluoro-5-hydroxyphenyl]-3-phenylurea;
1-[4-(1,1-dioxido-4-oxo-1,2,5-thiadiazolidin-2-yl)-3-fluoro-5-hydroxyphenyl]-3-(4-methylphenyl)urea;
1-[4-(1,1-dioxido-4-oxo-1,2,5-thiadiazolidin-2-yl)-3-fluoro-5-hydroxyphenyl]-3-(4-methoxyphenyl)urea;
1-[4-(1,1-dioxido-4-oxo-1,2,5-thiadiazolidin-2-yl)-3-fluoro-5-hydroxyphenyl]-3-[3-(trifluoromethyl)phenyl]urea;
1-[4-(1,1-dioxido-4-oxo-1,2,5-thiadiazolidin-2-yl)-3-fluoro-5-hydroxyphenyl]-3-(2-methylphenyl)urea;
1-[4-(1,1-dioxido-4-oxo-1,2,5-thiadiazolidin-2-yl)-3-fluoro-5-hydroxyphenyl]-3-(2-methoxyphenyl)urea;
1-[4-(1,1-dioxido-4-oxo-1,2,5-thiadiazolidin-2-yl)-3-fluoro-5-hydroxyphenyl]-3-[4-(trifluoromethyl)phenyl]urea;
1-[4-(1,1-dioxido-4-oxo-1,2,5-thiadiazolidin-2-yl)-3-fluoro-5-hydroxyphenyl]-3-(3-methylphenyl)urea;
1-[4-(1,1-dioxido-4-oxo-1,2,5-thiadiazolidin-2-yl)-3-fluoro-5-hydroxyphenyl]-3-(3-methoxyphenyl)urea;
1-[4-(1,1-dioxido-4-oxo-1,2,5-thiadiazolidin-2-yl)-3-fluoro-5-hydroxyphenyl]-3-pyridin-4-ylurea;
1-{1-[(2-chlorobenzyl)sulfonyl]piperidin-4-yl}-3-[4-(1,1-dioxido-4-oxo-1,2,5-thiadiazolidin-2-yl)-3-fluoro-5-hydroxyphenyl]urea;
1-(3-chlorophenyl)-3-[4-(1,1-dioxido-4-oxo-1,2,5-thiadiazolidin-2-yl)-3-fluoro-5-hydroxyphenyl]urea;
1-(4-chlorophenyl)-3-[4-(1,1-dioxido-4-oxo-1,2,5-thiadiazolidin-2-yl)-3-fluoro-5-hydroxyphenyl]urea;
1-(2-chlorophenyl)-3-[4-(1,1-dioxido-4-oxo-1,2,5-thiadiazolidin-2-yl)-3-fluoro-5-hydroxyphenyl]urea;
1-(1H-benzimidazol-5-yl)-3-[4-(1,1-dioxido-4-oxo-1,2,5-thiadiazolidin-2-yl)-3-fluoro-5-hydroxyphenyl]urea;
1-(3-tert-butyl-1-methyl-1H-pyrazol-5-yl)-3-[4-(1,1-dioxido-4-oxo-1,2,5-thiadiazolidin-2-yl)-3-fluoro-5-hydroxyphenyl]urea;

1-{1-[(2-chlorophenyl)sulfonyl]piperidin-4-yl}-3-[4-(1,1-dioxido-4-oxo-1,2,5-thiadiazolidin-2-yl)-3-fluoro-5-hydroxyphenyl]urea;

1-[4-(1,1-dioxido-4-oxo-1,2,5-thiadiazolidin-2-yl)-3-fluoro-5-hydroxyphenyl]-3-pyridin-3-ylurea;

1-[4-(1,1-dioxido-4-oxo-1,2,5-thiadiazolidin-2-yl)-3-fluoro-5-hydroxyphenyl]-3-(4-fluorophenyl)urea;

1-[4-(1,1-dioxido-4-oxo-1,2,5-thiadiazolidin-2-yl)-3-fluoro-5-hydroxyphenyl]-3-(3-fluorophenyl)urea;

1-[4-(1,1-dioxido-4-oxo-1,2,5-thiadiazolidin-2-yl)-3-fluoro-5-hydroxyphenyl]-3-[2-(trifluoromethyl)phenyl]urea;

1-cyclohexyl-3-[4-(1,1-dioxido-4-oxo-1,2,5-thiadiazolidin-2-yl)-3-fluoro-5-hydroxyphenyl]urea;

1-[4-(1,1-dioxido-4-oxo-1,2,5-thiadiazolidin-2-yl)-3-fluoro-5-hydroxyphenyl]-3-(tetrahydrofuran-2-ylmethyl)urea;

1-[4-(1,1-dioxido-4-oxo-1,2,5-thiadiazolidin-2-yl)-3-fluoro-5-hydroxyphenyl]-3-(3-methoxypropyl)urea;

1-(3,4-dimethoxyphenyl)-3-[4-(1,1-dioxido-4-oxo-1,2,5-thiadiazolidin-2-yl)-3-fluoro-5-hydroxyphenyl]urea;

1-benzyl-3-[4-(1,1-dioxido-4-oxo-1,2,5-thiadiazolidin-2-yl)-3-fluoro-5-hydroxyphenyl]urea;

1-[4-(1,1-dioxido-4-oxo-1,2,5-thiadiazolidin-2-yl)-3-fluoro-5-hydroxyphenyl]-3-tricyclo[3.3.1.1$^{3,7}$]dec-1-ylurea;

1-[4-(1,1-dioxido-4-oxo-1,2,5-thiadiazolidin-2-yl)-3-fluoro-5-hydroxyphenyl]-3-(3-methylbutyl)urea;

1-[4-(1,1-dioxido-4-oxo-1,2,5-thiadiazolidin-2-yl)-3-fluoro-5-hydroxyphenyl]-3-(4-methoxybenzyl)urea;

1-[1-(2-chlorobenzyl)-1H-pyrazol-4-yl]-3-[4-(1,1-dioxido-4-oxo-1,2,5-thiadiazolidin-2-yl)-3-fluoro-5-hydroxyphenyl]urea;

1-[4-(1,1-dioxido-4-oxo-1,2,5-thiadiazolidin-2-yl)-3-fluoro-5-hydroxyphenyl]-3-[4-(morpholin-4-yl)phenyl]urea;

tert-butyl 4-[4-({[4-(1,1-dioxido-4-oxo-1,2,5-thiadiazolidin-2-yl)-3-fluoro-5-hydroxyphenyl]carbamoyl}amino)phenyl]piperazine-1-carboxylate;

1-[4-(1,1-dioxido-4-oxo-1,2,5-thiadiazolidin-2-yl)-3-fluoro-5-hydroxyphenyl]-3-[4-(piperazin-1-yl)phenyl]urea hydrochloride;

1-[4-(1,1-dioxido-4-oxo-1,2,5-thiadiazolidin-2-yl)-3-fluoro-5-hydroxyphenyl]-3-[4-methoxy-3-(trifluoromethyl)phenyl]urea;

1-[4-(1,1-dioxido-4-oxo-1,2,5-thiadiazolidin-2-yl)-3-fluoro-5-hydroxyphenyl]-3-[4-(methylsulfonyl)phenyl]urea;

1-[4-(1,1-dioxido-4-oxo-1,2,5-thiadiazolidin-2-yl)-3-fluoro-5-hydroxyphenyl]-3-[4-(propan-2-yl)phenyl]urea;

1-[4-(1,1-dioxido-4-oxo-1,2,5-thiadiazolidin-2-yl)-3-fluoro-5-hydroxyphenyl]-3-[4-(trifluoromethoxy)phenyl]urea;

1-[4-(1,1-dioxido-4-oxo-1,2,5-thiadiazolidin-2-yl)-3-fluoro-5-hydroxyphenyl]-3-(1-methylpiperidin-4-yl)urea;

N-[4-(1,1-dioxido-4-oxo-1,2,5-thiadiazolidin-2-yl)-3-fluoro-5-hydroxyphenyl]-3,4-dihydroquinoline-1(2H)-carboxamide;

N-[4-(1,1-dioxido-4-oxo-1,2,5-thiadiazolidin-2-yl)-3-fluoro-5-hydroxyphenyl]-3,4-dihydroisoquinoline-2(1H)-carboxamide;

(3S)—N-[4-(1,1-dioxido-4-oxo-1,2,5-thiadiazolidin-2-yl)-3-fluoro-5-hydroxyphenyl]-3-(morpholin-4-ylmethyl)-3,4-dihydroisoquinoline-2(1H)-carboxamide;

3-[4-(1,1-dioxido-4-oxo-1,2,5-thiadiazolidin-2-yl)-3-fluoro-5-hydroxyphenyl]-1-methyl-1-phenylurea;

1-[4-(1,1-dioxido-4-oxo-1,2,5-thiadiazolidin-2-yl)-3-fluoro-5-hydroxyphenyl]-3-(1-methyl-1,2,3,4-tetrahydroquinolin-7-yl)urea;

N-[4-(1,1-dioxido-4-oxo-1,2,5-thiadiazolidin-2-yl)-3-fluoro-5-hydroxyphenyl]pyridine-3-sulfonamide;

4-chloro-N-[4-(1,1-dioxido-4-oxo-1,2,5-thiadiazolidin-2-yl)-3-fluoro-5-hydroxyphenyl]benzenesulfonamide;

methyl 2-{[4-(1,1-dioxido-4-oxo-1,2,5-thiadiazolidin-2-yl)-3-fluoro-5-hydroxyphenyl]sulfamoyl}benzoate;

N-[4-(1,1-dioxido-4-oxo-1,2,5-thiadiazolidin-2-yl)-3-fluoro-5-hydroxyphenyl]-3-fluorobenzenesulfonamide;

3-chloro-N-[4-(1,1-dioxido-4-oxo-1,2,5-thiadiazolidin-2-yl)-3-fluoro-5-hydroxyphenyl]benzenesulfonamide;

N-[4-(1,1-dioxido-4-oxo-1,2,5-thiadiazolidin-2-yl)-3-fluoro-5-hydroxyphenyl]-4-(trifluoromethyl)benzenesulfonamide;

N-[4-(1,1-dioxido-4-oxo-1,2,5-thiadiazolidin-2-yl)-3-fluoro-5-hydroxyphenyl]-3-(trifluoromethyl)benzenesulfonamide;

N-[4-(1,1-dioxido-4-oxo-1,2,5-thiadiazolidin-2-yl)-3-fluoro-5-hydroxyphenyl]-1-phenylmethanesulfonamide;

N-[4-(1,1-dioxido-4-oxo-1,2,5-thiadiazolidin-2-yl)-3-fluoro-5-hydroxyphenyl]cyclopropanesulfonamide;

N-[4-(1,1-dioxido-4-oxo-1,2,5-thiadiazolidin-2-yl)-3-fluoro-5-hydroxyphenyl]propane-2-sulfonamide;

1-cyclopentyl-3-[4-(1,1-dioxido-4-oxo-1,2,5-thiadiazolidin-2-yl)-3-fluoro-5-hydroxyphenyl]urea;

1-[4-(1,1-dioxido-4-oxo-1,2,5-thiadiazolidin-2-yl)-3-fluoro-5-hydroxyphenyl]-3-(4-methylcyclohexyl)urea;

1-(4-tert-butylcyclohexyl)-3-[4-(1,1-dioxido-4-oxo-1,2,5-thiadiazolidin-2-yl)-3-fluoro-5-hydroxyphenyl]urea;

1-[4-(1,1-dioxido-4-oxo-1,2,5-thiadiazolidin-2-yl)-3-fluoro-5-hydroxyphenyl]-3-(trans-4-hydroxycyclohexyl)urea;

1-cycloheptyl-3-[4-(1,1-dioxido-4-oxo-1,2,5-thiadiazolidin-2-yl)-3-fluoro-5-hydroxyphenyl]urea;

1-[4-(1,1-dioxido-4-oxo-1,2,5-thiadiazolidin-2-yl)-3-fluoro-5-hydroxyphenyl]-3-(2-fluorophenyl)urea 1-[4-(1,1-dioxido-4-oxo-1,2,5-thiadiazolidin-2-yl)-3-fluoro-5-hydroxyphenyl]-3-[3-(piperidin-1-yl)propyl]urea;

1-[4-(1,1-dioxido-4-oxo-1,2,5-thiadiazolidin-2-yl)-3-fluoro-5-hydroxyphenyl]-3-[3-(morpholin-4-yl)propyl]urea;

N'-[4-(1,1-dioxido-4-oxo-1,2,5-thiadiazolidin-2-yl)-3-fluoro-5-hydroxyphenyl]-N-(3-fluorophenyl)-N-methylsulfuric diamide; and N'-[4-(1,1-dioxido-4-oxo-1,2,5-thiadiazolidin-2-yl)-3-fluoro-5-hydroxyphenyl]-N-(4-fluorophenyl)-N-methylsulfuric diamide;

tert-butyl 4-[[3-fluoro-5-hydroxy-4-(1,1,4-trioxo-1,2,5-thiadiazolidin-2-yl)phenyl]carbamoyl-amino]piperidine-1-carboxylate;

1-[3-fluoro-5-hydroxy-4-(1,1,4-trioxo-1,2,5-thiadiazolidin-2-yl)phenyl]-3-(4-piperidyl)urea;

1-(2-azaspiro[4.5]decan-4-ylmethyl)-3-[3-fluoro-5-hydroxy-4-(1,1,4-trioxo-1,2,5-thiadiazolidin-2-yl)phenyl]urea;

tert-butyl 4-[[[3-fluoro-5-hydroxy-4-(1,1,4-trioxo-1,2,5-thiadiazolidin-2-yl)phenyl]carbamoyl-amino]methyl]-2-azaspiro[4.5]decane-2-carboxylate;

1-[3-fluoro-5-hydroxy-4-(1,1,4-trioxo-1,2,5-thiadiazolidin-2-yl)phenyl]-3-[(2-isopentyl-2-azaspiro[4.5]decan-4-yl)methyl]urea;

1-[3-fluoro-5-hydroxy-4-(1,1,4-trioxo-1,2,5-thiadiazolidin-2-yl)phenyl]-3-[(1S)-2-hydroxy-1-phenylethyl]urea;

1-[3-fluoro-5-hydroxy-4-(1,1,4-trioxo-1,2,5-thiadiazolidin-2-yl)phenyl]-3-(3-piperidyl)urea;

1-[3-fluoro-5-hydroxy-4-(1,1,4-trioxo-1,2,5-thiadiazolidin-2-yl)phenyl]-3-(2-hydroxycyclohexyl)urea;

tert-butyl 3-[[3-fluoro-5-hydroxy-4-(1,1,4-trioxo-1,2,5-thiadiazolidin-2-yl)phenyl]carbamoylamino]piperidine-1-carboxylate;

1-[3-fluoro-5-hydroxy-4-(1,1,4-trioxo-1,2,5-thiadiazolidin-2-yl)phenyl]-3-[4-(hydroxymethyl)-cyclohexyl]urea;

1-[3-fluoro-5-hydroxy-4-(1,1,4-trioxo-1,2,5-thiadiazolidin-2-yl)phenyl]-3-[(1R,2S)-2-hydroxyindan-1-yl]urea;

1-[(1S)-1-benzyl-2-hydroxy-ethyl]-3-[3-fluoro-5-hydroxy-4-(1,1,4-trioxo-1,2,5-thiadiazolidin-2-yl)phenyl]urea;

1-[3-fluoro-5-hydroxy-4-(1,1,4-trioxo-1,2,5-thiadiazolidin-2-yl)phenyl]-3-[(1S)-1-(hydroxymethyl)-3-methyl-butyl]urea;

1-[3-fluoro-5-hydroxy-4-(1,1,4-trioxo-1,2,5-thiadiazolidin-2-yl)phenyl]-3-[3-(hydroxymethyl)-1-bicyclo[1.1.1]pentanyl]urea;

3-[[3-fluoro-5-hydroxy-4-(1,1,4-trioxo-1,2,5-thiadiazolidin-2-yl)phenyl]carbamoylamino]-N-isobutyl-bicyclo[1.1.1]pentane-1-carboxamide or a pharmaceutically acceptable salt, stereoisomer, solvate, prodrug, or tautomer thereof.

In some embodiments, the compound is selected from:

1-[4-(1,1-dioxido-4-oxo-1,2,5-thiadiazolidin-2-yl)-3-fluoro-5-hydroxyphenyl]-3-phenylurea;

1-[4-(1,1-dioxido-4-oxo-1,2,5-thiadiazolidin-2-yl)-3-fluoro-5-hydroxyphenyl]-3-(2-methoxyphenyl)urea;

1-cyclohexyl-3-[4-(1,1-dioxido-4-oxo-1,2,5-thiadiazolidin-2-yl)-3-fluoro-5-hydroxyphenyl]urea;

1-[4-(1,1-dioxido-4-oxo-1,2,5-thiadiazolidin-2-yl)-3-fluoro-5-hydroxyphenyl]-3-(tetrahydrofuran-2-ylmethyl)urea;

1-[4-(1,1-dioxido-4-oxo-1,2,5-thiadiazolidin-2-yl)-3-fluoro-5-hydroxyphenyl]-3-(3-methoxypropyl)urea;

1-benzyl-3-[4-(1,1-dioxido-4-oxo-1,2,5-thiadiazolidin-2-yl)-3-fluoro-5-hydroxyphenyl]urea;

1-[4-(1,1-dioxido-4-oxo-1,2,5-thiadiazolidin-2-yl)-3-fluoro-5-hydroxyphenyl]-3-(3-methylbutyl)urea;

tert-butyl 4-[[3-fluoro-5-hydroxy-4-(1,1,4-trioxo-1,2,5-thiadiazolidin-2-yl)phenyl]carbamoyl-amino]piperidine-1-carboxylate;

1-[3-fluoro-5-hydroxy-4-(1,1,4-trioxo-1,2,5-thiadiazolidin-2-yl)phenyl]-3-(4-piperidyl)urea;

1-(2-azaspiro[4.5]decan-4-ylmethyl)-3-[3-fluoro-5-hydroxy-4-(1,1,4-trioxo-1,2,5-thiadiazolidin-2-yl)phenyl]urea;

tert-butyl 4-[[[3-fluoro-5-hydroxy-4-(1,1,4-trioxo-1,2,5-thiadiazolidin-2-yl)phenyl]carbamoyl-amino]methyl]-2-azaspiro[4.5]decane-2-carboxylate;

1-[3-fluoro-5-hydroxy-4-(1,1,4-trioxo-1,2,5-thiadiazolidin-2-yl)phenyl]-3-[(2-isopentyl-2-azaspiro[4.5]decan-4-yl)methyl]urea;

1-[3-fluoro-5-hydroxy-4-(1,1,4-trioxo-1,2,5-thiadiazolidin-2-yl)phenyl]-3-[(1S)-2-hydroxy-1-phenylethyl]urea;

1-[3-fluoro-5-hydroxy-4-(1,1,4-trioxo-1,2,5-thiadiazolidin-2-yl)phenyl]-3-(3-piperidyl)urea;

1-[3-fluoro-5-hydroxy-4-(1,1,4-trioxo-1,2,5-thiadiazolidin-2-yl)phenyl]-3-(2-hydroxy cyclohexyl)urea;

tert-butyl 3-[[3-fluoro-5-hydroxy-4-(1,1,4-trioxo-1,2,5-thiadiazolidin-2-yl)phenyl]carbamoylamino]piperidine-1-carboxylate;

1-[3-fluoro-5-hydroxy-4-(1,1,4-trioxo-1,2,5-thiadiazolidin-2-yl)phenyl]-3-[4-(hydroxymethyl)-cyclohexyl]urea;

1-[3-fluoro-5-hydroxy-4-(1,1,4-trioxo-1,2,5-thiadiazolidin-2-yl)phenyl]-3-[(1R,2S)-2-hydroxyindan-1-yl]urea;

1-[(1S)-1-benzyl-2-hydroxy-ethyl]-3-[3-fluoro-5-hydroxy-4-(1,1,4-trioxo-1,2,5-thiadiazolidin-2-yl)phenyl]urea;

1-[3-fluoro-5-hydroxy-4-(1,1,4-trioxo-1,2,5-thiadiazolidin-2-yl)phenyl]-3-[(1S)-1-(hydroxymethyl)-3-methyl-butyl]urea;

1-[3-fluoro-5-hydroxy-4-(1,1,4-trioxo-1,2,5-thiadiazolidin-2-yl)phenyl]-3-[3-(hydroxymethyl)-1-bicyclo[1.1.1]pentanyl]urea;

3-[[3-fluoro-5-hydroxy-4-(1,1,4-trioxo-1,2,5-thiadiazolidin-2-yl)phenyl]carbamoylamino]-N-isobutyl-bicyclo[1.1.1]pentane-1-carboxamide or a pharmaceutically acceptable salt, stereoisomer, solvate, prodrug, or tautomer thereof.

In some embodiments, the compound is 1-[4-(1,1-dioxido-4-oxo-1,2,5-thiadiazolidin-2-yl)-3-fluoro-5-hydroxyphenyl]-3-phenylurea or a pharmaceutically acceptable salt, stereoisomer, solvate, prodrug, or tautomer thereof.

In some embodiments, the compound is 1-[4-(1,1-dioxido-4-oxo-1,2,5-thiadiazolidin-2-yl)-3-fluoro-5-hydroxyphenyl]-3-(2-methoxyphenyl)urea or a pharmaceutically acceptable salt, stereoisomer, solvate, prodrug, or tautomer thereof.

In some embodiments, the compound is 1-cyclohexyl-3-[4-(1,1-dioxido-4-oxo-1,2,5-thiadiazolidin-2-yl)-3-fluoro-5-hydroxyphenyl]urea or a pharmaceutically acceptable salt, stereoisomer, solvate, prodrug, or tautomer thereof.

In some embodiments, the compound is 1-[4-(1,1-dioxido-4-oxo-1,2,5-thiadiazolidin-2-yl)-3-fluoro-5-hydroxyphenyl]-3-(tetrahydrofuran-2-ylmethyl)urea or a pharmaceutically acceptable salt, stereoisomer, solvate, prodrug, or tautomer thereof.

In some embodiments, the compound is 1-[4-(1,1-dioxido-4-oxo-1,2,5-thiadiazolidin-2-yl)-3-fluoro-5-hydroxyphenyl]-3-(3-methoxypropyl)urea or a pharmaceutically acceptable salt, stereoisomer, solvate, prodrug, or tautomer thereof.

In some embodiments, the compound is 1-benzyl-3-[4-(1,1-dioxido-4-oxo-1,2,5-thiadiazolidin-2-yl)-3-fluoro-5-hydroxyphenyl]urea or a pharmaceutically acceptable salt, stereoisomer, solvate, prodrug, or tautomer thereof.

In some embodiments, the compound is 1-[4-(1,1-dioxido-4-oxo-1,2,5-thiadiazolidin-2-yl)-3-fluoro-5-hydroxyphenyl]-3-(3-methylbutyl)urea or a pharmaceutically acceptable salt, stereoisomer, solvate, prodrug, or tautomer thereof.

In some embodiments, the compound is 1-[4-(1,1-dioxido-4-oxo-1,2,5-thiadiazolidin-2-yl)-3-fluoro-5-hydroxyphenyl]-3-(1-methylpiperidin-4-yl)urea or a pharmaceutically acceptable salt, stereoisomer, solvate, prodrug, or tautomer thereof.

In some embodiments, the compound is a pharmaceutically acceptable salt. In some embodiments, the compound is a hydrochloride salt.

It should be understood that all isomeric forms are included within the present invention, including mixtures thereof. If the compound contains a double bond, the substituent may be in the E or Z configuration. If the compound contains a disubstituted cycloalkyl, the cycloalkyl substituent may have a cis- or trans configuration. All tautomeric forms are also intended to be included.

Compounds of the invention, and pharmaceutically acceptable salts, hydrates, solvates, stereoisomers and prodrugs thereof may exist in their tautomeric form (for example, as an amide or imino ether). All such tautomeric forms are contemplated herein as part of the present invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention. each compound herein disclosed includes all the enantiomers that conform to the general structure of the compound. The compounds may be in a racemic or enantiomerically pure form, or any other form in terms of stereochemistry. The assay results may reflect the data collected for the racemic form, the enantiomerically pure form, or any other form in terms of stereochemistry.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of a chiral HPLC column.

It is also possible that the compounds of the invention may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester," "prodrug" and the like, is intended to equally apply to the salt, solvate, ester and prodrug of enantiomers, stereoisomers, rotamers, tautomers, positional isomers, racemates or prodrugs of the inventive compounds.

The compounds of Formula I may form salts which are also within the scope of this invention. Reference to a compound of the Formula herein is understood to include reference to salts thereof, unless otherwise indicated.

The present invention relates to compounds which are modulators of protein tyrosine phosphatase enzymes.

In one embodiment, the compounds of the present invention are inhibitors of protein tyrosine phosphatase enzymes. In another embodiment, the protein tyrosine phosphatase enzyme is protein tyrosine phosphatase non-receptor type 1 (PTPN1). In another embodiment, the protein tyrosine phosphatase enzyme is protein tyrosine phosphatase non-receptor type 2 (PTPN2).

In some embodiments, the compounds of Formula I are selective inhibitors of protein tyrosine phosphatase enzymes.

The invention is directed to compounds as described herein and pharmaceutically acceptable salts, hydrates, solvates, prodrugs, stereoisomers, or tautomers thereof, and pharmaceutical compositions comprising one or more compounds as described herein, or pharmaceutically acceptable salts, hydrates, solvates, prodrugs, stereoisomers, or tautomers thereof.

Method of Synthesizing the Compounds

The compounds of the present invention may be made by a variety of methods, including standard chemistry. Suitable synthetic routes are depicted in the Schemes given below.

The compounds of Formula (I) may be prepared by methods known in the art of organic synthesis as set forth in part by the following synthetic schemes. In the schemes described below, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis", Third edition, Wiley, New York 1999). These groups are removed at a convenient stage of the compound synthesis using methods that are readily apparent to those skilled in the art. The selection processes, as well as the reaction conditions and order of those skilled in the art will recognize if a stereocenter exists in the compounds of Formula (I). Accordingly, the present invention includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. Resolution of the final product, an intermediate, or a starting material may be affected by any suitable method known in the art. See, for example, "Stereochemistry of Organic Compounds" by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

The compounds of the present invention can be prepared in a number of ways well known to those skilled in the art of organic synthesis. By way of example, compounds of the present invention can be synthesized using the methods described below, together with synthetic methods known in the art of synthetic organic chemistry, or variations thereon as appreciated by those skilled in the art. Suitable methods include but are not limited to those methods described below. Compounds of the present invention can be synthesized by following the steps outlined in General Procedures A-C which comprise different sequences of assembling intermediates or compounds. Starting materials are either commercially available or made by known procedures in the reported literature or as illustrated below.

General Procedure A
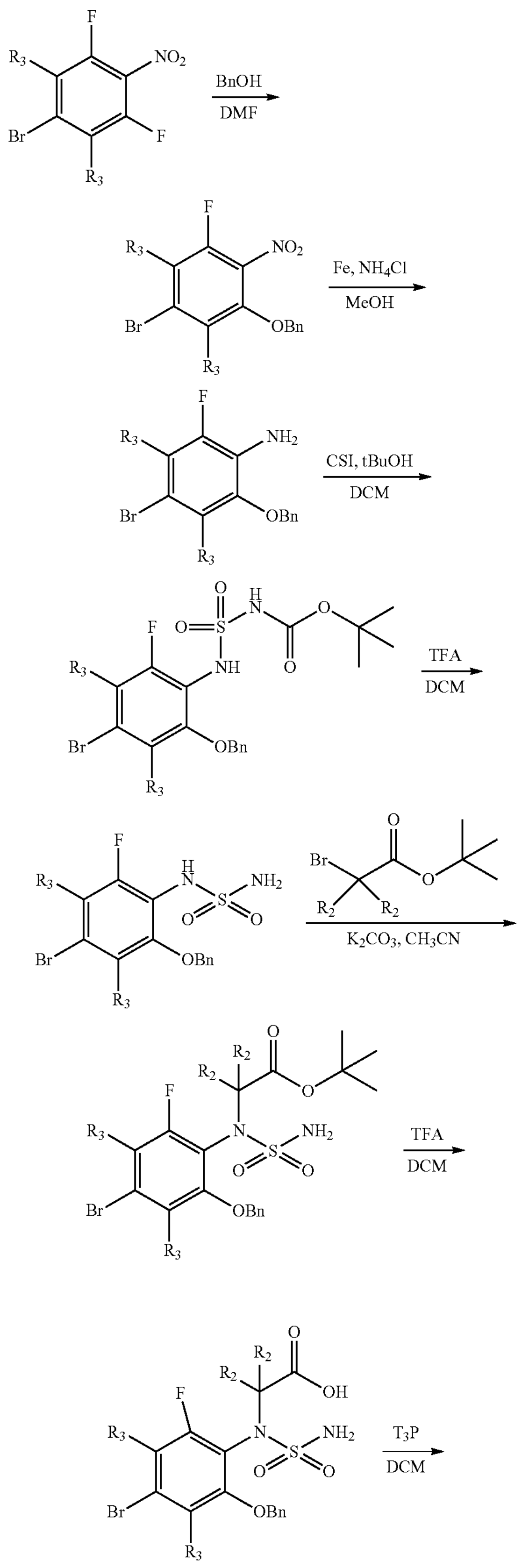
-continued
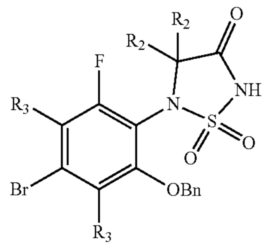
General Procedure B
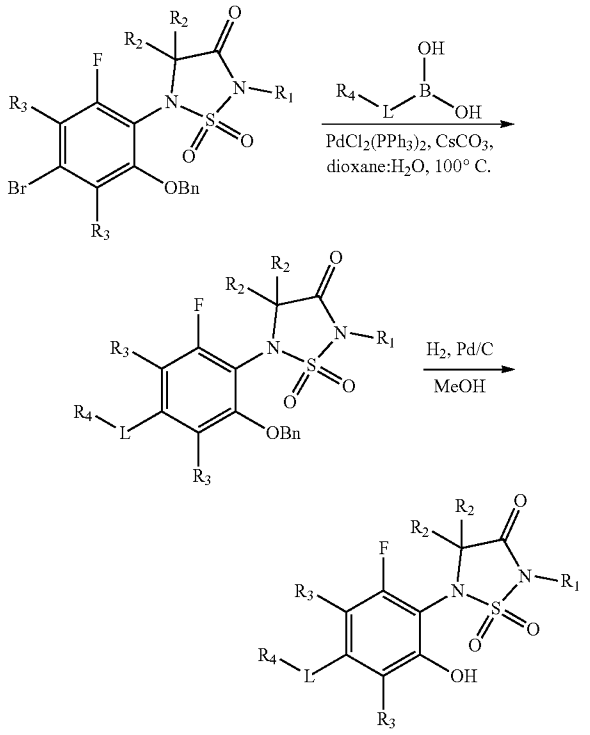
General Procedure C
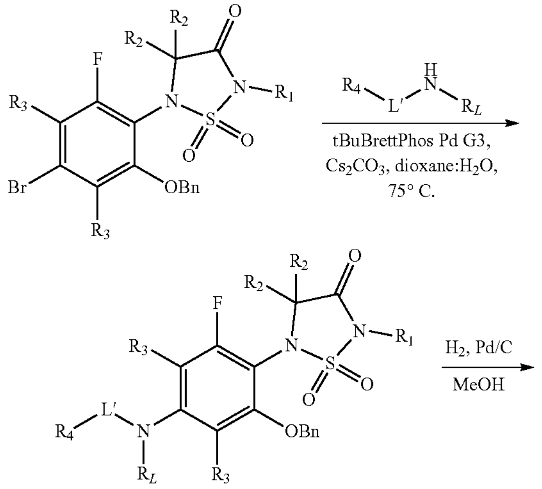

-continued

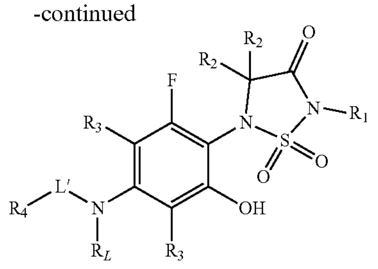

wherein L' is selected from —C(O)— and —$S(O)_2$—.

Methods of Using the Disclosed Compounds

Another aspect of the invention relates to a method of treating a disease or disorder associated with modulation of protein tyrosine phosphatase enzymes. The method comprises administering to a patient in need of a treatment for diseases or disorders associated with modulation of protein tyrosine phosphatase enzymes an effective amount the compositions and compounds of Formula (I).

In another aspect, the present invention is directed to a method of inhibiting protein tyrosine phosphatase enzymes. The method involves administering to a patient in need thereof an effective amount of a compound of Formula (I).

Another aspect of the present invention relates to a method of treating, preventing, inhibiting or eliminating a disease or disorder in a patient associated with the inhibition of protein tyrosine phosphatase enzymes, the method comprising administering to a patient in need thereof an effective amount of a compound of Formula (I). In one embodiment, the disease may be, but not limited to, cancer and metabolic diseases.

The present invention also relates to the use of an inhibitor of PTPN1 and PTPN2 proteins for the preparation of a medicament used in the treatment, prevention, inhibition or elimination of a disease or condition mediated by protein tyrosine phosphatase enzymes, wherein the medicament comprises a compound of Formula (I).

In another aspect, the present invention relates to a method for the manufacture of a medicament for treating, preventing, inhibiting, or eliminating a disease or condition mediated by protein tyrosine phosphatase enzymes, wherein the medicament comprises a compound of Formula (I).

Another aspect of the present invention relates to a compound of Formula (I) for use in the manufacture of a medicament for treating a disease associated with inhibiting protein tyrosine phosphatase enzymes.

In another aspect, the present invention relates to the use of a compound of Formula (I) in the treatment of a disease associated with inhibiting protein tyrosine phosphatase enzymes.

Another aspect of the invention relates to a method of treating cancer. The method comprises administering to a patient in need thereof an effective amount of a compound of Formula (I).

Another aspect of the invention relates to a method of treating or preventing cancer. The method comprises administering to a patient in need thereof an effective amount of a compound of Formula (I).

In one embodiment, the present invention relates to the use of an inhibitor of protein tyrosine phosphatase enzymes for the preparation of a medicament used in treatment, prevention, inhibition or elimination of a disease or disorder associated with cancer.

Another aspect of the invention relates to a method of treating a metabolic disease. The method comprises administering to a patient in need thereof an effective amount of a compound of Formula (I).

Another aspect of the invention relates to a method of treating or preventing a metabolic disease. The method comprises administering to a patient in need thereof an effective amount of a compound of Formula (I).

In one embodiment, the present invention relates to the use of an inhibitor of protein tyrosine phosphatase enzymes for the preparation of a medicament used in treatment, prevention, inhibition or elimination of a disease or disorder associated with a metabolic disease.

In another embodiment, the present invention relates to a compound of Formula (I) or a pharmaceutical composition comprising a compound of the present invention and a pharmaceutically acceptable carrier used for the treatment of cancers including, but not limited to, bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, prostate cancer, marginal zone lymphoma (MZL), follicular lymphoma (FL), diffuse large B-cell lymphoma (DLBCL), and chronic lymphocytic leukemia/small lymphocytic lymphoma (CLL/SLL). In another embodiment, the present invention relates to compounds of Formula (I) or pharmaceutical compositions comprising a compound of the present invention and a pharmaceutically acceptable carrier used for the treatment of melanoma.

In another embodiment, the present invention relates to a compound of Formula (I) or a pharmaceutical composition comprising a compound of the present invention and a pharmaceutically acceptable carrier used for the treatment of metabolic diseases including, but not limited to, non-alcoholic steatohepatitis (NASH), non-alcoholic fatty liver disease (NAFLD), liver fibrosis, obesity, heart disease, atherosclerosis, arthritis, cystinosis, diabetes (e.g., Type I diabetes, Type II diabetes, or gestational diabetes), metabolic syndrome, phenylketonuria, proliferative retinopathy, or Kearns-Sayre disease.

Another aspect of the invention is directed to pharmaceutical compositions comprising a compound of Formula (I) and a pharmaceutically acceptable carrier. The pharmaceutical acceptable carrier may further include an excipient, diluent, or surfactant.

In one embodiment, are provided methods of treating a disease or disorder associated with modulation of protein tyrosine phosphatase enzymes, including cancer or cell proliferative disorder, comprising administering to a patient suffering from at least one of said diseases or disorder a compound of Formula (I).

One therapeutic use of the compounds or compositions of the present invention which inhibit protein tyrosine phosphatase enzymes is to provide treatment to patients or subjects suffering from a cancer or cell proliferative disorder.

The disclosed compounds of the invention can be administered in effective amounts to treat or prevent a disorder and/or prevent the development thereof in subjects.

Administration of the disclosed compounds can be accomplished via any mode of administration for therapeutic agents. These modes include systemic or local administration such as oral, nasal, parenteral, transdermal, subcutaneous, vaginal, buccal, rectal or topical administration modes.

Depending on the intended mode of administration, the disclosed compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. Likewise, they can also be administered in intravenous (both bolus and infusion), intraperitoneal, subcutaneous or intramuscular form, and all using forms well known to those skilled in the pharmaceutical arts.

Illustrative pharmaceutical compositions are tablets and gelatin capsules comprising a Compound of the Invention and a pharmaceutically acceptable carrier, such as a) a diluent, e.g., purified water, triglyceride oils, such as hydrogenated or partially hydrogenated vegetable oil, or mixtures thereof, corn oil, olive oil, sunflower oil, safflower oil, fish oils, such as EPA or DHA, or their esters or triglycerides or mixtures thereof, omega-3 fatty acids or derivatives thereof, lactose, dextrose, sucrose, mannitol, sorbitol, cellulose, sodium, saccharin, glucose and/or glycine; b) a lubricant, e.g., silica, talcum, stearic acid, its magnesium or calcium salt, sodium oleate, sodium stearate, magnesium stearate, sodium benzoate, sodium acetate, sodium chloride and/or polyethylene glycol; for tablets also; c) a binder, e.g., magnesium aluminum silicate, starch paste, gelatin, tragacanth, methylcellulose, sodium carboxymethylcellulose, magnesium carbonate, natural sugars such as glucose or beta-lactose, corn sweeteners, natural and synthetic gums such as acacia, tragacanth or sodium alginate, waxes and/or polyvinylpyrrolidone, if desired; d) a disintegrant, e.g., starches, agar, methyl cellulose, bentonite, xanthan gum, algic acid or its sodium salt, or effervescent mixtures; e) absorbent, colorant, flavorant and sweetener; f) an emulsifier or dispersing agent, such as Tween 80, Labrasol, HPMC, DOSS, caproyl 909, labrafac, labrafil, peceol, transcutol, capmul MCM, capmul PG-12, captex 355, gelucire, vitamin E TGPS or other acceptable emulsifier; and/or g) an agent that enhances absorption of the compound such as cyclodextrin, hydroxypropyl-cyclodextrin, PEG400, or PEG200.

Liquid, particularly injectable, compositions can, for example, be prepared by dissolution, dispersion, etc. For example, the disclosed compound is dissolved in or mixed with a pharmaceutically acceptable solvent such as, for example, water, saline, aqueous dextrose, glycerol, ethanol, and the like, to thereby form an injectable isotonic solution or suspension. Proteins such as albumin, chylomicron particles, or serum proteins can be used to solubilize the disclosed compounds.

The disclosed compounds can be also formulated as a suppository that can be prepared from fatty emulsions or suspensions; using polyalkylene glycols such as propylene glycol, as the carrier.

The disclosed compounds can also be administered in the form of liposome delivery systems, such as small unilamellar vesicles, large unilamellar vesicles and multilamellar vesicles. Liposomes can be formed from a variety of phospholipids, containing cholesterol, stearylamine or phosphatidylcholines. In some embodiments, a film of lipid components is hydrated with an aqueous solution of drug to a form lipid layer encapsulating the drug, as described in U.S. Pat. No. 5,262,564 which is hereby incorporated by reference in its entirety.

Disclosed compounds can also be delivered by the use of monoclonal antibodies as individual carriers to which the disclosed compounds are coupled. The disclosed compounds can also be coupled with soluble polymers as targetable drug carriers. Such polymers can include polyvinylpyrrolidone, pyran copolymer, polyhydroxypropylmethacrylamide-phenol, polyhydroxyethylaspanamidephenol, or polyethyleneoxidepolylysine substituted with palmitoyl residues. Furthermore, the Disclosed compounds can be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels. In one embodiment, disclosed compounds are not covalently bound to a polymer, e.g., a polycarboxylic acid polymer, or a polyacrylate.

Parenteral injectable administration is generally used for subcutaneous, intramuscular or intravenous injections and infusions. Injectables can be prepared in conventional forms, either as liquid solutions or suspensions or solid forms suitable for dissolving in liquid prior to injection.

Another aspect of the invention is directed to pharmaceutical compositions comprising a compound of Formula (I) and a pharmaceutically acceptable carrier. The pharmaceutical acceptable carrier may further include an excipient, diluent, or surfactant. In some embodiments, the pharmaceutical composition can further comprise an additional pharmaceutically active agent.

In some embodiments, the additional therapeutic agent is selected from anti-proliferative agents, anti-cancer agents, anti-diabetic agents, anti-inflammatory agents, immunosuppressant agents, immunotherapeutic agents, and pain-relieving agents.

In some embodiments, the immunotherapeutic agent is selected from an anti-PD-1 antibody, an anti-PD-L1 antibody and an anti-CTLA-4 antibody.

In some embodiments, the immunotherapeutic agent is an anti-PD-1 antibody.

In some embodiments, the immunotherapeutic agent is selected from an anti-PD-L1 antibody.

In some embodiments, the compounds of the present disclosure are used with a cancer immunotherapy to treat a subject in need thereof. In some embodiments, the cancer immunotherapy is a cell-based therapy. In some embodiments, the cancer immunotherapy is an antibody-based therapy. In some embodiments, the cancer immunotherapy is a cytokine therapy.

In some embodiments, the cancer immunotherapy is selected from an immune checkpoint antibody and a cancer vaccine.

In some embodiments, the immune checkpoint antibody is selected from a PD-1 antibody, a PD-L1 antibody, a PD-L2 antibody, a CTLA-4 antibody, a TIM3 antibody, a LAG3 antibody, and a TIGIT antibody.

In some embodiments, the cancer vaccine is selected from an anti-tumor vaccine or a vaccine based on neoantigens.

Cell-based therapies usually involve the removal of immune cells from a subject suffering from cancer, either from the blood or from a tumor. Immune cells specific for the tumor will be activated, grown, and returned to a subject suffering from cancer where the immune cells provide an immune response against the cancer.

In some embodiments, the immune cells are selected from natural killer cells, lymphokine-activated killer cells, cytotoxic T-cells, and dendritic cells.

In some embodiments, the cell-based therapy is selected from CAR-T therapy (e.g., chimeric antigen receptor T-cells which are T-cells engineered to target specific antigens), TIL therapy (e.g., administration of tumor-infiltrating lymphocytes), and TCR gene therapy.

In some embodiments, the cell-based therapy is a cancer vaccine. In some embodiments, the cancer vaccine is a protein vaccine. In some embodiments, the cancer vaccine is a nucleic acid vaccine.

In some embodiments, the cytokine therapy is interleukin-2 therapy. In some embodiments, the cytokine therapy is interferon-alpha therapy.

Compositions can be prepared according to conventional mixing, granulating or coating methods, respectively, and the present pharmaceutical compositions can contain from about 0.1% to about 99%, from about 5% to about 90%, or from about 1% to about 20% of the disclosed compound by weight or volume.

The dosage regimen utilizing the disclosed compound is selected in accordance with a variety of factors including type, species, age, weight, sex and medical condition of the patient; the severity of the condition to be treated; the route of administration; the renal or hepatic function of the patient; and the particular disclosed compound employed. A physician or veterinarian of ordinary skill in the art can readily determine and prescribe the effective amount of the drug required to prevent, counter or arrest the progress of the condition.

Effective dosage amounts of the disclosed compounds, when used for the indicated effects, range from about 0.5 mg to about 5000 mg of the disclosed compound as needed to treat the condition. Compositions for in vivo or in vitro use can contain about 0.5, 5, 20, 50, 75, 100, 150, 250, 500, 750, 1000, 1250, 2500, 3500, or 5000 mg of the disclosed compound, or, in a range of from one amount to another amount in the list of doses. In one embodiment, the compositions are in the form of a tablet that can be scored.

EXAMPLES

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims. Abbreviations Used in the Following Examples and Elsewhere Herein are:

AcCl acetyl chloride
AcOH acetic acid
atm atmosphere
br broad
anh. anhydrous
aq. aqueous
BINAP 2,2'-bis(diphenylphosphino)-1,1'-binaphthalene
BnOH benzyl alcohol
BSA bovine serum albumin
BuLi butyl lithium
CDI N,N'-carbonyldiimidazole
CC column chromatography (e.g. silica CC)
$CO_2$ carbon dioxide
COSY correlation spectroscopy
CPBA chloroperbenzoic acid (e.g. m-CPBA)
CSI chlorosulfonyl isocyanate
DCM dichloromethane
DDQ 2,3-dichloro-5,6-dicyano-1,4-quinone
DIAD diisopropyl azodicarboxylate
DIPEA N,N-diisopropylethylamine
DMAc N,N-dimethyl acetamide
DMAP N,N-dimethylpyridin-4-amine
DME 1,2-Dimethoxyethane
DMEDA N,N'-Dimethylethylenediamine
DMEM Dulbecco's modified Eagle's medium
DMF N,N-dimethyl formamide
DMSO dimethyl sulfoxide
DTT dithiothreitol
EDCI 1-(3-Dimethylaminopropyl)-3-ethylcarbodiimide
EDTA ethylenedi-aminetetraacetic acid
ESI electrospray ionization
Et-I iodoethane
$Et_2O$ diethyl ether
EtOAc ethyl acetate
EtOH ethanol
FA formic acid
FBS fetal bovine serum
FC flash chromatography (e.g. silica FC)
h hour(s)
Hal halogen
HEPES 4-(2-hydroxyethyl)piperazine-1-ethanesulfonic acid
Het heteryl
HOBt 1-hydroxybenzotriazole
HATU [bis(dimethylamino)methylene]-1H-1,2,3-triazolo[4,5-b]pyridinium 3-oxide hexafluorophosphate
HPLC high pressure (or performance) liquid chromatography
t-BuOK potassium tert-butoxide
INFγ interferon gamma
LCMS liquid chromatography mass spectrometry
LHMDS Lithium bis(trimethylsilyl)amide
m multiplet
M molar
MeCN acetonitrile
2-MeTHF 2-methyl tetrahydrofuran
MeOH methanol
MHz megahertz
min minutes
MS molecular sieves
MsCl methanesulfonyl chloride
MsCl methanesulfonic acid
n-BuLi butyl lithium
NBS N-bromosuccinimide
NIS N-iodosuccinimide
NMR nuclear magnetic resonance
NOE nuclear Overhauser effect
NOESY nuclear Overhauser effect correlation spectroscopy
PBS phosphate-buffered saline
PEG polyethylene glycol
pin pinacolate
ppm parts per million
quant. Quantitative
rac racemic mixture
rt room temperature
Rt retention time
sat. saturated
STAB sodium triacetoxyborohydride
$T_3P$ Propylphosphonic anhydride
TBAB tetrabutylammonium bromide
TBTU O-(Benzotriazol-1-yl)-N,N,N',N'-tetramethyluronium tetrafluoroborate
TosMIC toluenesulfonylmethyl isocyanide tBuBrettPhos Pd [(2-Di-tert-butylphosphino-3,6-dimethoxy-2',4',6'-triisopropyl-G3 1,1'-biphenyl)-2-(2'-amino-1,1'-biphenyl)]palladium(II) methanesulfonate
t-BuOH tert-butanol
TFA trifluoroacetic acid
THF tetrahydrofuran
TLC thin layer chromatography
TsCl toluenesulfonyl chloride (e.g. p-TsCl)
TsOH toluenesulfonic acid (e.g. p-TsOH)

Purity and identity of all synthesized compounds were confirmed by LC-MS analysis performed on Shimadzu Analytical 10 Avp equipped with PE SCIEX API 165 mass-, Sedex 75 ELSD-, and Shimadzu UV- (254 and 215) detectors. Separation was achieved with C18 column 100×4.6 mm, 5.0 μm, pore size 100 Å, water-acetonitrile+0.1 TFA, gradient 5 to 87 for 10 min.

Preparative HPLC purification was carried out on Shimadzu instrument equipped with SPD-10 Avp detector and FRC-10A fraction collector. Separation was achieved with a column YMC-Pack ODS-AQ 250×20 mml, S-10 μm, 12 nm, gradient solution A–solution B (A: 1000 mL $H_2O$-226 μL TFA; B: 1000 mL $CH_3CN$-226 μL TFA).

Synthesis of Intermediates

Preparation 1: 5-[2-(benzyloxy)-4-bromo-6-fluorophenyl]-1,2,5-thiadiazolidin-3-one 1,1-dioxide

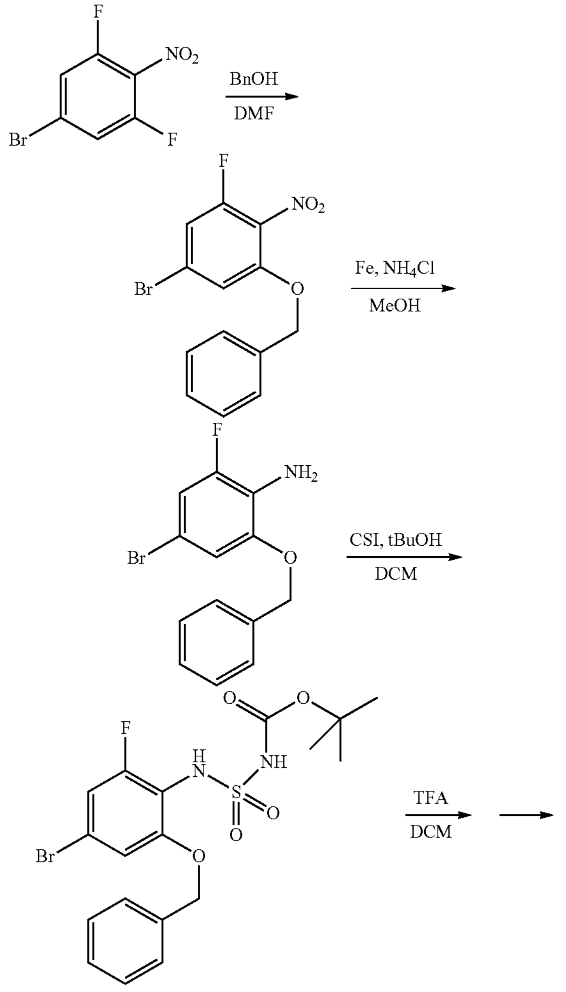

-continued

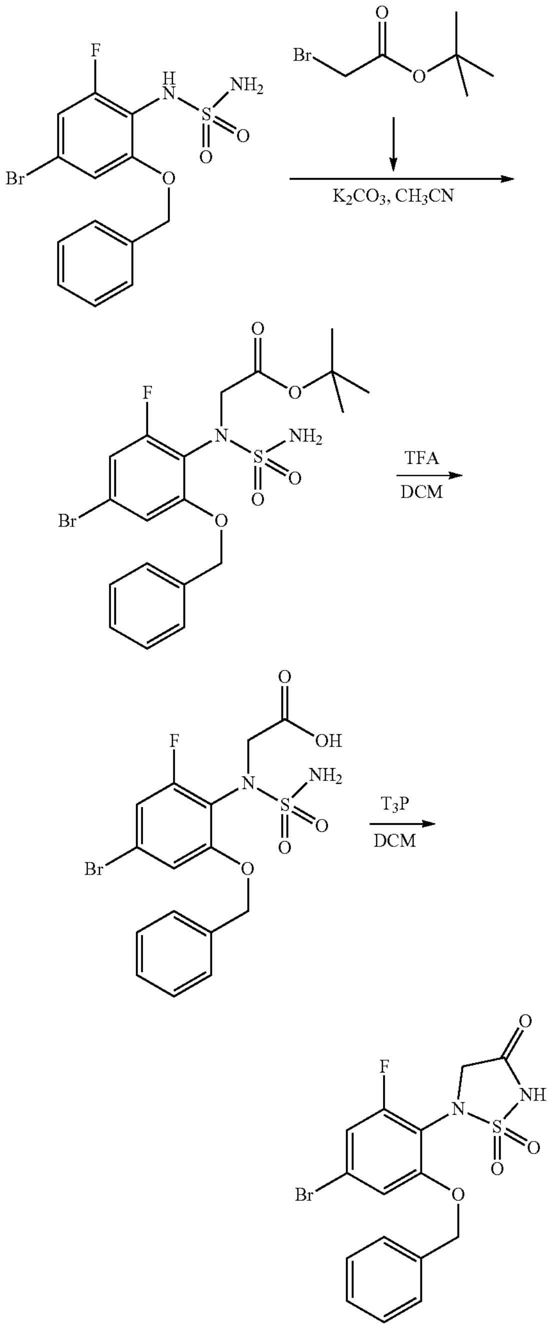

Step A: Synthesis of 1-(benzyloxy)-5-bromo-3-fluoro-2-nitrobenzene

A mixture of 5-bromo-1,3-difluoro-2-nitrobenzene (13 g, 55 mmol), benzyl alcohol (5.65 mL, 55 mmol) $K_2CO_3$ (15.2 g, 110 mmol), and DMF (150 mL) was stirred at 70° C. for 12 hour, cooled, and filtered, and the filtrate was concentrated under reduced pressure. The residue was dissolved in DCM, washed with water, brine, dried over anh. $Na_2SO_4$, and concentrated under reduced pressure to afford 10.7 g (73.3%) of the title compound that was used for the next step without further purification.

Step B: Synthesis of 2-(benzyloxy)-4-bromo-6-fluoroaniline

A mixture of the crude product from Step A (10.7 g, 33 mmol), $NH_4Cl$ (8.2 g, 16 mmol), iron powder (9.2 g, 160 mmol), MeOH (200 mL), and water (15 mL) was stirred under reflux for 3 h, cooled down to ambient temperature, filtered thorough Celite pad, and concentrated under reduced pressure. The residue was dissolved in EtOAc, washed with sat. aq. solution of $NaHCO_3$, brine, filtered thorough Celite pad, dried over anh. $Na_2SO_4$, and concentrated under reduced pressure to afford 7.29 g (76%) of the title compound that was used for the next step without further purification.

Step C: Synthesis of tert-butyl {[2-(benzyloxy)-4-bromo-6-fluorophenyl]sulfamoyl}carbamate CSI (3.21 mL, 037 mmol) was added dropwise to a solution t-BuOH (3.5 mL, 37 mmol) in DCM (25 mL). The obtained mixture was stirred at 25° C. for 30 min and then added dropwise to a solution of the crude product from Step B (7.29 g, 25 mmol) and $Et_3N$ (7 ml, 50 mol) in DCM (100 mL). The mixture was stirred for 3 h, and the solvent was evaporated under reduced pressure. The residue was subjected to silica FC eluting with a mixture of EtOAc (0 to 5%) and DCM to afford 9.5 g (79.1%) of the title compound.

Step D: Synthesis of N-[2-(benzyloxy)-4-bromo-6-fluorophenyl]sulfamide

TFA (7.7 mL, 100 mmol) was added to a stirred solution of the crude product from Step C (5 g, 10 mmol) in 100 ml DCM. The mixture was stirred for 7 h, volatiles were removed under reduced pressure, and the residue was subjected to silica FC eluting with a mixture of EtOAc (0 to 10%) and DCM to afford 2.88 g (72%) of the title compound.

Step E: Synthesis of tert-butyl N-[2-(benzyloxy)-4-bromo-6-fluorophenyl]-N-sulfamoylglycinate A solution of tret-butyl bromoacetate (1.3 mL, 7.6 mmol) in $CH_3CN$ (50 mL) was added dropwise to a stirred mixture of the product from Step D (2.88 g, 7.6 mmol), $K_2CO_3$ (4.24 g, 30.4 mmol) and $CH_3CN$ (100 mL). The reaction mixture was stirred at 25° C. for 12 h, filtered, the filtrate was concentrated under reduced pressure to afford 3.46 g (85.4%) of the crude product that was used for the next step without additional purification.

Step F. Synthesis of N-[2-(benzyloxy)-4-bromo-6-fluorophenyl]-N-sulfamoylglycine TFA (9.7 mL, 145 mmol) was added potion-wise to a stirred solution of the crude product from Step E (7.3 g, 14.5 mmol) in DCM (100 mL). The mixture was stirred for 9 h and concentrated under reduced pressure. The residue was subjected to silica FC eluting with a mixture of EtOAc (0 to 10%) and DCM to afford 4.81 g (76.2%) of the title compound.

Step G. Synthesis of 5-[2-(benzyloxy)-4-bromo-6-fluorophenyl]-1,2,5-thiadiazolidin-3-one 1,1-dioxide T3P (14.1 g of 50 solution in EtOAc, 22.2 mmol) was added dropwise to a mixture of the product from Step F (4.81 g, 11.1 mmol) and $Et_3N$ (2.42 mL, 16.7 mmol) in DCM (200 mL). The mixture was stirred for 14 h, washed with water, brine, dried over anh. $Na_2SO_4$, filtered, and concentrated under reduced pressure. The residue was subjected to silica CC eluting with EtOAc to afford 2.5 g (54.3%) of the title compound.

Example 1: 5-(3-fluoro-5-hydroxy-3'-methoxybiphenyl-4-yl)-1,2,5-thiadiazolidin-3-one 1,1-dioxide

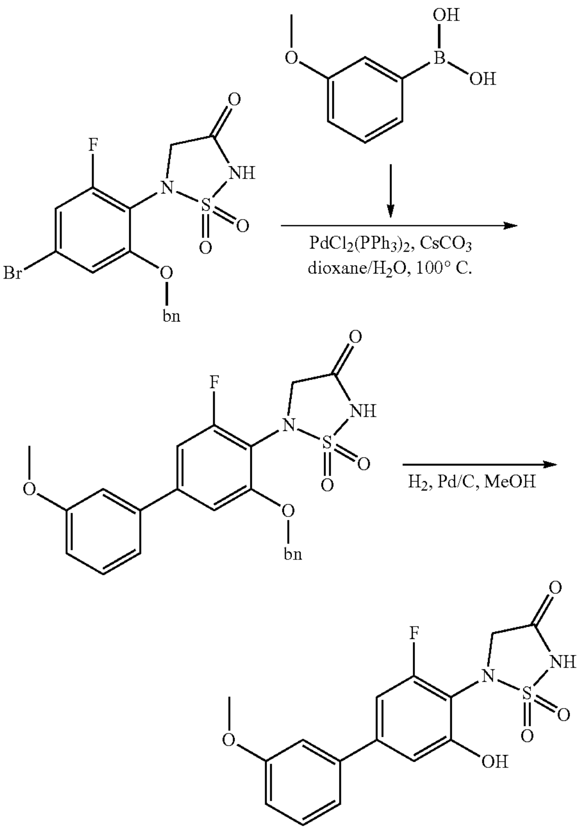

Step A: 5-[3-(benzyloxy)-5-fluoro-3'-methoxybiphenyl-4-yl]-1,2,5-thiadiazolidin-3-one 1,1-dioxide A degassed mixture of (5-[2-(benzyloxy)-4-bromo-6-fluorophenyl]-1,2,5-thiadiazolidin-3-one 1,1-dioxide (120 mg, 0.29 mmol) (See Preparation 1), (3-methoxyphenyl) boronic acid (66 mg, 0.43 mmol), $Cs_2CO_3$ (190 mg, 0.58 mmol), $PdCl_2(PPh_3)_2$ (10 mg, 5 mol), dioxane (2 mL), $H_2O$ (0.2 mL), was stirred in argon atmosphere at 75° C. for 30 min, cooled, diluted with water, acidified with conc. HCl to pH 2, and partitioned between water (2 mL) and DCM (6 mL). The organic layer was separated, washed with brine, dried over anh. $Na_2SO_4$, and concentrated under reduced pressure. The residue was subjected to silica FC eluting with MeOH (0→20%) and EtOAc to afford 94 mg, (74%) of the title compound.

Step B: 5-(3-fluoro-5-hydroxy-3'-methoxybiphenyl-4-yl)-1,2,5-thiadiazolidin-3-one 1,1-dioxide A mixture of the compound from Step A (94 mg, 0.21 mmol), methanol (2 mL), and 10 $PdCl_2$ on charcoal (7 mg)

was vigorously stirred under $H_2$ atmosphere for 2 h at ambient temperature until reaction completion (TLC monitoring) and filtered through Celite pad. The filtrate was concentrated under reduced pressure, and the residue was subjected to silica FC eluting with mixture of HCOOH (0→20%) and DCM to afford 35 mg (47%) of the title compound.

Example 2: 5-(3,3'-difluoro-5-hydroxybiphenyl-4-yl)-1,2,5-thiadiazolidin-3-one 1,1-dioxide

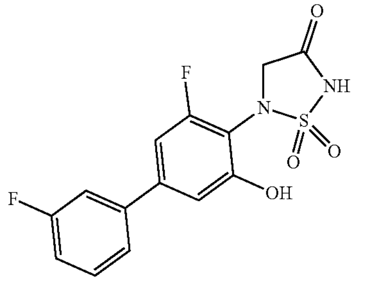 [SMILES: O=C1CN(c2c(O)cc(-c3cccc(F)c3)cc2F)S(=O)(=O)N1]

The compound was synthesized according to the procedure described in Example 1 using (3-fluorophenyl)boronic acid instead of (3-methoxyphenyl)boronic acid.

Example 3: 5-(3-fluoro-5-hydroxy-4'-methoxybiphenyl-4-yl)-1,2,5-thiadiazolidin-3-one 1,1-dioxide

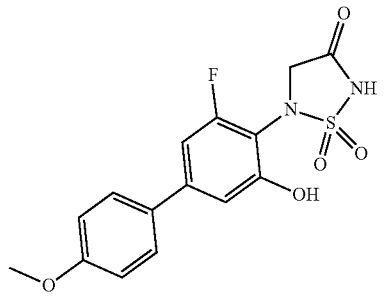 [SMILES: COc1ccc(-c2cc(O)c(N3CC(=O)NS3(=O)=O)c(F)c2)cc1]

The compound was synthesized according to the procedure described in Example 1 using (4-methoxyphenyl)boronic acid instead of (3-methoxyphenyl)boronic acid.

Example 4: 5-(3,3',5'-trifluoro-5-hydroxybiphenyl-4-yl)-1,2,5-thiadiazolidin-3-one 1,1-dioxide

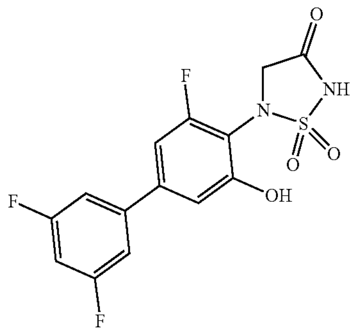 [SMILES: O=C1CN(c2c(O)cc(-c3cc(F)cc(F)c3)cc2F)S(=O)(=O)N1]

The compound was synthesized according to the procedure described in Example 1 using (3,5-difluorophenyl) boronic acid instead of (3-methoxyphenyl)boronic acid.

Example 5: 5-(2'-ethoxy-3-fluoro-5-hydroxybiphenyl-4-yl)-1,2,5-thiadiazolidin-3-one 1,1-dioxide

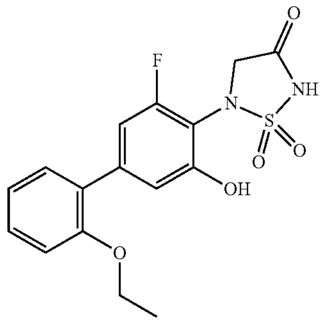 [SMILES: CCOc1ccccc1-c1cc(O)c(N2CC(=O)NS2(=O)=O)c(F)c1]

The compound was synthesized according to the procedure described in Example 1 using (2-ethoxyphenyl)boronic acid instead of (3-methoxyphenyl)boronic acid.

Example 6: 5-(3-fluoro-5-hydroxy-2'-methylbiphenyl-4-yl)-1,2,5-thiadiazolidin-3-one 1,1-dioxide

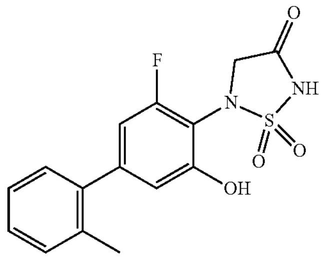 [SMILES: Cc1ccccc1-c1cc(O)c(N2CC(=O)NS2(=O)=O)c(F)c1]

The compound was synthesized according to the procedure described in Example 1 using (2-methylphenyl)boronic acid instead of (3-methoxyphenyl)boronic acid.

Example 7: 5-(2',3-difluoro-5-hydroxybiphenyl-4-yl)-1,2,5-thiadiazolidin-3-one 1,1-dioxide

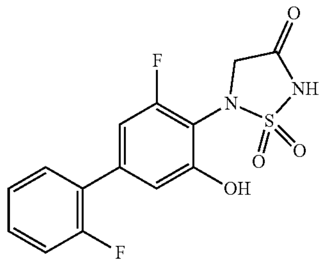 [SMILES: O=C1CN(c2c(O)cc(-c3ccccc3F)cc2F)S(=O)(=O)N1]

The compound was synthesized according to the procedure described in Example 1 using (2-fluorophenyl)boronic acid instead of (3-methoxyphenyl)boronic acid.

Example 8: 5-(3,4'-difluoro-5-hydroxybiphenyl-4-yl)-1,2,5-thiadiazolidin-3-one 1,1-dioxide

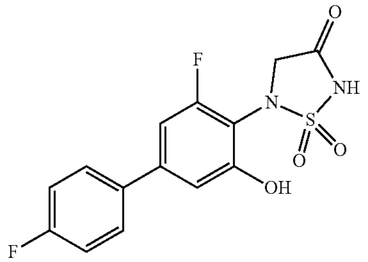 [SMILES: O=C1CN(c2c(O)cc(-c3ccc(F)cc3)cc2F)S(=O)(=O)N1]

The compound was synthesized according to the procedure described in Example 1 using (4-fluorophenyl)boronic acid instead of (3-methoxyphenyl)boronic acid.

Example 9: 5-(3-fluoro-5-hydroxy-3'-methylbiphenyl-4-yl)-1,2,5-thiadiazolidin-3-one 1,1-dioxide

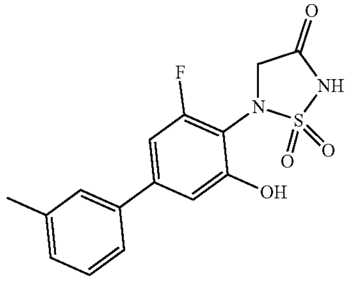 [SMILES: Cc1cccc(-c2cc(O)c(N3CC(=O)NS3(=O)=O)c(F)c2)c1]

The compound was synthesized according to the procedure described in Example 1 using (3-methylphenyl)boronic acid instead of (3-methoxyphenyl)boronic acid.

Example 10: 5-(3-fluoro-5-hydroxy-4'-methylbiphenyl-4-yl)-1,2,5-thiadiazolidin-3-one 1,1-dioxide

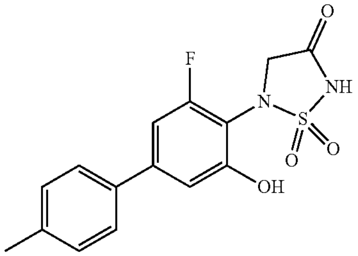 [SMILES: Cc1ccc(-c2cc(O)c(N3CC(=O)NS3(=O)=O)c(F)c2)cc1]

The compound was synthesized according to the procedure described in Example 1 using (4-methylphenyl)boronic acid instead of (3-methoxyphenyl)boronic acid.

Example 11: 5-[3'-({1-[(2-chlorobenzyl)sulfonyl]piperidin-4-yl}amino)-3-fluoro-5-hydroxybiphenyl-4-yl]-1,2,5-thiadiazolidin-3-one 1,1-dioxide

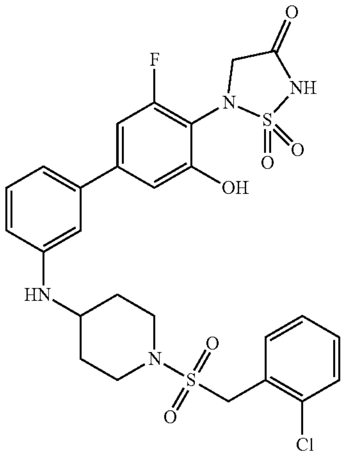 [SMILES: O=C1CN(c2c(O)cc(-c3cccc(NC4CCN(S(=O)(=O)Cc5ccccc5Cl)CC4)c3)cc2F)S(=O)(=O)N1]

The compound was synthesized according to the procedure described in Example 1 using 1-[(2-chlorobenzyl)sulfonyl]-N-[3-(4,4,5,5-tetramethyl-1,3,2-dioxaborolan-2-yl)phenyl]piperidin-4-amine instead of (3-methoxyphenyl)boronic acid.

Example 12: 5-(3'-{[1-(benzylsulfonyl)piperidin-4-yl]amino}-3-fluoro-5-hydroxybiphenyl-4-yl)-1,2,5-thiadiazolidin-3-one 1,1-dioxide

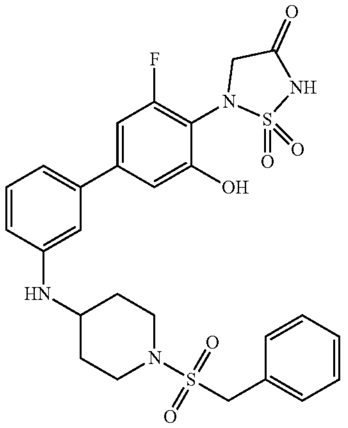 [SMILES: O=C1CN(c2c(O)cc(-c3cccc(NC4CCN(S(=O)(=O)Cc5ccccc5)CC4)c3)cc2F)S(=O)(=O)N1]

The compound was synthesized according to the procedure described in Example 1 using 1-(benzylsulfonyl)-N-[3-(4,4,5,5-tetramethyl-1,3,2-dioxaborolan-2-yl)phenyl]piperidin-4-amine instead of (3-methoxyphenyl)boronic acid.

Example 13: N-[4-(1,1-dioxido-4-oxo-1,2,5-thiadiazolidin-2-yl)-3-fluoro-5-hydroxyphenyl]benzamide

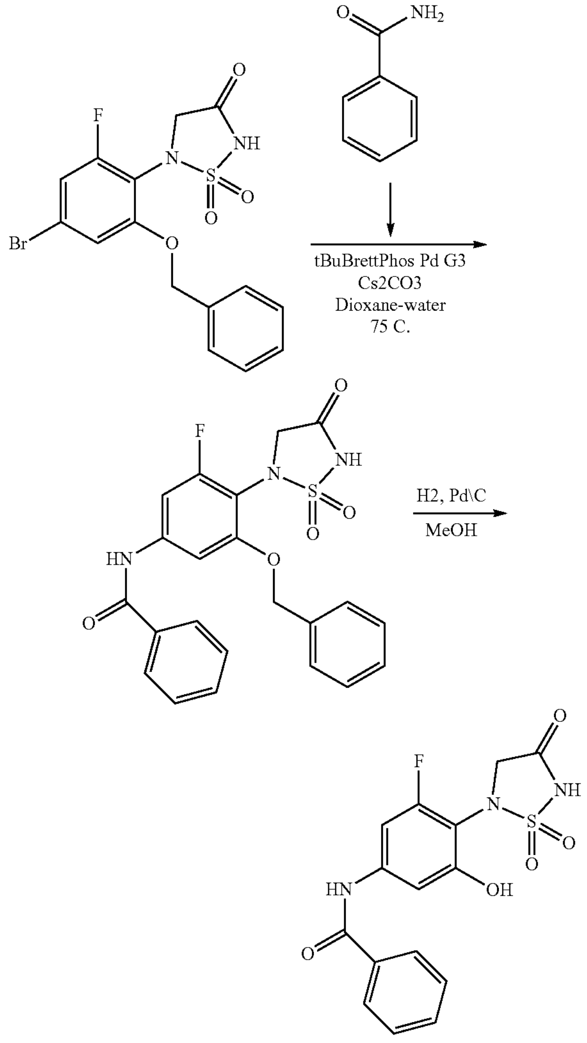

Step A: 5-[3-(benzyloxy)-5-fluoro-3'-methoxybiphenyl-4-yl]-1,2,5-thiadiazolidin-3-one 1,1-dioxide A degassed mixture of (5-[2-(benzyloxy)-4-bromo-6-fluorophenyl]-1,2,5-thiadiazolidin-3-one 1,1-dioxide (100 mg, 0.24 mmol) (See Preparation 1), benzamide (35 mg, 0.29 mmol), $Cs_2CO_3$ (250 mg, 0.76 mmol), tBuBrettPhos Pd G3 (7 mg, 3.3 mol), dioxane (2 mL), $H_2O$ (0.2 mL), was stirred under argon atmosphere at 75° C. for 36 h, cooled, diluted with water, acidified with conc. HCl to pH 2, and partitioned between water (2 mL) and EtOAc (6 mL). The organic layer was separated, washed with brine, dried over anh. $Na_2SO_4$, and concentrated under reduced pressure. The residue was subjected to silica FC eluting with a mixture of HCOOH (0→10%) and DCM to afford 57 mg (52%) of the title compound.

Step B: 5-(3-fluoro-5-hydroxy-3'-methoxybiphenyl-4-yl)-1,2,5-thiadiazolidin-3-one 1,1-dioxide A mixture of the product from Step A (57 mg, 0.13 mmol), methanol (2 mL), and 10 $PdCl_2$ on charcoal (7 mg) was vigorously stirred under $H_2$ atmosphere for 3 h at ambient temperature until reaction complete (TLC monitoring) and filtered through Celite pad. The filtrate was concentrated under reduced pressure, and the residue after evaporation was subjected to reverse phase HPLC to afford 31 mg (65%) of the title compound.

Example 14: N-[4-(1,1-dioxido-4-oxo-1,2,5-thiadiazolidin-2-yl)-3-fluoro-5-hydroxyphenyl]-3,4-dimethoxybenzamide

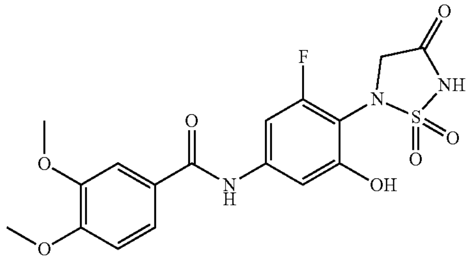 [SMILES: COc1ccc(C(=O)Nc2cc(O)c(N3CC(=O)NS3(=O)=O)c(F)c2)cc1OC]

The compound was synthesized according to the procedure described in Example 13 using 3,4-dimethoxybenzamide instead of benzamide.

Example 15: N-[4-(1,1-dioxido-4-oxo-1,2,5-thiadiazolidin-2-yl)-3-fluoro-5-hydroxyphenyl]-4-methoxybenzamide

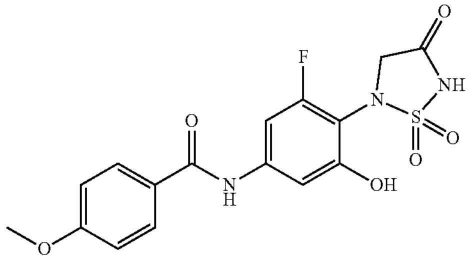 [SMILES: COc1ccc(C(=O)Nc2cc(O)c(N3CC(=O)NS3(=O)=O)c(F)c2)cc1]

The compound was synthesized according to the procedure described in Example 13 using 4-methoxybenzamide instead of benzamide.

Example 16: 4-tert-butyl-N-[4-(1,1-dioxido-4-oxo-1,2,5-thiadiazolidin-2-yl)-3-fluoro-5-hydroxyphenyl]benzamide

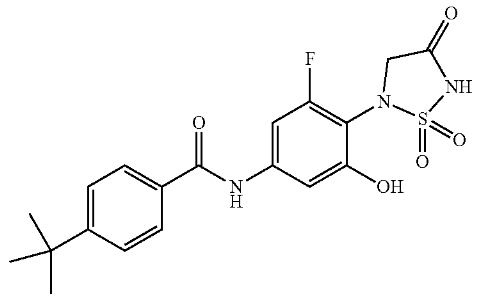 [SMILES: CC(C)(C)c1ccc(C(=O)Nc2cc(O)c(N3CC(=O)NS3(=O)=O)c(F)c2)cc1]

The compound was synthesized according to the procedure described in Example 13 using 4-tert-butylbenzamide instead of benzamide.

Example 17: N-[4-(1,1-dioxido-4-oxo-1,2,5-thiadiazolidin-2-yl)-3-fluoro-5-hydroxyphenyl]benzenesulfonamide

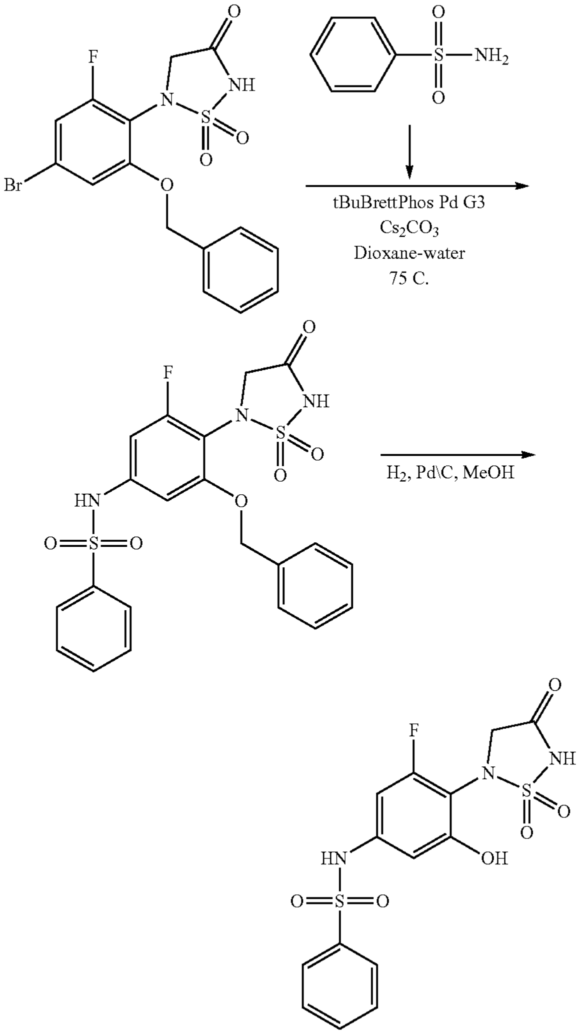

Step A: N-[3-(benzyloxy)-4-(1,1-dioxido-4-oxo-1,2,5-thiadiazolidin-2-yl)-5-fluorophenyl]benzenesulfonamide A degassed mixture of (5-[2-(benzyloxy)-4-bromo-6-fluorophenyl]-1,2,5-thiadiazolidin-3-one 1,1-dioxide (100 mg, 0.24 mmol) (See Preparation 1), benzenesulfonamide (45 mg, 0.29 mmol), $Cs_2CO_3$ (250 mg, 0.76 mmol), tBuBrettPhos Pd G3 (7 mg, 3.3 mol), dioxane (2 mL), $H_2O$ (0.2 mL), was stirred under argon atmosphere at 75° C. for 0.5 h, cooled, diluted with water, acidified with conc. HCl to pH 2, and partitioned between water (2 mL) and EtOAc (6 mL). The organic layer was separated, washed with brine, dried over anh. $Na_2SO_4$, and concentrated under reduced pressure. The residue was subjected to silica FC eluting with a mixture of MeOH (0→20%) and EtOAc to afford 57 mg (52%) of the title compound.

Step B: N-[4-(1,1-dioxido-4-oxo-1,2,5-thiadiazolidin-2-yl)-3-fluoro-5-hydroxyphenyl]benzenesulfonamide A mixture of the product from Step A (80 mg, 0.16 mmol), methanol (2 mL), and 10 $PdCl_2$ on charcoal (8 mg) was vigorously stirred under $H_2$ atmosphere for 3 h at ambient temperature until reaction complete (TLC monitoring) and filtered through Celite pad. The filtrate was concentrated under reduced pressure, and the residue after evaporation was subjected to reverse phase HPLC to afford 30 mg (46%) of the title compound.

Example 18: N-[4-(1,1-dioxido-4-oxo-1,2,5-thiadiazolidin-2-yl)-3-fluoro-5-hydroxyphenyl]-4-methylbenzenesulfonamide

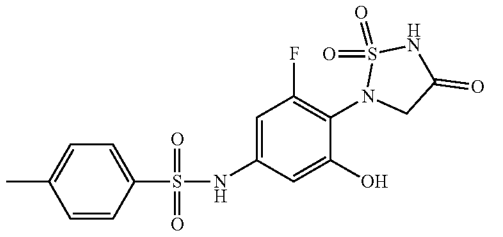 [SMILES: Cc1ccc(S(=O)(=O)Nc2cc(O)c(N3CC(=O)NS3(=O)=O)c(F)c2)cc1]

The compound was synthesized according to the procedure described in Example 17 using 4-methylbenzenesulfonamide instead of benzenesulfonamide.

Example 19: N-[4-(1,1-dioxido-4-oxo-1,2,5-thiadiazolidin-2-yl)-3-fluoro-5-hydroxyphenyl]-4-[5-(4-methylphenyl)-3-(trifluoromethyl)-1H-pyrazol-1-yl]benzenesulfonamide

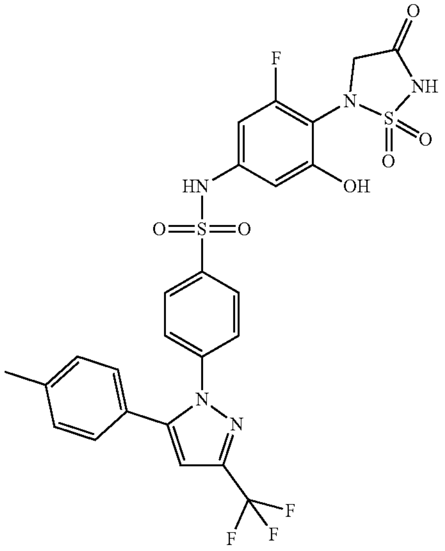 [SMILES: Cc1ccc(-c2cc(C(F)(F)F)nn2-c2ccc(S(=O)(=O)Nc3cc(O)c(N4CC(=O)NS4(=O)=O)c(F)c3)cc2)cc1]

The compound was synthesized according to the procedure described in Example 17 using 4-[5-(4-methylphenyl)-3-(trifluoromethyl)-1H-pyrazol-1-yl]benzenesulfonamide instead of benzenesulfonamide.

Example 20: N-[4-(1,1-dioxido-4-oxo-1,2,5-thiadiazolidin-2-yl)-3-fluoro-5-hydroxyphenyl]-4-fluorobenzenesulfonamide

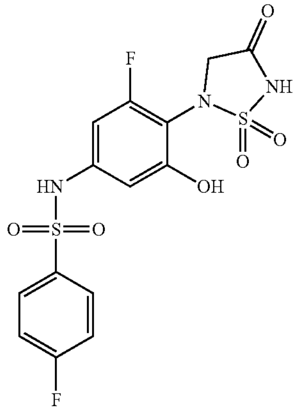 [SMILES: O=C1CN(c2c(O)cc(NS(=O)(=O)c3ccc(F)cc3)cc2F)S(=O)(=O)N1]

The compound was synthesized according to the procedure described in Example 17 using 4-fluorobenzenesulfonamide instead of benzenesulfonamide.

Example 21: N-[4-(1,1-dioxido-4-oxo-1,2,5-thiadiazolidin-2-yl)-3-fluoro-5-hydroxyphenyl]-2-fluorobenzenesulfonamide

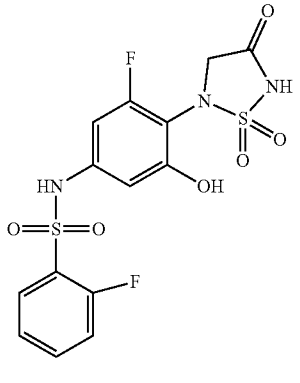 [SMILES: O=C1CN(c2c(O)cc(NS(=O)(=O)c3ccccc3F)cc2F)S(=O)(=O)N1]

The compound was synthesized according to the procedure described in Example 17 using 2-fluorobenzenesulfonamide instead of benzenesulfonamide.

Example 22: N-[4-(1,1-dioxido-4-oxo-1,2,5-thiadiazolidin-2-yl)-3-fluoro-5-hydroxyphenyl]-3-methylbenzenesulfonamide

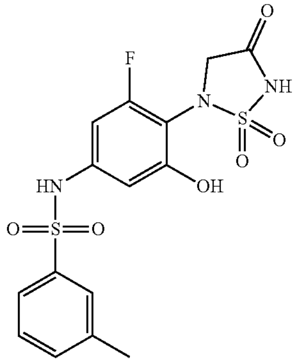 [SMILES: Cc1cccc(S(=O)(=O)Nc2cc(O)c(N3CC(=O)NS3(=O)=O)c(F)c2)c1]

The compound was synthesized according to the procedure described in Example 17 using 3-methylbenzenesulfonamide instead of benzenesulfonamide.

Example 23: N-[4-(1,1-dioxido-4-oxo-1,2,5-thiadiazolidin-2-yl)-3-fluoro-5-hydroxyphenyl]-2-methylbenzenesulfonamide

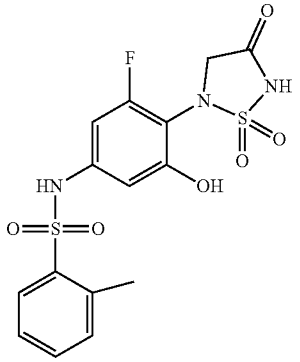 [SMILES: Cc1ccccc1S(=O)(=O)Nc1cc(O)c(N2CC(=O)NS2(=O)=O)c(F)c1]

The compound was synthesized according to the procedure described in Example 17 using 2-methylbenzenesulfonamide instead of benzenesulfonamide.

Example 24: 4-tert-butyl-N-[4-(1,1-dioxido-4-oxo-1,2,5-thiadiazolidin-2-yl)-3-fluoro-5-hydroxyphenyl]benzenesulfonamide

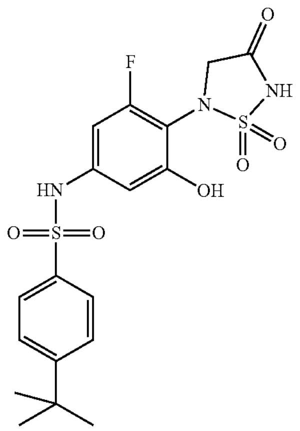 [SMILES: CC(C)(C)c1ccc(S(=O)(=O)Nc2cc(O)c(N3CC(=O)NS3(=O)=O)c(F)c2)cc1]

The compound was synthesized according to the procedure described in Example 17 using 4-tert-butylbenzenesulfonamide instead of benzenesulfonamide.

Example 25: N-[4-(1,1-dioxido-4-oxo-1,2,5-thiadiazolidin-2-yl)-3-fluoro-5-hydroxyphenyl]-4-methoxybenzenesulfonamide

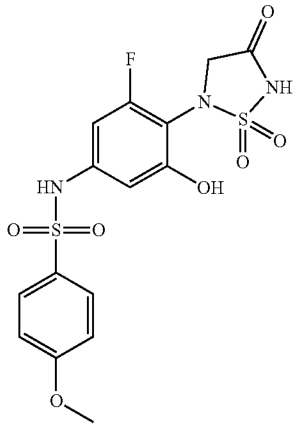 [SMILES: COc1ccc(S(=O)(=O)Nc2cc(O)c(N3CC(=O)NS3(=O)=O)c(F)c2)cc1]

The compound was synthesized according to the procedure described in Example 17 using 4-methoxybenzenesulfonamide instead of benzenesulfonamide.

Example 26: N-[4-(1,1-dioxido-4-oxo-1,2,5-thiadiazolidin-2-yl)-3-fluoro-5-hydroxyphenyl]-3,4-dimethoxybenzenesulfonamide

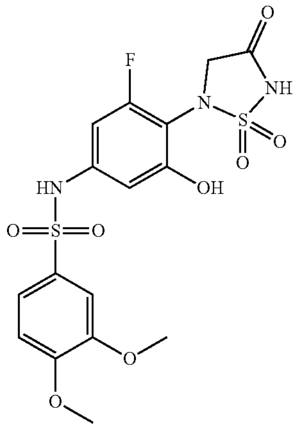 [SMILES: COc1ccc(S(=O)(=O)Nc2cc(O)c(N3CC(=O)NS3(=O)=O)c(F)c2)cc1OC]

The compound was synthesized according to the procedure described in Example 17 using 3,4-dimethoxybenzenesulfonamide instead of benzenesulfonamide.

Example 27: 1-(difluoromethyl)-N-[4-(1,1-dioxido-4-oxo-1,2,5-thiadiazolidin-2-yl)-3-fluoro-5-hydroxyphenyl]-5-methyl-1H-pyrazole-4-sulfonamide

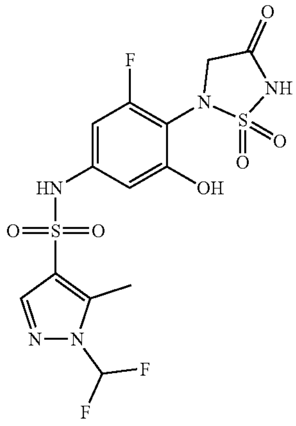 [SMILES: Cc1c(S(=O)(=O)Nc2cc(O)c(N3CC(=O)NS3(=O)=O)c(F)c2)cnn1C(F)F]

The compound was synthesized according to the procedure described in Example 17 using 1-(difluoromethyl)-5-methyl-1H-pyrazole-4-sulfonamide instead of benzenesulfonamide.

Example 28: N-[4-(1,1-dioxido-4-oxo-1,2,5-thiadiazolidin-2-yl)-3-fluoro-5-hydroxyphenyl]butane-1-sulfonamide

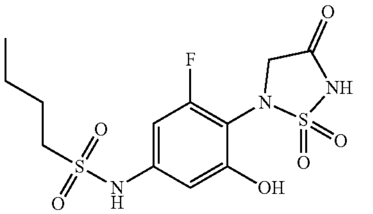 [SMILES: CCCCS(=O)(=O)Nc1cc(O)c(N2CC(=O)NS2(=O)=O)c(F)c1]

The compound was synthesized according to the procedure described in Example 17 using butane-1-sulfonamide instead of benzenesulfonamide.

Example 29: N-[4-(1,1-dioxido-4-oxo-1,2,5-thiadiazolidin-2-yl)-3-fluoro-5-hydroxyphenyl]-N'-phenylsulfuric diamide

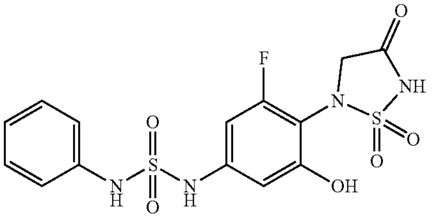 [SMILES: O=C1CN(c2c(O)cc(NS(=O)(=O)Nc3ccccc3)cc2F)S(=O)(=O)N1]

The compound was synthesized according to the procedure described in Example 17 using N-phenylsulfamide instead of benzenesulfonamide.

Example 30: N-{1-[(2-chlorobenzyl)sulfonyl]piperidin-4-yl}-N'-[4-(1,1-dioxido-4-oxo-1,2,5-thiadiazolidin-2-yl)-3-fluoro-5-hydroxyphenyl]sulfuric diamide

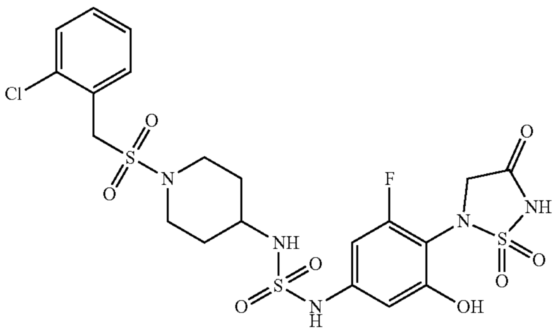 [SMILES: O=C1CN(c2c(O)cc(NS(=O)(=O)NC3CCN(S(=O)(=O)Cc4ccccc4Cl)CC3)cc2F)S(=O)(=O)N1]

The compound was synthesized according to the procedure described in Example 17 using N-{1-[(2-chlorobenzyl)sulfonyl]piperidin-4-yl}sulfamide instead of benzenesulfonamide.

Example 31: N'-[4-(1,1-dioxido-4-oxo-1,2,5-thiadiazolidin-2-yl)-3-fluoro-5-hydroxyphenyl]-N-methyl-N-phenylsulfuric diamide

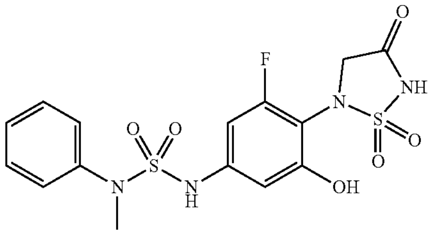 [SMILES: CN(c1ccccc1)S(=O)(=O)Nc1cc(O)c(N2CC(=O)NS2(=O)=O)c(F)c1]

The compound was synthesized according to the procedure described in Example 17 using N-methyl-N-phenylsulfamide instead of benzenesulfonamide.

Example 32: N-cyclohexyl-N'-[4-(1,1-dioxido-4-oxo-1,2,5-thiadiazolidin-2-yl)-3-fluoro-5-hydroxyphenyl]-N-methylsulfuric diamide

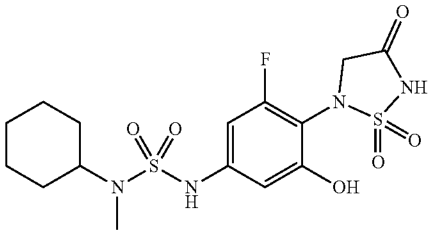 [SMILES: CN(C1CCCCC1)S(=O)(=O)Nc1cc(O)c(N2CC(=O)NS2(=O)=O)c(F)c1]

The compound was synthesized according to the procedure described in Example 17 using N-cyclohexyl-N-methylsulfamide instead of benzenesulfonamide.

Example 33: N-(3-chlorophenyl)-N'-[4-(1,1-dioxido-4-oxo-1,2,5-thiadiazolidin-2-yl)-3-fluoro-5-hydroxyphenyl]-N-methylsulfuric diamide

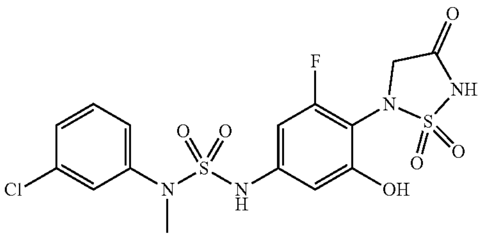 [SMILES: CN(c1cccc(Cl)c1)S(=O)(=O)Nc1cc(O)c(N2CC(=O)NS2(=O)=O)c(F)c1]

The compound was synthesized according to the procedure described in Example 17 using N-(3-chlorophenyl)-N-methylsulfamide instead of benzenesulfonamide.

Example 34: N-(3,4-dimethoxybenzyl)-N'-[4-(1,1-dioxido-4-oxo-1,2,5-thiadiazolidin-2-yl)-3-fluoro-5-hydroxyphenyl]-N-phenylsulfuric diamide

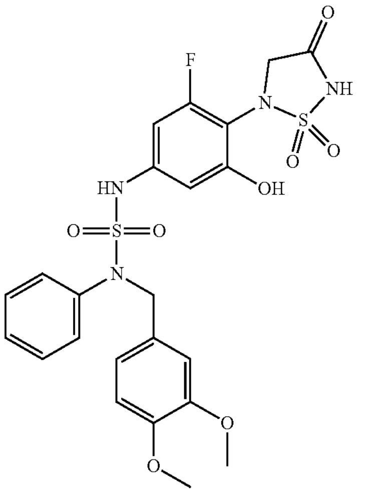 [SMILES: COc1ccc(CN(c2ccccc2)S(=O)(=O)Nc2cc(O)c(N3CC(=O)NS3(=O)=O)c(F)c2)cc1OC]

The compound was synthesized according to the procedure described in Example 17 using N-(3,4-dimethoxybenzyl)-N-phenylsulfamide instead of benzenesulfonamide.

Example 35: 1-[4-(1,1-dioxido-4-oxo-1,2,5-thiadiazolidin-2-yl)-3-fluoro-5-hydroxyphenyl]-3-phenylurea

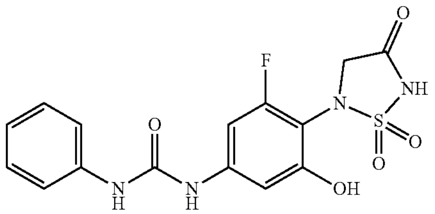 [SMILES: O=C1CN(c2c(O)cc(NC(=O)Nc3ccccc3)cc2F)S(=O)(=O)N1]

The compound was synthesized according to the procedure described in Example 17 using 1-phenylurea instead of benzenesulfonamide.

Example 36: 1-[4-(1,1-dioxido-4-oxo-1,2,5-thiadiazolidin-2-yl)-3-fluoro-5-hydroxyphenyl]-3-(4-methylphenyl)urea

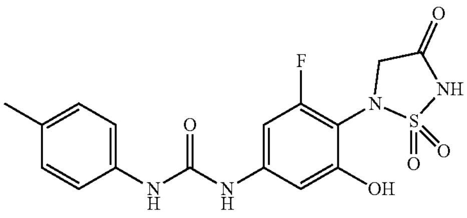 [SMILES: Cc1ccc(NC(=O)Nc2cc(O)c(N3CC(=O)NS3(=O)=O)c(F)c2)cc1]

The compound was synthesized according to the procedure described in Example 17 using 1-(4-methylphenyl)urea instead of benzenesulfonamide.

Example 37: 1-[4-(1,1-dioxido-4-oxo-1,2,5-thiadiazolidin-2-yl)-3-fluoro-5-hydroxyphenyl]-3-(4-methoxyphenyl)urea

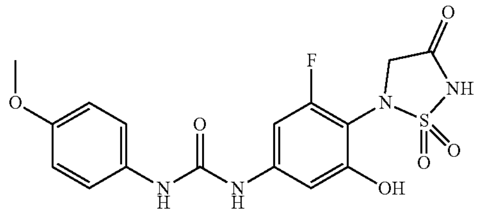 [SMILES: COc1ccc(NC(=O)Nc2cc(O)c(N3CC(=O)NS3(=O)=O)c(F)c2)cc1]

The compound was synthesized according to the procedure described in Example 17 using 1-(4-methoxyphenyl) urea instead of benzenesulfonamide.

Example 38: 1-[4-(1,1-dioxido-4-oxo-1,2,5-thiadiazolidin-2-yl)-3-fluoro-5-hydroxyphenyl]-3-[3-(trifluoromethyl)phenyl]urea

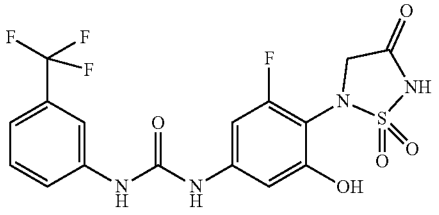 [SMILES: O=C1CN(c2c(O)cc(NC(=O)Nc3cccc(C(F)(F)F)c3)cc2F)S(=O)(=O)N1]

The compound was synthesized according to the procedure described in Example 17 using 1-[3-(trifluoromethyl) phenyl]urea instead of benzenesulfonamide.

Example 39: 1-[4-(1,1-dioxido-4-oxo-1,2,5-thiadiazolidin-2-yl)-3-fluoro-5-hydroxyphenyl]-3-(2-methylphenyl)urea

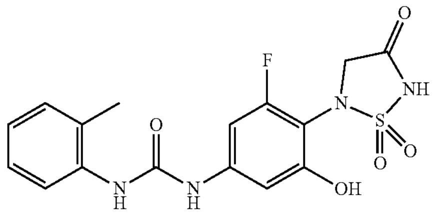 [SMILES: Cc1ccccc1NC(=O)Nc1cc(O)c(N2CC(=O)NS2(=O)=O)c(F)c1]

The compound was synthesized according to the procedure described in Example 17 using 1-(2-methylphenyl)urea instead of benzenesulfonamide.

Example 40: 1-[4-(1,1-dioxido-4-oxo-1,2,5-thiadiazolidin-2-yl)-3-fluoro-5-hydroxyphenyl]-3-(2-methoxyphenyl)urea

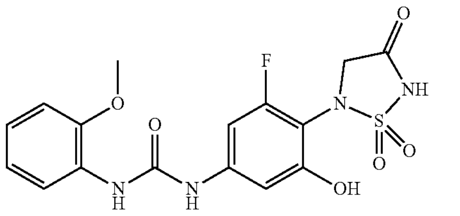 [SMILES: COc1ccccc1NC(=O)Nc1cc(O)c(N2CC(=O)NS2(=O)=O)c(F)c1]

The compound was synthesized according to the procedure described in Example 17 using 1-(2-methoxyphenyl) urea instead of benzenesulfonamide.

Example 41: 1-[4-(1,1-dioxido-4-oxo-1,2,5-thiadiazolidin-2-yl)-3-fluoro-5-hydroxyphenyl]-3-[4-(trifluoromethyl)phenyl]urea

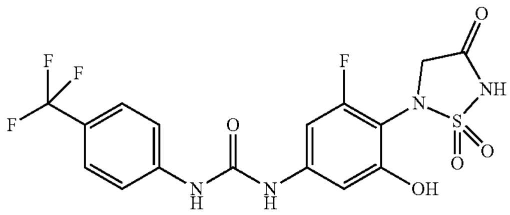 [SMILES: O=C1CN(c2c(O)cc(NC(=O)Nc3ccc(C(F)(F)F)cc3)cc2F)S(=O)(=O)N1]

The compound was synthesized according to the procedure described in Example 17 using 1-[4-(trifluoromethyl) phenyl]urea instead of benzenesulfonamide.

Example 42: 1-[4-(1,1-dioxido-4-oxo-1,2,5-thiadiazolidin-2-yl)-3-fluoro-5-hydroxyphenyl]-3-(3-methylphenyl)urea

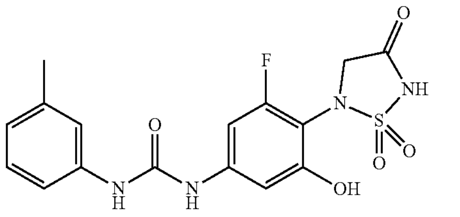 [SMILES: Cc1cccc(NC(=O)Nc2cc(O)c(N3CC(=O)NS3(=O)=O)c(F)c2)c1]

The compound was synthesized according to the procedure described in Example 17 using 1-(3-methylphenyl)urea instead of benzenesulfonamide.

Example 43: 1-[4-(1,1-dioxido-4-oxo-1,2,5-thiadiazolidin-2-yl)-3-fluoro-5-hydroxyphenyl]-3-(3-methoxyphenyl)urea

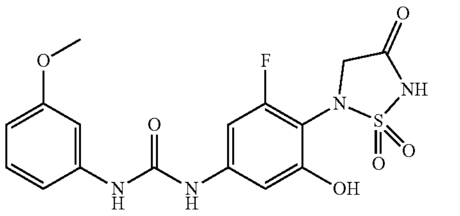 [SMILES: COc1cccc(NC(=O)Nc2cc(O)c(N3CC(=O)NS3(=O)=O)c(F)c2)c1]

The compound was synthesized according to the procedure described in Example 17 using 1-(3-methoxyphenyl) urea instead of benzenesulfonamide.

Example 44: 1-[4-(1,1-dioxido-4-oxo-1,2,5-thiadiazolidin-2-yl)-3-fluoro-5-hydroxyphenyl]-3-pyridin-4-ylurea

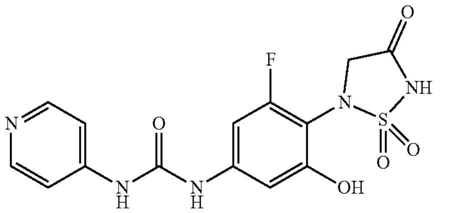 [SMILES: O=C1CN(c2c(O)cc(NC(=O)Nc3ccncc3)cc2F)S(=O)(=O)N1]

The compound was synthesized according to the procedure described in Example 17 using 1-pyridin-4-ylurea instead of benzenesulfonamide.

Example 45: 1-{1-[(2-chlorobenzyl)sulfonyl]piperidin-4-yl}-3-[4-(1,1-dioxido-4-oxo-1,2,5-thiadiazolidin-2-yl)-3-fluoro-5-hydroxyphenyl]urea

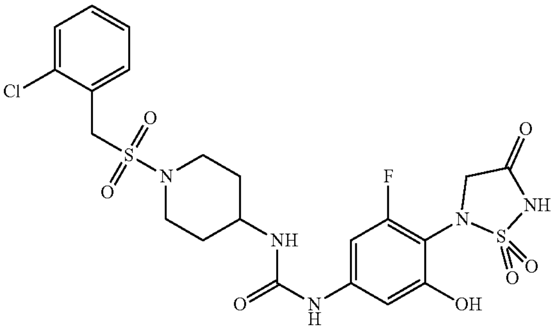 [SMILES: O=C1CN(c2c(O)cc(NC(=O)NC3CCN(S(=O)(=O)Cc4ccccc4Cl)CC3)cc2F)S(=O)(=O)N1]

The compound was synthesized according to the procedure described in Example 17 using 1-{1-[(2-chlorobenzyl) sulfonyl]piperidin-4-yl}urea instead of benzenesulfonamide.

Example 46: 1-(3-chlorophenyl)-3-[4-(1,1-dioxido-4-oxo-1,2,5-thiadiazolidin-2-yl)-3-fluoro-5-hydroxyphenyl]urea

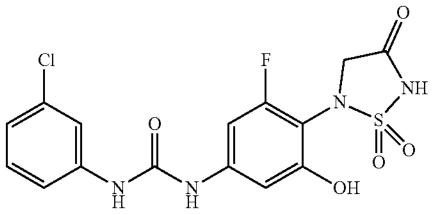 [SMILES: O=C1CN(c2c(O)cc(NC(=O)Nc3cccc(Cl)c3)cc2F)S(=O)(=O)N1]

The compound was synthesized according to the procedure described in Example 17 using 1-(3-chlorophenyl)urea instead of benzenesulfonamide.

Example 47: 1-(4-chlorophenyl)-3-[4-(1,1-dioxido-4-oxo-1,2,5-thiadiazolidin-2-yl)-3-fluoro-5-hydroxyphenyl]urea

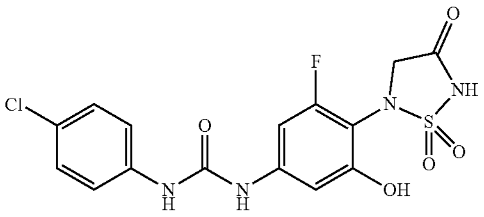 [SMILES: O=C1CN(c2c(O)cc(NC(=O)Nc3ccc(Cl)cc3)cc2F)S(=O)(=O)N1]

The compound was synthesized according to the procedure described in Example 17 using 1-(4-chlorophenyl)urea instead of benzenesulfonamide.

Example 48: 1-(2-chlorophenyl)-3-[4-(1,1-dioxido-4-oxo-1,2,5-thiadiazolidin-2-yl)-3-fluoro-5-hydroxyphenyl]urea

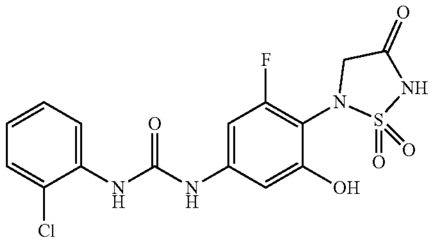 [SMILES: O=C1CN(c2c(O)cc(NC(=O)Nc3ccccc3Cl)cc2F)S(=O)(=O)N1]

The compound was synthesized according to the procedure described in Example 17 using 1-(2-chlorophenyl)urea instead of benzenesulfonamide.

Example 49: 1-(1H-benzimidazol-5-yl)-3-[4-(1,1-dioxido-4-oxo-1,2,5-thiadiazolidin-2-yl)-3-fluoro-5-hydroxyphenyl]urea

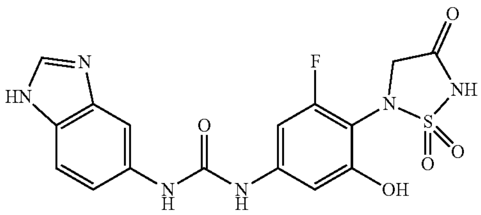 [SMILES: O=C1CN(c2c(O)cc(NC(=O)Nc3ccc4[nH]cnc4c3)cc2F)S(=O)(=O)N1]

The compound was synthesized according to the procedure described in Example 17 using 1-(1H-benzimidazol-5-yl)urea instead of benzenesulfonamide.

Example 50: 1-(3-tert-butyl-1-methyl-1H-pyrazol-5-yl)-3-[4-(1,1-dioxido-4-oxo-1,2,5-thiadiazolidin-2-yl)-3-fluoro-5-hydroxyphenyl]urea

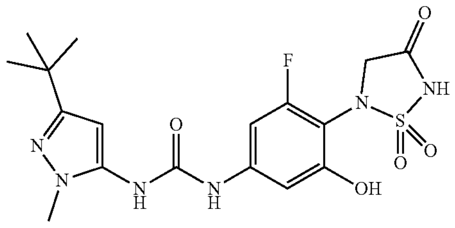 [SMILES: Cn1nc(C(C)(C)C)cc1NC(=O)Nc1cc(O)c(N2CC(=O)NS2(=O)=O)c(F)c1]

The compound was synthesized according to the procedure described in Example 17 using 1-(3-tert-butyl-1-methyl-1H-pyrazol-5-yl)urea instead of benzenesulfonamide.

Example 51: 1-{1-[(2-chlorophenyl)sulfonyl]piperidin-4-yl}-3-[4-(1,1-dioxido-4-oxo-1,2,5-thiadiazolidin-2-yl)-3-fluoro-5-hydroxyphenyl]urea

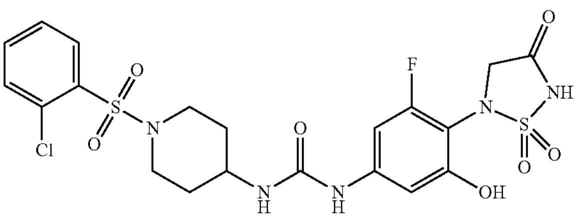 [SMILES: O=C1CN(c2c(O)cc(NC(=O)NC3CCN(S(=O)(=O)c4ccccc4Cl)CC3)cc2F)S(=O)(=O)N1]

The compound was synthesized according to the procedure described in Example 17 using 1-{1-[(2-chlorophenyl)sulfonyl]piperidin-4-yl}urea instead of benzenesulfonamide.

Example 52: 1-[4-(1,1-dioxido-4-oxo-1,2,5-thiadiazolidin-2-yl)-3-fluoro-5-hydroxyphenyl]-3-pyridin-3-ylurea

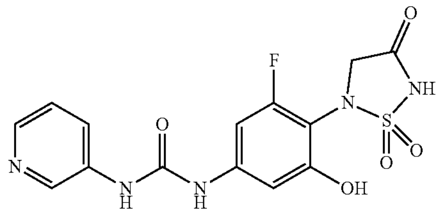 [SMILES: O=C1CN(c2c(O)cc(NC(=O)Nc3cccnc3)cc2F)S(=O)(=O)N1]

The compound was synthesized according to the procedure described in Example 17 using 1-pyridin-3-ylurea instead of benzenesulfonamide.

Example 53: 1-[4-(1,1-dioxido-4-oxo-1,2,5-thiadiazolidin-2-yl)-3-fluoro-5-hydroxyphenyl]-3-(4-fluorophenyl)urea

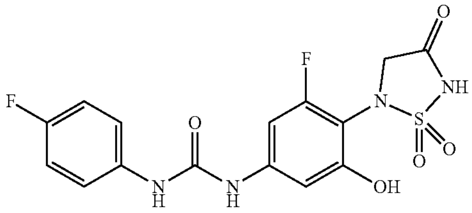 [SMILES: O=C1CN(c2c(O)cc(NC(=O)Nc3ccc(F)cc3)cc2F)S(=O)(=O)N1]

The compound was synthesized according to the procedure described in Example 17 using 1-(4-fluorophenyl)urea instead of benzenesulfonamide.

Example 54: 1-[4-(1,1-dioxido-4-oxo-1,2,5-thiadiazolidin-2-yl)-3-fluoro-5-hydroxyphenyl]-3-(3-fluorophenyl)urea

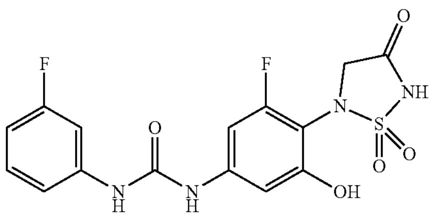

The compound was synthesized according to the procedure described in Example 17 using 1-(3-fluorophenyl)urea instead of benzenesulfonamide.

Example 55: 1-[4-(1,1-dioxido-4-oxo-1,2,5-thiadiazolidin-2-yl)-3-fluoro-5-hydroxyphenyl]-3-[2-(trifluoromethyl)phenyl]urea

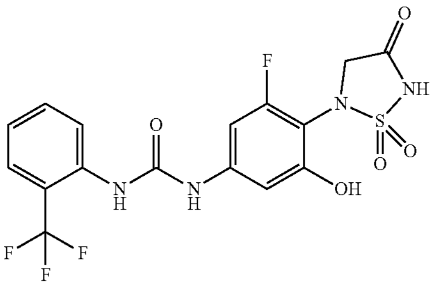 [SMILES: O=C1CN(c2c(O)cc(NC(=O)Nc3ccccc3C(F)(F)F)cc2F)S(=O)(=O)N1]

The compound was synthesized according to the procedure described in Example 17 using 1-[2-(trifluoromethyl)phenyl]urea instead of benzenesulfonamide.

Example 56: 1-cyclohexyl-3-[4-(1,1-dioxido-4-oxo-1,2,5-thiadiazolidin-2-yl)-3-fluoro-5-hydroxyphenyl]urea

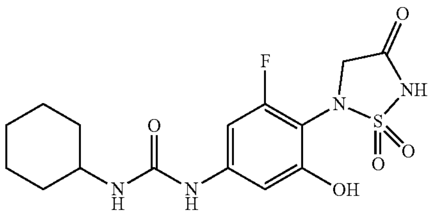 [SMILES: O=C1CN(c2c(O)cc(NC(=O)NC3CCCCC3)cc2F)S(=O)(=O)N1]

The compound was synthesized according to the procedure described in Example 17 using 1-cyclohexylurea instead of benzenesulfonamide.

Example 57: 1-[4-(1,1-dioxido-4-oxo-1,2,5-thiadiazolidin-2-yl)-3-fluoro-5-hydroxyphenyl]-3-(tetrahydrofuran-2-ylmethyl)urea

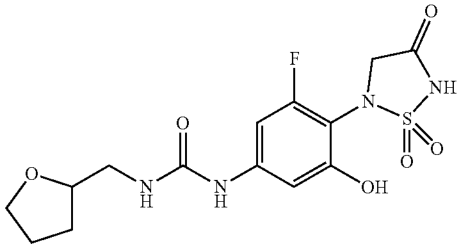 [SMILES: O=C1CN(c2c(O)cc(NC(=O)NCC3CCCO3)cc2F)S(=O)(=O)N1]

The compound was synthesized according to the procedure described in Example 17 using 1-(tetrahydrofuran-2-ylmethyl)urea instead of benzenesulfonamide.

Example 58: 1-[4-(1,1-dioxido-4-oxo-1,2,5-thiadiazolidin-2-yl)-3-fluoro-5-hydroxyphenyl]-3-(3-methoxypropyl)urea

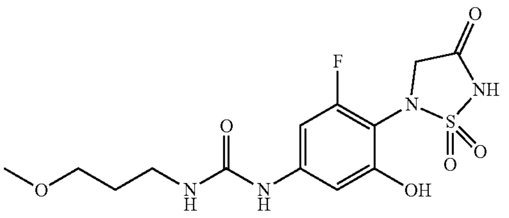 [SMILES: COCCCNC(=O)Nc1cc(O)c(N2CC(=O)NS2(=O)=O)c(F)c1]

The compound was synthesized according to the procedure described in Example 17 using 1-(3-methoxypropyl) urea instead of benzenesulfonamide.

Example 59: 1-(3,4-dimethoxyphenyl)-3-[4-(1,1-dioxido-4-oxo-1,2,5-thiadiazolidin-2-yl)-3-fluoro-5-hydroxyphenyl]urea

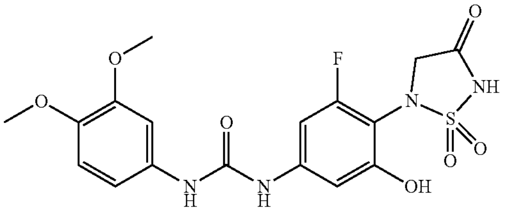 [SMILES: COc1ccc(NC(=O)Nc2cc(O)c(N3CC(=O)NS3(=O)=O)c(F)c2)cc1OC]

The compound was synthesized according to the procedure described in Example 17 using 1-(3,4-dimethoxyphenyl)urea instead of benzenesulfonamide.

Example 60: 1-benzyl-3-[4-(1,1-dioxido-4-oxo-1,2,5-thiadiazolidin-2-yl)-3-fluoro-5-hydroxyphenyl]urea

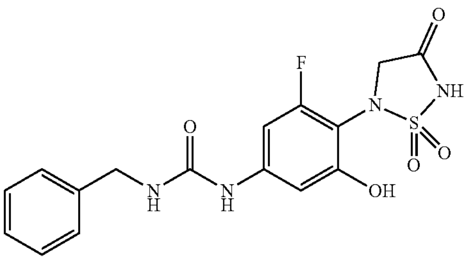 [SMILES: O=C1CN(c2c(O)cc(NC(=O)NCc3ccccc3)cc2F)S(=O)(=O)N1]

The compound was synthesized according to the procedure described in Example 17 using 1-benzylurea instead of benzenesulfonamide.

Example 61: 1-[4-(1,1-dioxido-4-oxo-1,2,5-thiadiazolidin-2-yl)-3-fluoro-5-hydroxyphenyl]-3-tricyclo[3.3.1.1$^{3,7}$]dec-1-ylurea

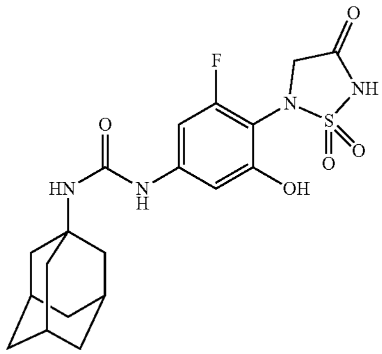 [SMILES: O=C1CN(c2c(O)cc(NC(=O)NC34CC5CC(CC(C5)C3)C4)cc2F)S(=O)(=O)N1]

The compound was synthesized according to the procedure described in Example 17 using 1-tricyclo[3.3.1.1$^{3,7}$]dec-1-ylurea instead of benzenesulfonamide.

Example 62: 1-[4-(1,1-dioxido-4-oxo-1,2,5-thiadiazolidin-2-yl)-3-fluoro-5-hydroxyphenyl]-3-(3-methylbutyl)urea

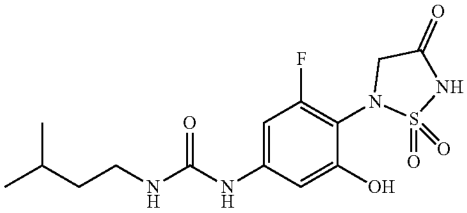 [SMILES: CC(C)CCNC(=O)Nc1cc(O)c(N2CC(=O)NS2(=O)=O)c(F)c1]

The compound was synthesized according to the procedure described in Example 17 using 1-(3-methylbutyl)urea instead of benzenesulfonamide.

Example 63: 1-[4-(1,1-dioxido-4-oxo-1,2,5-thiadiazolidin-2-yl)-3-fluoro-5-hydroxyphenyl]-3-(4-methoxybenzyl)urea

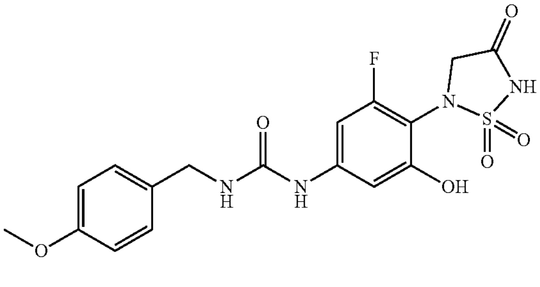 [SMILES: COc1ccc(CNC(=O)Nc2cc(O)c(N3CC(=O)NS3(=O)=O)c(F)c2)cc1]

The compound was synthesized according to the procedure described in Example 17 using 1-(4-methoxybenzyl) urea instead of benzenesulfonamide.

Example 64: 1-[1-(2-chlorobenzyl)-1H-pyrazol-4-yl]-3-[4-(1,1-dioxido-4-oxo-1,2,5-thiadiazolidin-2-yl)-3-fluoro-5-hydroxyphenyl]urea

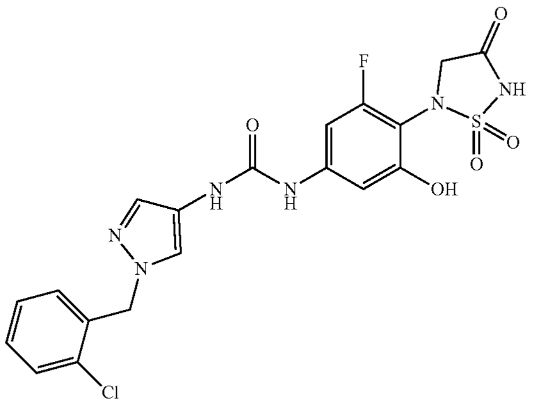 [SMILES: O=C1CN(c2c(O)cc(NC(=O)Nc3cnn(Cc4ccccc4Cl)c3)cc2F)S(=O)(=O)N1]

The compound was synthesized according to the procedure described in Example 17 using 1-[1-(2-chlorobenzyl)-1H-pyrazol-4-yl]urea instead of benzenesulfonamide.

Example 65: 1-[4-(1,1-dioxido-4-oxo-1,2,5-thiadiazolidin-2-yl)-3-fluoro-5-hydroxyphenyl]-3-[4-(morpholin-4-yl)phenyl]urea

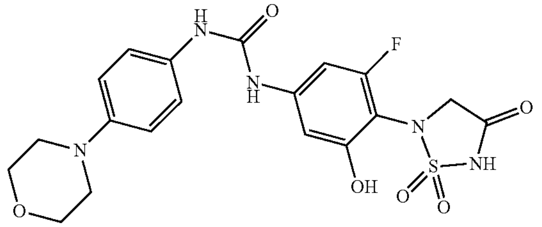 [SMILES: O=C1CN(c2c(O)cc(NC(=O)Nc3ccc(N4CCOCC4)cc3)cc2F)S(=O)(=O)N1]

The compound was synthesized according to the procedure described in Example 17 using 1-(4-morpholin-4-ylphenyl)urea instead of benzenesulfonamide.

Example 66: tert-butyl 4-[4-({[4-(1,1-dioxido-4-oxo-1,2,5-thiadiazolidin-2-yl)-3-fluoro-5-hydroxyphenyl]carbamoyl}amino)phenyl]piperazine-1-carboxylate

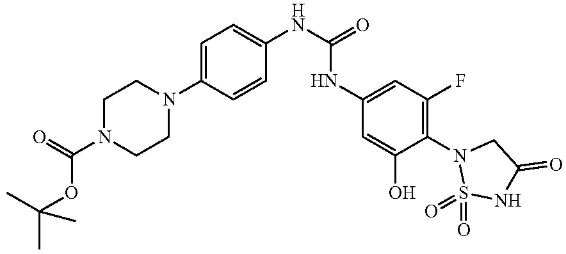 [SMILES: CC(C)(C)OC(=O)N1CCN(c2ccc(NC(=O)Nc3cc(O)c(N4CC(=O)NS4(=O)=O)c(F)c3)cc2)CC1]

The compound was synthesized according to the procedure described in Example 17 using tert-butyl 4-[4-(carbamoylamino)phenyl]piperazine-1-carboxylate instead of benzenesulfonamide.

Example 67: 1-[4-(1,1-dioxido-4-oxo-1,2,5-thiadiazolidin-2-yl)-3-fluoro-5-hydroxyphenyl]-3-[4-(piperazin-1-yl)phenyl]urea hydrochloride

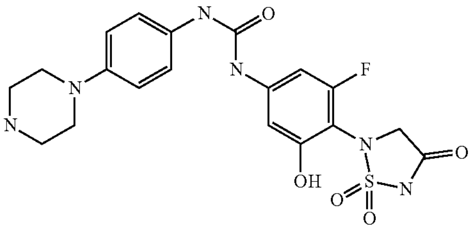 [SMILES: O=C1CN(c2c(O)cc(NC(=O)Nc3ccc(N4CCNCC4)cc3)cc2F)S(=O)(=O)N1]

A stirring solution of tert-butyl 4-[4-({[4-(1,1-dioxido-4-oxo-1,2,5-thiadiazolidin-2-yl)-3-fluoro-5-hydroxyphenyl]carbamoyl}amino)phenyl]piperazine-1-carboxylate (see Example 66) in DCM was treated with an excess of 6N solution of HCl in dioxane. The mixture was stirred at ambient temperature for 3 h and concentrated under reduced pressure. The residue was treated with EtOAc, formed precipitate was separated by centrifugation, washed twice with EtOAc followed by centrifugation each time, and dried under reduced pressure to afford the title compound in 92% yield.

Example 68: 1-[4-(1,1-dioxido-4-oxo-1,2,5-thiadiazolidin-2-yl)-3-fluoro-5-hydroxyphenyl]-3-[4-methoxy-3-(trifluoromethyl)phenyl]urea

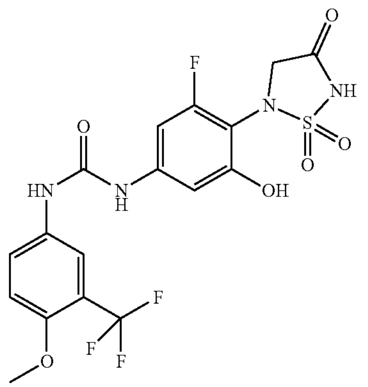 [SMILES: COc1ccc(NC(=O)Nc2cc(O)c(N3CC(=O)NS3(=O)=O)c(F)c2)cc1C(F)(F)F]

The compound was synthesized according to the procedure described in Example 17 using 1-[4-methoxy-3-(trifluoromethyl)phenyl]urea instead of benzenesulfonamide.

Example 69: 1-[4-(1,1-dioxido-4-oxo-1,2,5-thiadiazolidin-2-yl)-3-fluoro-5-hydroxyphenyl]-3-[4-(methylsulfonyl)phenyl]urea

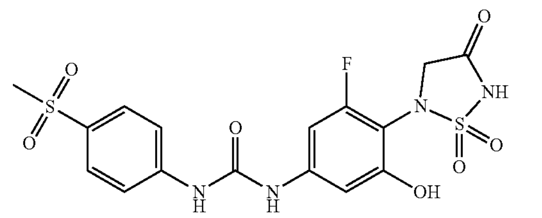 [SMILES: CS(=O)(=O)c1ccc(NC(=O)Nc2cc(O)c(N3CC(=O)NS3(=O)=O)c(F)c2)cc1]

The compound was synthesized according to the procedure described in Example 17 using 1-[4-(methylsulfonyl)phenyl]urea instead of benzenesulfonamide.

Example 70: 1-[4-(1,1-dioxido-4-oxo-1,2,5-thiadiazolidin-2-yl)-3-fluoro-5-hydroxyphenyl]-3-[4-(propan-2-yl)phenyl]urea

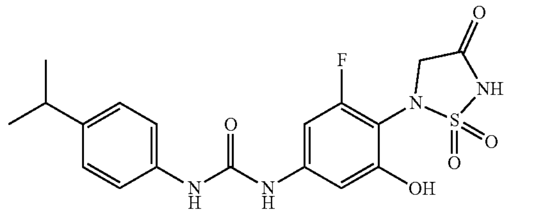 [SMILES: CC(C)c1ccc(NC(=O)Nc2cc(O)c(N3CC(=O)NS3(=O)=O)c(F)c2)cc1]

The compound was synthesized according to the procedure described in Example 17 using 1-[4-(1-methylethyl)phenyl]urea instead of benzenesulfonamide.

Example 71: 1-[4-(1,1-dioxido-4-oxo-1,2,5-thiadiazolidin-2-yl)-3-fluoro-5-hydroxyphenyl]-3-[4-(trifluoromethoxy)phenyl]urea

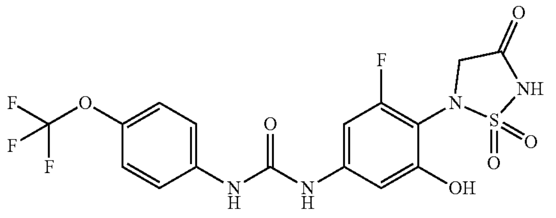 [SMILES: O=C1CN(c2c(O)cc(NC(=O)Nc3ccc(OC(F)(F)F)cc3)cc2F)S(=O)(=O)N1]

The compound was synthesized according to the procedure described in Example 17 using 1-[4-(trifluoromethoxy)phenyl]urea instead of benzenesulfonamide.

Example 72: 1-[4-(1,1-dioxido-4-oxo-1,2,5-thiadiazolidin-2-yl)-3-fluoro-5-hydroxyphenyl]-3-(1-methylpiperidin-4-yl)urea

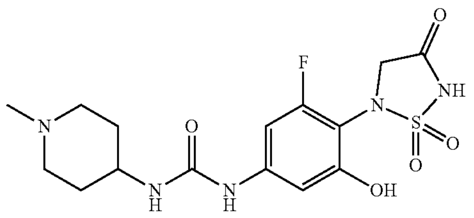

The compound was synthesized according to the procedure described in Example 17 using 1-(1-methylpiperidin-4-yl)urea instead of benzenesulfonamide.

Example 73: N-[4-(1,1-dioxido-4-oxo-1,2,5-thiadiazolidin-2-yl)-3-fluoro-5-hydroxyphenyl]-3,4-dihydroquinoline-1(2H)-carboxamide

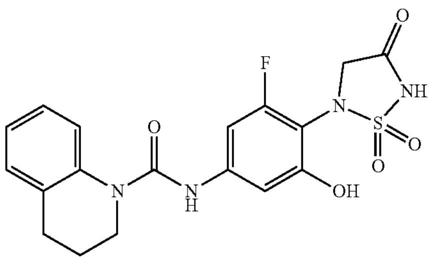 [SMILES: O=C1CN(c2c(O)cc(NC(=O)N3CCCc4ccccc43)cc2F)S(=O)(=O)N1]

The compound was synthesized according to the procedure described in Example 17 using 3,4-dihydroquinoline-1(2H)-carboxamide instead of benzenesulfonamide.

Example 74: N-[4-(1,1-dioxido-4-oxo-1,2,5-thiadiazolidin-2-yl)-3-fluoro-5-hydroxyphenyl]-3,4-dihydroisoquinoline-2(1H)-carboxamide

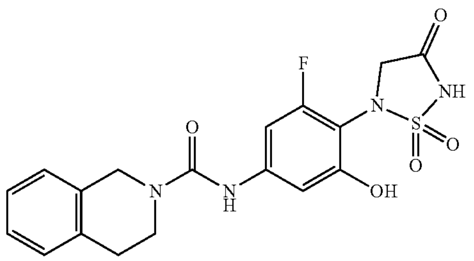 [SMILES: O=C1CN(c2c(O)cc(NC(=O)N3CCc4ccccc4C3)cc2F)S(=O)(=O)N1]

The compound was synthesized according to the procedure described in Example 17 using 3,4-dihydroisoquinoline-2(1H)-carboxamide instead of benzenesulfonamide.

Example 75: (3S)—N-[4-(1,1-dioxido-4-oxo-1,2,5-thiadiazolidin-2-yl)-3-fluoro-5-hydroxyphenyl]-3-(morpholin-4-ylmethyl)-3,4-dihydroisoquinoline-2(1H)-carboxamide

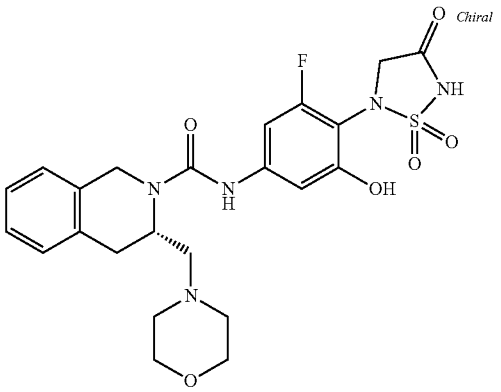 [SMILES: O=C1CN(c2c(O)cc(NC(=O)N3Cc4ccccc4C[C@H]3CN3CCOCC3)cc2F)S(=O)(=O)N1]

The compound was synthesized according to the procedure described in Example 17 using (3S)-3-(morpholin-4-ylmethyl)-3,4-dihydroisoquinoline-2(1H)-carboxamide instead of benzenesulfonamide.

Example 76: 3-[4-(1,1-dioxido-4-oxo-1,2,5-thiadiazolidin-2-yl)-3-fluoro-5-hydroxyphenyl]-1-methyl-1-phenylurea

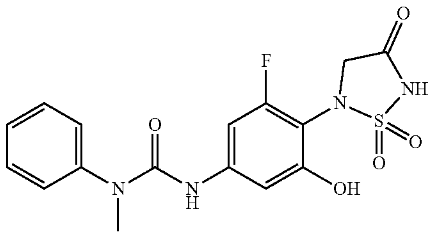 [SMILES: CN(C(=O)Nc1cc(O)c(N2CC(=O)NS2(=O)=O)c(F)c1)c1ccccc1]

The compound was synthesized according to the procedure described in Example 17 using 1-methyl-1-phenylurea instead of benzenesulfonamide.

Example 77: 1-[4-(1,1-dioxido-4-oxo-1,2,5-thiadiazolidin-2-yl)-3-fluoro-5-hydroxyphenyl]-3-(1-methyl-1,2,3,4-tetrahydroquinolin-7-yl)urea

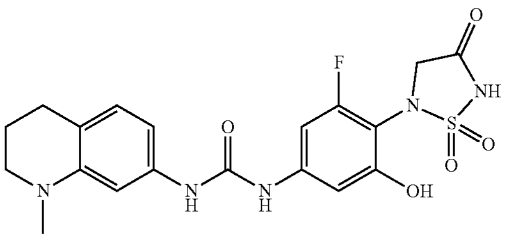 [SMILES: CN1CCCc2ccc(NC(=O)Nc3cc(O)c(N4CC(=O)NS4(=O)=O)c(F)c3)cc21]

The compound was synthesized according to the procedure described in Example 17 using 1-(1-methyl-1,2,3,4-tetrahydroquinolin-7-yl)urea instead of benzenesulfonamide.

Example 78: N-[4-(1,1-dioxido-4-oxo-1,2,5-thiadiazolidin-2-yl)-3-fluoro-5-hydroxyphenyl]pyridin-3-sulfonamide

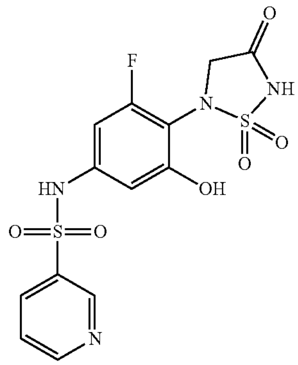 [SMILES: O=C1CN(c2c(O)cc(NS(=O)(=O)c3cccnc3)cc2F)S(=O)(=O)N1]

The compound was synthesized according to the procedure described in Example 17 using pyridine-3-sulfonamide instead of benzenesulfonamide.

Example 79: 4-chloro-N-[4-(1,1-dioxido-4-oxo-1,2,5-thiadiazolidin-2-yl)-3-fluoro-5-hydroxyphenyl]benzenesulfonamide

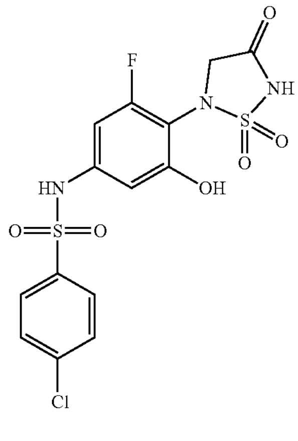

The compound was synthesized according to the procedure described in Example 17 using 4-chlorobenzenesulfonamide instead of benzenesulfonamide.

Example 80: methyl 2-{[4-(1,1-dioxido-4-oxo-1,2,5-thiadiazolidin-2-yl)-3-fluoro-5-hydroxyphenyl]sulfamoyl}benzoate

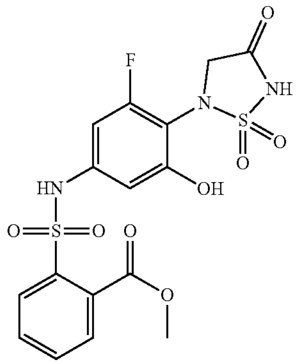 [SMILES: COC(=O)c1ccccc1S(=O)(=O)Nc1cc(O)c(N2CC(=O)NS2(=O)=O)c(F)c1]

The compound was synthesized according to the procedure described in Example 17 using methyl 2-sulfamoylbenzoate instead of benzenesulfonamide.

Example 81: N-[4-(1,1-dioxido-4-oxo-1,2,5-thiadiazolidin-2-yl)-3-fluoro-5-hydroxyphenyl]-3-fluorobenzenesulfonamide

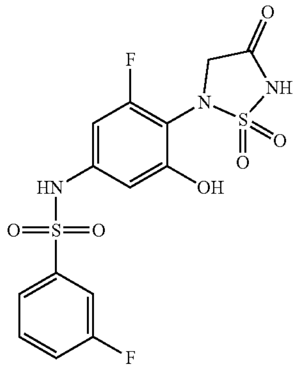 [SMILES: O=C1CN(c2c(O)cc(NS(=O)(=O)c3cccc(F)c3)cc2F)S(=O)(=O)N1]

The compound was synthesized according to the procedure described in Example 17 using 3-fluorobenzenesulfonamide instead of benzenesulfonamide.

Example 82: 3-chloro-N-[4-(1,1-dioxido-4-oxo-1,2,5-thiadiazolidin-2-yl)-3-fluoro-5-hydroxyphenyl]benzenesulfonamide

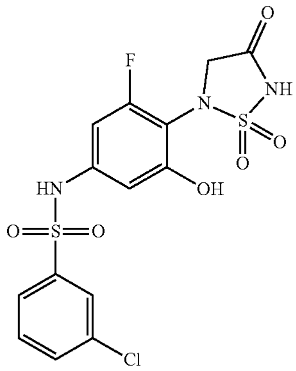 [SMILES: O=C1CN(c2c(O)cc(NS(=O)(=O)c3cccc(Cl)c3)cc2F)S(=O)(=O)N1]

The compound was synthesized according to the procedure described in Example 17 using 3-chlorobenzenesulfonamide instead of benzenesulfonamide.

Example 83: N-[4-(1,1-dioxido-4-oxo-1,2,5-thiadiazolidin-2-yl)-3-fluoro-5-hydroxyphenyl]-4-(trifluoromethyl)benzenesulfonamide

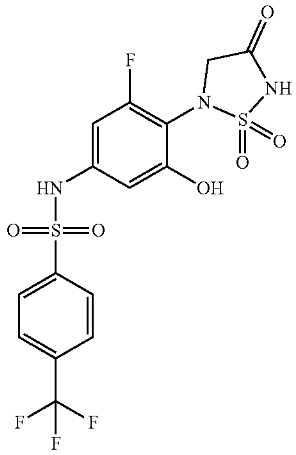 [SMILES: O=C1CN(c2c(O)cc(NS(=O)(=O)c3ccc(C(F)(F)F)cc3)cc2F)S(=O)(=O)N1]

The compound was synthesized according to the procedure described in Example 17 using 4-(trifluoromethyl)benzenesulfonamide instead of benzenesulfonamide.

Example 84: N-[4-(1,1-dioxido-4-oxo-1,2,5-thiadiazolidin-2-yl)-3-fluoro-5-hydroxyphenyl]-3-(trifluoromethyl)benzenesulfonamide

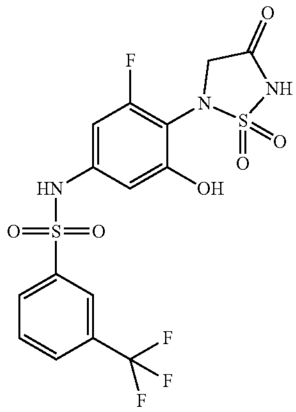 [SMILES: O=C1CN(c2c(O)cc(NS(=O)(=O)c3cccc(C(F)(F)F)c3)cc2F)S(=O)(=O)N1]

The compound was synthesized according to the procedure described in Example 17 using 3-(trifluoromethyl) benzenesulfonamide instead of benzenesulfonamide.

Example 85: N-[4-(1,1-dioxido-4-oxo-1,2,5-thiadiazolidin-2-yl)-3-fluoro-5-hydroxyphenyl]-1-phenylmethanesulfonamide

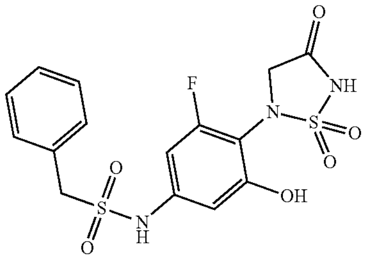 [SMILES: O=C1CN(c2c(O)cc(NS(=O)(=O)Cc3ccccc3)cc2F)S(=O)(=O)N1]

The compound was synthesized according to the procedure described in Example 17 using 1-phenylmethanesulfonamide instead of benzenesulfonamide.

Example 86: N-[4-(1,1-dioxido-4-oxo-1,2,5-thiadiazolidin-2-yl)-3-fluoro-5-hydroxyphenyl]cyclopropanesulfonamide

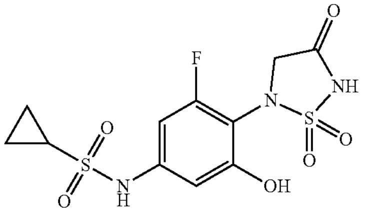 [SMILES: O=C1CN(c2c(O)cc(NS(=O)(=O)C3CC3)cc2F)S(=O)(=O)N1]

The compound was synthesized according to the procedure described in Example 17 using cyclopropanesulfonamide instead of benzenesulfonamide.

Example 87: N-[4-(1,1-dioxido-4-oxo-1,2,5-thiadiazolidin-2-yl)-3-fluoro-5-hydroxyphenyl]propane-2-sulfonamide

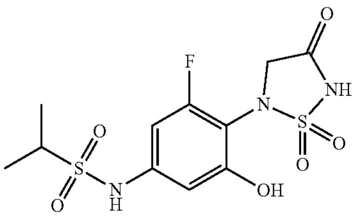 [SMILES: CC(C)S(=O)(=O)Nc1cc(O)c(N2CC(=O)NS2(=O)=O)c(F)c1]

The compound was synthesized according to the procedure described in Example 17 using propane-2-sulfonamide instead of benzenesulfonamide.

Example 88: 1-cyclopentyl-3-[4-(1,1-dioxido-4-oxo-1,2,5-thiadiazolidin-2-yl)-3-fluoro-5-hydroxyphenyl] urea

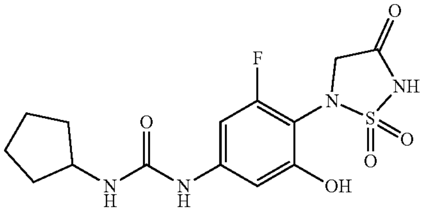 [SMILES: O=C1CN(c2c(O)cc(NC(=O)NC3CCCC3)cc2F)S(=O)(=O)N1]

The compound was synthesized according to the procedure described in Example 17 using 1-cyclopentylurea instead of benzenesulfonamide.

Example 89: 1-[4-(1,1-dioxido-4-oxo-1,2,5-thiadiazolidin-2-yl)-3-fluoro-5-hydroxyphenyl]-3-(4-methylcyclohexyl)urea

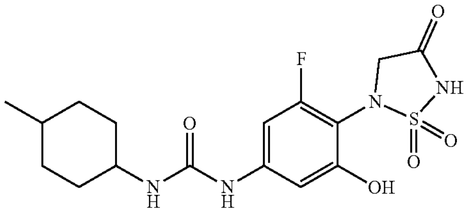 [SMILES: CC1CCC(NC(=O)Nc2cc(O)c(N3CC(=O)NS3(=O)=O)c(F)c2)CC1]

The compound was synthesized according to the procedure described in Example 17 using 1-(4-methylcyclohexyl) urea instead of benzenesulfonamide.

Example 90: 1-(4-tert-butylcyclohexyl)-3-[4-(1,1-dioxido-4-oxo-1,2,5-thiadiazolidin-2-yl)-3-fluoro-5-hydroxyphenyl]urea

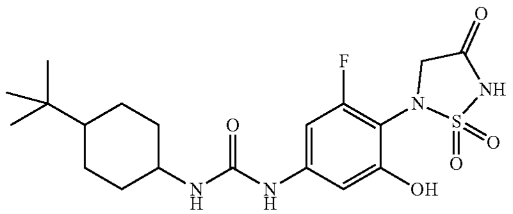 [SMILES: CC(C)(C)C1CCC(NC(=O)Nc2cc(O)c(N3CC(=O)NS3(=O)=O)c(F)c2)CC1]

The compound was synthesized according to the procedure described in Example 17 using 1-(4-tert-butylcyclohexyl)urea instead of benzenesulfonamide.

Example 91: 1-[4-(1,1-dioxido-4-oxo-1,2,5-thiadiazolidin-2-yl)-3-fluoro-5-hydroxyphenyl]-3-(trans-4-hydroxycyclohexyl)urea

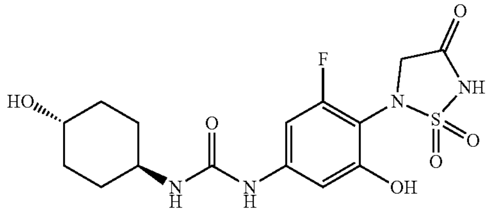 [SMILES: O=C1CN(c2c(O)cc(NC(=O)N[C@H]3CC[C@H](O)CC3)cc2F)S(=O)(=O)N1]

The compound was synthesized according to the procedure described in Example 17 using 1-(trans-4-hydroxycyclohexyl)urea instead of benzenesulfonamide.

Example 92: 1-cycloheptyl-3-[4-(1,1-dioxido-4-oxo-1,2,5-thiadiazolidin-2-yl)-3-fluoro-5-hydroxyphenyl]urea

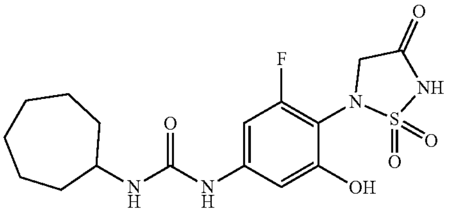 [SMILES: O=C1CN(c2c(O)cc(NC(=O)NC3CCCCCC3)cc2F)S(=O)(=O)N1]

The compound was synthesized according to the procedure described in Example 17 using 1-cycloheptylurea instead of benzenesulfonamide.

Example 93: 1-[4-(1,1-dioxido-4-oxo-1,2,5-thiadiazolidin-2-yl)-3-fluoro-5-hydroxyphenyl]-3-(2-fluorophenyl)urea

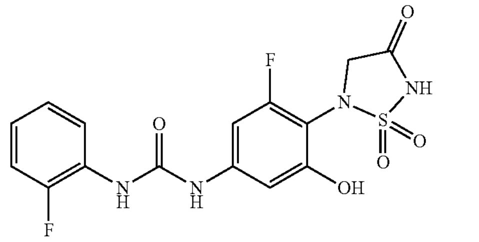 [SMILES: O=C1CN(c2c(O)cc(NC(=O)Nc3ccccc3F)cc2F)S(=O)(=O)N1]

The compound was synthesized according to the procedure described in Example 17 using 1-(2-fluorophenyl)urea instead of benzenesulfonamide.

Example 94: 1-[4-(1,1-dioxido-4-oxo-1,2,5-thiadiazolidin-2-yl)-3-fluoro-5-hydroxyphenyl]-3-[3-(piperidin-1-yl)propyl]urea

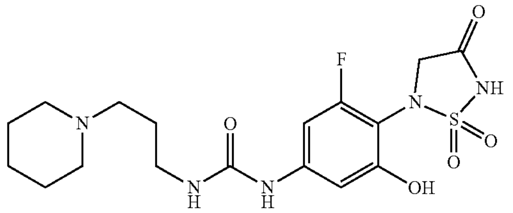 [SMILES: O=C1CN(c2c(O)cc(NC(=O)NCCCN3CCCCC3)cc2F)S(=O)(=O)N1]

The compound was synthesized according to the procedure described in Example 17 using 1-(3-piperidin-1-ylpropyl)urea instead of benzenesulfonamide.

Example 95: 1-[4-(1,1-dioxido-4-oxo-1,2,5-thiadiazolidin-2-yl)-3-fluoro-5-hydroxyphenyl]-3-[3-(morpholin-4-yl)propyl]urea

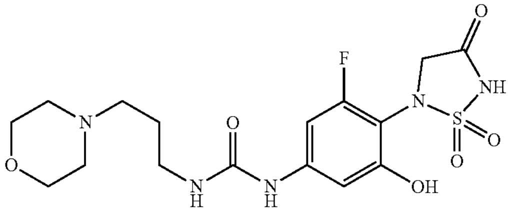 [SMILES: O=C1CN(c2c(O)cc(NC(=O)NCCCN3CCOCC3)cc2F)S(=O)(=O)N1]

The compound was synthesized according to the procedure described in Example 17 using 1-(3-morpholin-4-ylpropyl)urea instead of benzenesulfonamide.

Example 96: N'-[4-(1,1-dioxido-4-oxo-1,2,5-thiadiazolidin-2-yl)-3-fluoro-5-hydroxyphenyl]-N-(3-fluorophenyl)-N-methylsulfuric diamide

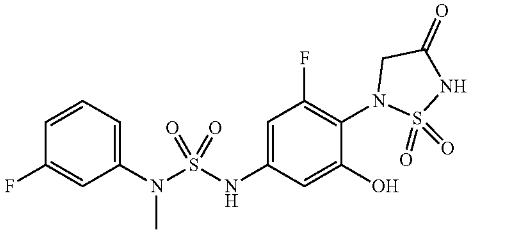 [SMILES: CN(c1cccc(F)c1)S(=O)(=O)Nc1cc(O)c(N2CC(=O)NS2(=O)=O)c(F)c1]

The compound was synthesized according to the procedure described in Example 17 using N-(3-fluorophenyl)-N-methylsulfamide instead of benzenesulfonamide.

Example 97: N'-[4-(1,1-dioxido-4-oxo-1,2,5-thiadiazolidin-2-yl)-3-fluoro-5-hydroxyphenyl]-N-(4-fluorophenyl)-N-methylsulfuric diamide

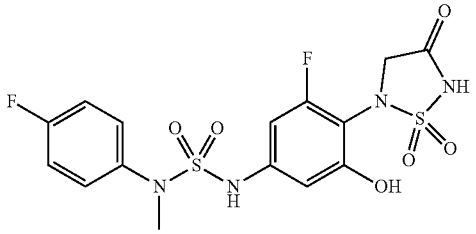 [SMILES: CN(c1ccc(F)cc1)S(=O)(=O)Nc1cc(O)c(N2CC(=O)NS2(=O)=O)c(F)c1]

The compound was synthesized according to the procedure described in Example 17 using N-(4-fluorophenyl)-N-methylsulfamide instead of benzenesulfonamide.

| | | | | MS (ESI) | | Purity (%) | |
|---|---|---|---|---|---|---|---|
| Example No. | Name | MW | RT (min) | $[M + H]^+$ calc'd | $[M + H]^+$ exp'tal | 220 nm | 254 nm |
| 1 | 5-(3-fluoro-5-hydroxy-3'-methoxy biphenyl-4-yl)-1,2,5-thiadiazolidin-3-one 1,1-dioxide | 352.3 | 6.87 | 353 | 353 | 92 | N/A |
| 2 | 5-(3,3'-difluoro-5-hydroxybiphenyl-4-yl)-1,2,5-thiadiazolidin-3-one 1,1-dioxide | 340.3 | 5.89 | 341 | 341 | 97 | 97 |
| 3 | 5-(3-fluoro-5-hydroxy-4'-methoxy biphenyl-4-yl)-1,2,5-thiadiazolidin-3-one 1,1-dioxide | 352.3 | 5.85 | 353 | 353 | 96 | 96 |
| 4 | 5-(3,3',5'-trifluoro-5-hydroxybiphenyl-4-yl)-1,2,5-thiadiazolidin-3-one 1,1-dioxide | 358.3 | 6.28 | 359 | 359 | 96 | 97 |
| 5 | 5-(2'-ethoxy-3-fluoro-5-hydroxybiphenyl-4-yl)-1,2,5-thiadiazolidin-3-one 1,1-dioxide | 366.4 | 6.45 | 367 | 367 | 96 | 99 |
| 6 | 5-(3-fluoro-5-hydroxy-2'-methylbiphenyl-4-yl)-1,2,5-thiadiazolidin-3-one 1,1-dioxide | 336.3 | 6.32 | 337 | 337 | 96 | 100 |
| 7 | 5-(2',3-difluoro-5-hydroxybiphenyl-4-yl)-1,2,5-thiadiazolidin-3-one 1,1-dioxide | 340.3 | 5.74 | 341 | 341 | 91 | 90 |
| 8 | 5-(3,4'-difluoro-5-hydroxybiphenyl-4-yl)-1,2,5-thiadiazolidin-3-one 1,1-dioxide | 340.3 | 6.36 | 341 | 341 | 98 | 98 |
| 9 | 5-(3-fluoro-5-hydroxy-3'-methylbiphenyl-4-yl)-1,2,5-thiadiazolidin-3-one 1,1-dioxide | 336.3 | 6.44 | 337 | 337 | 96 | 99 |
| 10 | 5-(3-fluoro-5-hydroxy-4'-methylbiphenyl-4-yl)-1,2,5-thiadiazolidin-3-one 1,1-dioxide | 336.3 | 6.46 | 337 | 337 | 96 | 99 |
| 11 | 5-[3'-({1-[(2-chlorobenzyl)sulfonyl]piperidin-4-yl} amino)-3-fluoro-5-hydroxybiphenyl-4-yl]-1,2,5-thiadiazolidin-3-one 1,1-dioxide | 609.1 | 6.19 | 609 | 609 | 97 | 97 |
| 12 | 5-(3'-{[1-(benzylsulfonyl)piperidin-4-yl]amino}-3-fluoro-5-hydroxybiphenyl-4- | 574.7 | 5.77 | 575 | 575 | 96 | 97 |

-continued

| Example No. | Name | MW | RT (min) | MS (ESI) [M + H]+ calc'd | MS (ESI) [M + H]+ exp'tal | Purity (%) 220 nm | Purity (%) 254 nm |
|---|---|---|---|---|---|---|---|
| | yl)-1,2,5-thiadiazolidin-3-one 1,1-dioxide | | | | | | |
| 13 | N-[4-(1,1-dioxido-4-oxo-1,2,5-thiadiazolidin-2-yl)-3-fluoro-5-hydroxyphenyl]benzamide | 365.3 | 4.87 | 366 | 366 | 98 | 99 |
| 14 | N-[4-(1,1-dioxido-4-oxo-1,2,5-thiadiazolidin-2-yl)-3-fluoro-5-hydroxyphenyl]-3,4-dimethoxybenzamide | 425.4 | 4.72 | 426 | 426 | 98 | 98 |
| 15 | N-[4-(1,1-dioxido-4-oxo-1,2,5-thiadiazolidin-2-yl)-3-fluoro-5-hydroxyphenyl]-4-methoxybenzamide | 395.4 | 5.06 | 396 | 396 | 99 | 99 |
| 16 | 4-tert-butyl-N-[4-(1,1-dioxido-4-oxo-1,2,5-thiadiazolidin-2-yl)-3-fluoro-5-hydroxyphenyl]benzamide | 421.5 | 6.59 | 422 | 422 | 97 | 97 |
| 17 | N-[4-(1,1-dioxido-4-oxo-1,2,5-thiadiazolidin-2-yl)-3-fluoro-5-hydroxyphenyl]benzene sulfonamide | 401.4 | 4.85 | 402 | 402 | 98 | 98 |
| 18 | N-[4-(1,1-dioxido-4-oxo-1,2,5-thiadiazolidin-2-yl)-3-fluoro-5-hydroxyphenyl]-4-methylbenzenesulfonamide | 415.4 | 5.96 | 416 | 416 | 92 | N/A |
| 19 | N-[4-(1,1-dioxido-4-oxo-1,2,5-thiadiazolidin-2-yl)-3-fluoro-5-hydroxyphenyl]-4-[5-(4-methylphenyl)-3-(trifluoromethyl)-1H-pyrazol-1-yl] benzenesulfonamide | 625.6 | 7.60 | 626 | 626 | 96 | 95 |
| 20 | N-[4-(1,1-dioxido-4-oxo-1,2,5-thiadiazolidin-2-yl)-3-fluoro-5-hydroxyphenyl]-4-fluorobenzenesulfonamide | 419.4 | 5.06 | 420 | 420 | 96 | 95 |
| 21 | N-[4-(1,1-dioxido-4-oxo-1,2,5-thiadiazolidin-2-yl)-3-fluoro-5-hydroxyphenyl]-2-fluorobenzenesulfonamide | 419.4 | 4.90 | 420 | 420 | 97 | 100 |
| 22 | N-[4-(1,1-dioxido-4-oxo-1,2,5-thiadiazolidin-2-yl)-3-fluoro-5-hydroxyphenyl]-3-methylbenzenesulfonamide | 415.4 | 5.56 | 416 | 416 | 90 | 91 |
| 23 | N-[4-(1,1-dioxido-4-oxo-1,2,5-thiadiazolidin-2-yl)-3-fluoro-5-hydroxyphenyl]-2-methylbenzenesulfonamide | 415.4 | 5.43 | 416 | 416 | 98 | 97 |
| 24 | 4-tert-butyl-N-[4-(1,1-dioxido-4-oxo-1,2,5-thiadiazolidin-2-yl)-3-fluoro-5-hydroxyphenyl]benzene sulfonamide | 457.5 | 6.35 | 458 | 458 | 97 | 98 |
| 25 | N-[4-(1,1-dioxido-4-oxo-1,2,5-thiadiazolidin-2-yl)-3-fluoro-5-hydroxyphenyl]-4-methoxybenzenesulfonamide | 431.4 | 4.71 | 432 | 432 | 99 | 100 |
| 26 | N-[4-(1,1-dioxido-4-oxo-1,2,5-thiadiazolidin-2-yl)-3-fluoro-5-hydroxyphenyl]-3,4-dimethoxybenzenesulfonamide | 461.5 | 4.63 | 462 | 462 | 98 | 98 |
| 27 | 1-(difluoromethyl)-N-[4-(1,1-dioxido-4-oxo-1,2,5-thiadiazolidin-2-yl)-3-fluoro-5-hydroxyphenyl]-5-methyl-1H-pyrazole-4-sulfonamide | 455.4 | 4.80 | 456 | 456 | 98 | 97 |
| 28 | N-[4-(1,1-dioxido-4-oxo-1,2,5-thiadiazolidin-2-yl)-3-fluoro-5-hydroxyphenyl]butane-1-sulfonamide | 381.4 | 4.76 | 382 | 382 | 96 | 96 |
| 29 | N-[4-(1,1-dioxido-4-oxo-1,2,5-thiadiazolidin-2-yl)-3-fluoro-5-hydroxyphenyl]-N'-phenylsulfuric diamide | 416.4 | | 417 | | | |

-continued

| Example No. | Name | MW | RT (min) | MS (ESI) [M + H]$^+$ calc'd | MS (ESI) [M + H]$^+$ exp'tal | Purity (%) 220 nm | Purity (%) 254 nm |
|---|---|---|---|---|---|---|---|
| 30 | N-{1-[(2-chlorobenzyl)sulfonyl]piperidin-4-yl}-N'-[4-(1,1-dioxido-4-oxo-1,2,5-thiadiazolidin-2-yl)-3-fluoro-5-hydroxyphenyl]sulfuric diamide | 612.1 | | 612 | | | |
| 31 | N'-[4-(1,1-dioxido-4-oxo-1,2,5-thiadiazolidin-2-yl)-3-fluoro-5-hydroxyphenyl]-N-methyl-N-phenylsulfuric diamide | 430.4 | 5.30 | 431 | 431 | 97 | 97 |
| 32 | N-cyclohexyl-N'-[4-(1,1-dioxido-4-oxo-1,2,5-thiadiazolidin-2-yl)-3-fluoro-5-hydroxyphenyl]-N-methylsulfuric diamide | 436.5 | 5.61 | 437 | 437 | 97 | 98 |
| 33 | N-(3-chlorophenyl)-N'-[4-(1,1-dioxido-4-oxo-1,2,5-thiadiazolidin-2-yl)-3-fluoro-5-hydroxyphenyl]-N-methylsulfuric diamide | 464.9 | | 465 | | | |
| 34 | N-(3,4-dimethoxybenzyl)-N'-[4-(1,1-dioxido-4-oxo-1,2,5-thiadiazolidin-2-yl)-3-fluoro-5-hydroxyphenyl]-N-phenylsulfuric diamide | 566.6 | | 567 | | | |
| 35 | 1-[4-(1,1-dioxido-4-oxo-1,2,5-thiadiazolidin-2-yl)-3-fluoro-5-hydroxyphenyl]-3-phenylurea | 380.4 | 5.07 | 381 | 381 | 94 | 94 |
| 36 | 1-[4-(1,1-dioxido-4-oxo-1,2,5-thiadiazolidin-2-yl)-3-fluoro-5-hydroxyphenyl]-3-(4-methylphenyl)urea | 394.4 | 5.45 | 395 | 395 | 95 | 95 |
| 37 | 1-[4-(1,1-dioxido-4-oxo-1,2,5-thiadiazolidin-2-yl)-3-fluoro-5-hydroxyphenyl]-3-(4-methoxyphenyl)urea | 410.4 | 4.96 | 41 | 411 | 95 | 95 |
| 38 | 1-[4-(1,1-dioxido-4-oxo-1,2,5-thiadiazolidin-2-yl)-3-fluoro-5-hydroxyphenyl]-3-[3-(trifluoromethyl)phenyl] urea | 448.4 | 6.18 | 449 | 449 | | |
| 39 | 1-[4-(1,1-dioxido-4-oxo-1,2,5-thiadiazolidin-2-yl)-3-fluoro-5-hydroxyphenyl]-3-(2-methylphenyl)urea | 394.4 | 5.36 | 395 | 395 | 93 | 93 |
| 40 | 1-[4-(1,1-dioxido-4-oxo-1,2,5-thiadiazolidin-2-yl)-3-fluoro-5-hydroxyphenyl]-3-(2-methoxyphenyl)urea | 410.4 | | 411 | | | |
| 41 | 1-[4-(1,1-dioxido-4-oxo-1,2,5-thiadiazolidin-2-yl)-3-fluoro-5-hydroxyphenyl]-3-[4-(trifluoromethyl)phenyl] urea | 448.4 | 6.26 | 449 | 449 | 91 | 90 |
| 42 | 1-[4-(1,1-dioxido-4-oxo-1,2,5-thiadiazolidin-2-yl)-3-fluoro-5-hydroxyphenyl]-3-(3-methylphenyl)urea | 394.4 | 5.62 | 395 | 395 | 91 | 91 |
| 43 | 1-[4-(1,1-dioxido-4-oxo-1,2,5-thiadiazolidin-2-yl)-3-fluoro-5-hydroxyphenyl]-3-(3-methoxyphenyl)urea | 410.4 | | 411 | | | |
| 44 | 1-[4-(1,1-dioxido-4-oxo-1,2,5-thiadiazolidin-2-yl)-3-fluoro-5-hydroxyphenyl]-3-pyridin-4-ylurea | 381.3 | | 382 | | | |
| 45 | 1-{1-[(2-chlorobenzyl)sulfonyl]piperidin-4-yl}-3-[4-(1,1-dioxido-4-oxo-1,2,5-thiadiazolidin-2-yl)-3-fluoro-5-hydroxyphenyl]urea | 576.0 | 5.69 | 576 | 576 | 90 | 92 |
| 46 | 1-(3-chlorophenyl)-3-[4-(1,1-dioxido-4-oxo-1,2,5-thiadiazolidin-2-yl)-3-fluoro-5-hydroxyphenyl]urea | 414.8 | 5.82 | 415 | 415 | 97 | 96 |
| 47 | 1-(4-chlorophenyl)-3-[4-(1,1-dioxido-4-oxo-1,2,5- | 414.8 | 5.75 | 415 | 415 | 97 | 98 |

-continued

| Example No. | Name | MW | RT (min) | MS (ESI) $[M + H]^+$ calc'd | $[M + H]^+$ exp'tal | Purity (%) 220 nm | 254 nm |
|---|---|---|---|---|---|---|---|
| | thiadiazolidin-2-yl)-3-fluoro-5-hydroxyphenyl]urea | | | | | | |
| 48 | 1-(2-chlorophenyl)-3-[4-(1,1-dioxido-4-oxo-1,2,5-thiadiazolidin-2-yl)-3-fluoro-5-hydroxyphenyl]urea | 414.8 | 5.63 | 415 | 415 | 97 | 98 |
| 49 | 1-(1H-benzimidazol-5-yl)-3-[4-(1,1-dioxido-4-oxo-1,2,5-thiadiazolidin-2-yl)-3-fluoro-5-hydroxyphenyl]urea | 420.4 | | 421 | | | |
| 50 | 1-(3-tert-butyl-1-methyl-1H-pyrazol-5-yl)-3-[4-(1,1-dioxido-4-oxo-1,2,5-thiadiazolidin-2-yl)-3-fluoro-5-hydroxyphenyl]urea | 440.5 | 4.53 | 441 | 441 | N/A | N/A |
| 51 | 1-{1-[(2-chlorophenyl)sulfonyl]piperidin-4-yl}-3-[4-(1,1-dioxido-4-oxo-1,2,5-thiadiazolidin-2-yl)-3-fluoro-5-hydroxyphenyl]urea | 562.0 | 5.60 | 562 | 562 | 95 | 96 |
| 52 | 1-[4-(1,1-dioxido-4-oxo-1,2,5-thiadiazolidin-2-yl)-3-fluoro-5-hydroxyphenyl]-3-pyridin-3-ylurea | 381.3 | | 382 | | | |
| 53 | 1-[4-(1,1-dioxido-4-oxo-1,2,5-thiadiazolidin-2-yl)-3-fluoro-5-hydroxyphenyl]-3-(4-fluorophenyl)urea | 398.4 | 5.20 | 399 | 399 | 94 | 93 |
| 54 | 1-[4-(1,1-dioxido-4-oxo-1,2,5-thiadiazolidin-2-yl)-3-fluoro-5-hydroxyphenyl]-3-(3-fluorophenyl)urea | 398.4 | 5.38 | 399 | 399 | 91 | 91 |
| 55 | 1-[4-(1,1-dioxido-4-oxo-1,2,5-thiadiazolidin-2-yl)-3-fluoro-5-hydroxyphenyl]-3-[2-(trifluoromethyl)phenyl] urea | 448.4 | 5.68 | 449 | 449 | 97 | 97 |
| 56 | 1-cyclohexyl-3-[4-(1,1-dioxido-4-oxo-1,2,5-thiadiazolidin-2-yl)-3-fluoro-5-hydroxyphenyl]urea | 386.4 | 5.15 | 387 | 387 | 97 | 97 |
| 57 | 1-[4-(1,1-dioxido-4-oxo-1,2,5-thiadiazolidin-2-yl)-3-fluoro-5-hydroxyphenyl]-3-(tetrahydrofuran-2-ylmethyl)urea | 388.4 | 3.89 | 389 | 389 | 97 | 97 |
| 58 | 1-[4-(1,1-dioxido-4-oxo-1,2,5-thiadiazolidin-2-yl)-3-fluoro-5-hydroxyphenyl]-3-(3-methoxypropyl)urea | 376.4 | 3.76 | 377 | 377 | 92 | 92 |
| 59 | 1-(3,4-dimethoxyphenyl)-3-[4-(1,1-dioxido-4-oxo-1,2,5-thiadiazolidin-2-yl)-3-fluoro-5-hydroxyphenyl]urea | 440.4 | 4.58 | 441 | 441 | 96 | 95 |
| 60 | 1-benzyl-3-[4-(1,1-dioxido-4-oxo-1,2,5-thiadiazolidin-2-yl)-3-fluoro-5-hydroxyphenyl]urea | 394.4 | 5.13 | 395 | 395 | 99 | 98 |
| 61 | 1-[4-(1,1-dioxido-4-oxo-1,2,5-thiadiazolidin-2-yl)-3-fluoro-5-hydroxyphenyl]-3-tricyclo[3.3.1.1$^{3,7}$]dec-1-ylurea | 438.5 | | 439 | | | |
| 62 | 1-[4-(1,1-dioxido-4-oxo-1,2,5-thiadiazolidin-2-yl)-3-fluoro-5-hydroxyphenyl]-3-(3-methylbutyl)urea | 374.4 | 5.11 | 375 | 375 | 96 | 97 |
| 63 | 1-[4-(1,1-dioxido-4-oxo-1,2,5-thiadiazolidin-2-yl)-3-fluoro-5-hydroxyphenyl]-3-(4-methoxybenzyl)urea | 424.4 | 4.91 | 425 | 425 | 95 | 96 |
| 64 | 1-[1-(2-chlorobenzyl)-1H-pyrazol-4-yl]-3-[4-(1,1-dioxido-4-oxo-1,2,5-thiadiazolidin-2-yl)-3-fluoro-5-hydroxyphenyl]urea | 494.9 | | 495 | | | |
| 65 | 1-[4-(1,1-dioxido-4-oxo-1,2,5-thiadiazolidin-2-yl)-3-fluoro-5- | 465.5 | 3.75 | 466 | 466 | 98 | 95 |

-continued

| Example No. | Name | MW | RT (min) | MS (ESI) [M + H]$^+$ calc'd | [M + H]$^+$ exp'tal | Purity (%) 220 nm | 254 nm |
|---|---|---|---|---|---|---|---|
| | hydroxyphenyl]-3-[4-(morpholin-4-yl)phenyl]urea | | | | | | |
| 66 | tert-butyl 4-[4-({[4-(1,1-dioxido-4-oxo-1,2,5-thiadiazolidin-2-yl)-3-fluoro-5-hydroxyphenyl]carbamoyl}amino)phenyl]piperazine-1-carboxylate | 564.6 | 5.05 | 565 | 565 | 96 | 96 |
| 67 | 1-[4-(1,1-dioxido-4-oxo-1,2,5-thiadiazolidin-2-yl)-3-fluoro-5-hydroxyphenyl]-3-[4-(piperazin-1-yl)phenyl]urea hydrocloride | 464.5 | 3.27 | 465 | 465 | 93 | 92 |
| 68 | 1-[4-(1,1-dioxido-4-oxo-1,2,5-thiadiazolidin-2-yl)-3-fluoro-5-hydroxyphenyl]-3-[4-methoxy-3-(trifluoromethyl)phenyl] urea | 478.4 | 5.96 | 479 | 479 | 99 | 67 |
| 69 | 1-[4-(1,1-dioxido-4-oxo-1,2,5-thiadiazolidin-2-yl)-3-fluoro-5-hydroxyphenyl]-3-[4-(methylsulfonyl)phenyl] urea | 458.4 | | 459 | | | |
| 70 | 1-[4-(1,1-dioxido-4-oxo-1,2,5-thiadiazolidin-2-yl)-3-fluoro-5-hydroxyphenyl]-3-[4-(propan-2-yl)phenyl]urea | 422.5 | 6.55 | 423 | 423 | 98 | 97 |
| 71 | 1-[4-(1,1-dioxido-4-oxo-1,2,5-thiadiazolidin-2-yl)-3-fluoro-5-hydroxyphenyl]-3-[4-(trifluoromethoxy)phenyl]urea | 464.4 | 6.37 | 465 | 465 | 97 | 98 |
| 72 | 1-[4-(1,1-dioxido-4-oxo-1,2,5-thiadiazolidin-2-yl)-3-fluoro-5-hydroxyphenyl]-3-(1-methylpiperidin-4-yl)urea | 401.4 | | 402 | | | |
| 73 | N-[4-(1,1-dioxido-4-oxo-1,2,5-thiadiazolidin-2-yl)-3-fluoro-5-hydroxyphenyl]-3,4-dihydroquinoline-1(2H)-carboxamide | 420.4 | | 421 | | | |
| 74 | N-[4-(1,1-dioxido-4-oxo-1,2,5-thiadiazolidin-2-yl)-3-fluoro-5-hydroxyphenyl]-3,4-dihydroisoquinoline-2(1H)-carboxamide | 420.4 | | 421 | | | |
| 75 | (3S)-N-[4-(1,1-dioxido-4-oxo-1,2,5-thiadiazolidin-2-yl)-3-fluoro-5-hydroxyphenyl]-3-(morpholin-4-ylmethyl)-3,4-dihydroisoquinoline-2(1H)-carboxamide | 519.6 | | 520 | | | |
| 76 | 3-[4-(1,1-dioxido-4-oxo-1,2,5-thiadiazolidin-2-yl)-3-fluoro-5-hydroxyphenyl]-1-methyl-1-phenylurea | 394.4 | | 395 | | | |
| 77 | 1-[4-(1,1-dioxido-4-oxo-1,2,5-thiadiazolidin-2-yl)-3-fluoro-5-hydroxyphenyl]-3-(1-methyl-1,2,3,4-tetrahydroquinolin-7-yl)urea | 449.5 | | 450 | | | |
| 78 | N-[4-(1,1-dioxido-4-oxo-1,2,5-thiadiazolidin-2-yl)-3-fluoro-5-hydroxyphenyl]pyridine-3-sulfonamide | 402.4 | | 403 | | | |
| 79 | 4-chloro-N-[4-(1,1-dioxido-4-oxo-1,2,5-thiadiazolidin-2-yl)-3-fluoro-5-hydroxyphenyl]benzene sulfonamide | 435.8 | | 436 | | | |
| 80 | methyl 2-{[4-(1,1-dioxido-4-oxo-1,2,5-thiadiazolidin-2-yl)-3-fluoro-5-hydroxyphenyl]sulfamoyl}benzoate | 459.4 | | 460 | | | |
| 81 | N-[4-(1,1-dioxido-4-oxo-1,2,5-thiadiazolidin-2-yl)-3-fluoro-5- | 419.4 | | 420 | | | |

-continued

| Example No. | Name | MW | RT (min) | MS (ESI) [M + H]+ calc'd | MS (ESI) [M + H]+ exp'tal | Purity (%) 220 nm | Purity (%) 254 nm |
|---|---|---|---|---|---|---|---|
| | hydroxyphenyl]-3-fluorobenzenesulfonamide | | | | | | |
| 82 | 3-chloro-N-[4-(1,1-dioxido-4-oxo-1,2,5-thiadiazolidin-2-yl)-3-fluoro-5-hydroxyphenyl]benzenesulfonamide | 435.8 | | 436 | | | |
| 83 | N-[4-(1,1-dioxido-4-oxo-1,2,5-thiadiazolidin-2-yl)-3-fluoro-5-hydroxyphenyl]-4-(trifluoromethyl)benzenesulfonamide | 469.4 | | 470 | | | |
| 84 | N-[4-(1,1-dioxido-4-oxo-1,2,5-thiadiazolidin-2-yl)-3-fluoro-5-hydroxyphenyl]-3-(trifluoromethyl)benzenesulfonamide | 469.4 | | 470 | | | |
| 85 | N-[4-(1,1-dioxido-4-oxo-1,2,5-thiadiazolidin-2-yl)-3-fluoro-5-hydroxyphenyl]-1-phenylmethanesulfonamide | 415.4 | | 416 | | | |
| 86 | N-[4-(1,1-dioxido-4-oxo-1,2,5-thiadiazolidin-2-yl)-3-fluoro-5-hydroxyphenyl]cyclopropane-sulfonamide | 365.4 | | 366 | | | |
| 87 | N-[4-(1,1-dioxido-4-oxo-1,2,5-thiadiazolidin-2-yl)-3-fluoro-5-hydroxyphenyl]propane-2-sulfonamide | 367.4 | | 368 | | | |
| 88 | 1-cyclopentyl-3-[4-(1,1-dioxido-4-oxo-1,2,5-thiadiazolidin-2-yl)-3-fluoro-5-hydroxyphenyl]urea | 372.4 | | 373 | | | |
| 89 | 1-[4-(1,1-dioxido-4-oxo-1,2,5-thiadiazolidin-2-yl)-3-fluoro-5-hydroxyphenyl]-3-(4-methylcyclohexyl)urea | 400.4 | | 401 | | | |
| 90 | 1-(4-tert-butylcyclohexyl)-3-[4-(1,1-dioxido-4-oxo-1,2,5-thiadiazolidin-2-yl)-3-fluoro-5-hydroxyphenyl]urea | 442.5 | | 443 | | | |
| 91 | 1-[4-(1,1-dioxido-4-oxo-1,2,5-thiadiazolidin-2-yl)-3-fluoro-5-hydroxyphenyl]-3-(trans-4-hydroxycyclohexyl)urea | 402.4 | | 403 | | | |
| 92 | 1-cycloheptyl-3-[4-(1,1-dioxido-4-oxo-1,2,5-thiadiazolidin-2-yl)-3-fluoro-5-hydroxyphenyl]urea | 400.4 | | 401 | | | |
| 93 | 1-[4-(1,1-dioxido-4-oxo-1,2,5-thiadiazolidin-2-yl)-3-fluoro-5-hydroxyphenyl]-3-(2-fluorophenyl)urea | 398.3 | 5.55 | 399 | 399 | 96 | 97 |
| 94 | 1-[4-(1,1-dioxido-4-oxo-1,2,5-thiadiazolidin-2-yl)-3-fluoro-5-hydroxyphenyl]-3-[3-(piperidin-1-yl)propyl]urea | 429.5 | | 430 | | | |
| 95 | 1-[4-(1,1-dioxido-4-oxo-1,2,5-thiadiazolidin-2-yl)-3-fluoro-5-hydroxyphenyl]-3-[3-(morpholin-4-yl)propyl]urea | 431.4 | | 432 | | | |
| 96 | N'-[4-(1,1-dioxido-4-oxo-1,2,5-thiadiazolidin-2-yl)-3-fluoro-5-hydroxyphenyl]-N-(3-fluorophenyl)-N-methylsulfuric diamide | 448.4 | | 449 | | | |
| 97 | N'-[4-(1,1-dioxido-4-oxo-1,2,5-thiadiazolidin-2-yl)-3-fluoro-5-hydroxyphenyl]-N-(4-fluorophenyl)-N-methylsulfuric diamide | 448.4 | | 449 | | | |

The Table below presents analytical data for Examples 98-112. These compounds were prepared using the procedures described above, with modifications known to one of skill in the art incorporated as needed.

| Example No. | Name | Structure | $^1$H NMR description/LCMS (ESI+) m/z $[MH]^+$ |
|---|---|---|---|
| 98 | tert-butyl 4-[[3-fluoro-5-hydroxy-4-(1,1,4-trioxo-1,2,5-thiadiazolidin-2-yl)phenyl]carbamoyl-amino]piperidine-1-carboxylate | 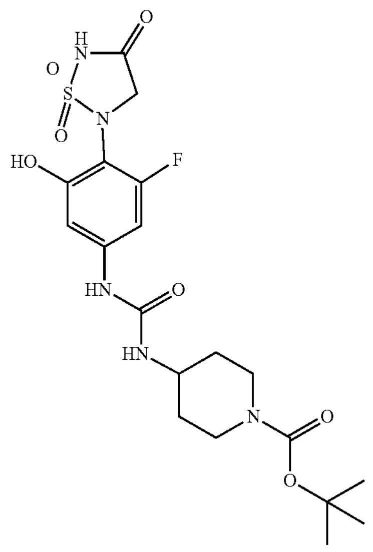 | $^1$H NMR (400 MHz, DMSO-$d_6$), δ: 9.24 (s, 1H), 8.54 (s, 1H), 6.83 (dd, J = 12.8, 2.4 Hz, 1H), 6.66 (d, J = 2.2 Hz, 1H), 6.26 (d, J = 7.6 Hz, 1H), 3.89 (s, 2H), 3.79 (d, J = 13.2 Hz, 2H), 3.62 (m, 1H), 2.90 (m, 2H), 1.78 (d, J = 12.5 Hz, 2H), 1.40 (s, 9H), 1.24 (q, J = 10.0 Hz, 2H). 1 proton in exchange/488 |
| 99 | 1-[3-fluoro-5-hydroxy-4-(1,1,4-trioxo-1,2,5-thiadiazolidin-2-yl)phenyl]-3-(4-piperidyl)urea | 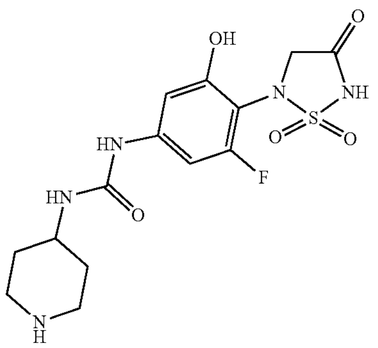 [SMILES: O=C1CN(c2c(O)cc(NC(=O)NC3CCNCC3)cc2F)S(=O)(=O)N1] | —/388 |
| 100 | 1-(2-azaspiro[4.5]decan-4-ylmethyl)-3-[3-fluoro-5-hydroxy-4-(1,1,4-trioxo-1,2,5-thiadiazolidin-2-yl)phenyl]urea | 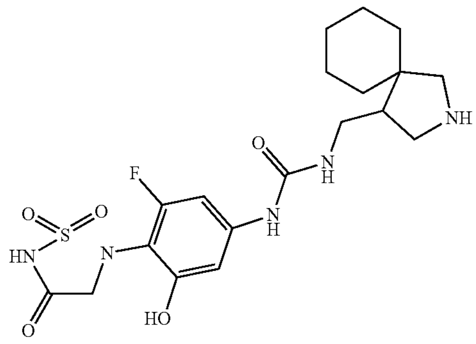 | $^1$H NMR (400 MHz, DMSO-$d_6$), δ: 9.92 (s, 1H), 9.12 (s, 3H), 6.89 (dd, J = 12.7, 2.4 Hz, 1H), 6.77 (s, 1H), 6.62 (t, J = 5.9 Hz, 1H), 4.17 (s, 2H), 3.28 (m, 3H), 2.93 (m, 3H), 2.04 (m, 1H), 1.43 (m, 10H)/456 |

-continued

| Example No. | Name | Structure | $^1$H NMR description/LCMS (ESI+) m/z [MH]$^+$ |
|---|---|---|---|
| 101 | tert-butyl 4-[[[3-fluoro-5-hydroxy-4-(1,1,4-trioxo-1,2,5-thiadiazolidin-2-yl)phenyl]carbamoyl-amino methyl]-2-azaspiro[4.5]decane-2-carboxylate | 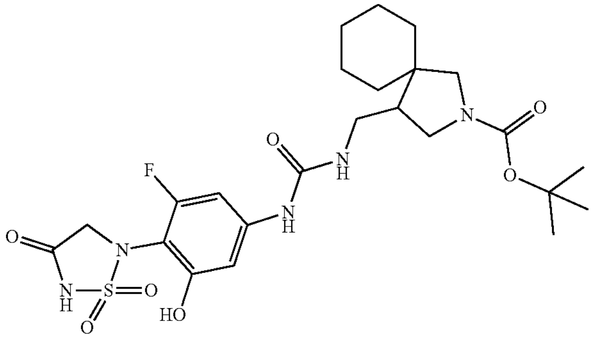 | $^1$H NMR (400 MHz, DMSO-$d_6$), δ: 9.26 (s, 1H), 8.65 (m, 1H), 6.83 (d, J = 12.7 Hz, 1H), 6.69 (m, 1H), 6.31 (m, 1H), 3.89 (s, 2H), 3.42 (m, 3H), 3.02 (m, 3H), 1.95 (m, 1H), 1.54 (m, 4H), 1.39 (s, 9H), 1.30 (m, 6H). 1 proton in exchange/557 |
| 102 | 1-[3-fluoro-5-hydroxy-4-(1,1,4-trioxo-1,2,5-thiadiazolidin-2-yl)phenyl]-3-[(2-isopentyl-2-azaspiro[4.5]decan-4-yl)methyl]urea | 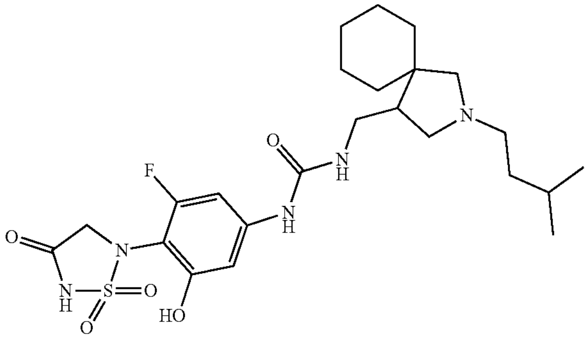 | $^1$H NMR (400 MHz, DMSO-$d_6$), δ: 9.58 (s, 1H), 9.47 (s, 1H), 8.77 (s, 1H), 6.88 (d, J = 12.8 Hz, 1H), 6.73 (s, 1H), 6.37 (m, 1H), 4.05 (s, 2H), 3.75 (m, 1H), 3.13 (m, 7H), 2.16 (m, 1H), 1.44 (m, 13H), 0.90 (d, J = 6.3 Hz, 6H)/526 |
| 103 | 1-[3-fluoro-5-hydroxy-4-(1,1,4-trioxo-1,2,5-thiadiazolidin-2-yl)phenyl]-3-[(1S)-2-hydroxy-1-phenyl-ethyl]urea | 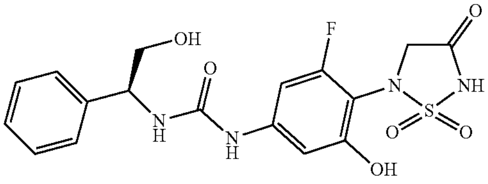 [SMILES: O=C1CN(c2c(O)cc(NC(=O)N[C@H](CO)c3ccccc3)cc2F)S(=O)(=O)N1] | $^1$H NMR (400 MHz, DMSO-$d_6$), δ: 8.79 (m, 2H), 7.32 (m, 5H), 6.81 (d, J = 12.7 Hz, 1H), 6.74 (d, J = 7.8 Hz, 1H), 6.65 (s, 1H), 4.96 (t, J = 5.3 Hz, 1H), 4.73 (q, J = 6.0 Hz, 1H), 3.89 (s, 2H), 3.61 (m, 2H). 1 proton in exchange/425 |
| 104 | 1-[3-fluoro-5-hydroxy-4-(1,1,4-trioxo-1,2,5-thiadiazolidin-2-yl)phenyl]-3-(3-piperidyl)urea | 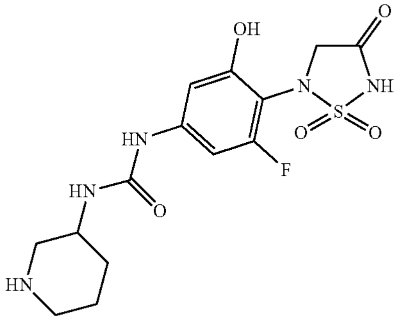 [SMILES: O=C1CN(c2c(O)cc(NC(=O)NC3CCCNC3)cc2F)S(=O)(=O)N1] | $^1$H NMR (400 MHz, DMSO-$d_6$), δ: 10.02 (s, 1H), 9.21 (s, 1H), 9.03 (m, 1H), 8.93 (m, 1H), 6.90 (dd, J = 12.6, 2.3 Hz, 1H), 6.78 (m, 2H), 4.20 (s, 2H), 3.80 (m, 1H), 3.19 (m, 2H), 2.75 (m, 2H), 1.86 (m, 2H), 1.69 (m, 1H), 1.46 (m, 1H)/388 |
| 105 | 1-[3-fluoro-5-hydroxy-4-(1,1,4-trioxo-1,2,5-thiadiazolidin-2-yl)phenyl]-3-(2-hydroxycyclohexyl)urea | 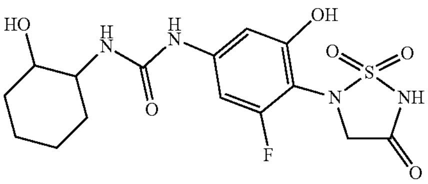 [SMILES: O=C1CN(c2c(O)cc(NC(=O)NC3CCCCC3O)cc2F)S(=O)(=O)N1] | $^1$H NMR (400 MHz, DMSO-$d_6$), δ: 9.13 (s, 1H), 8.78 (s, 1H), 6.83 (dd, J = 12.9, 2.3 Hz, 1H), 6.63 (d, J = 2.1 Hz, 1H), 6.09 (d, J = 8.3 Hz, 1H), 4.72 (d, J = 4.1 Hz, 1H), 3.89 (s, 2H), 3.71 (m, 1H), 3.53 (m, 1H), 1.52 (m, 6H), 1.27 (m, 2H). 1 proton in exchange/403 |

-continued

| Example No. | Name | Structure | $^1$H NMR description/LCMS (ESI+) m/z [MH]$^+$ |
|---|---|---|---|
| 106 | tert-butyl 3-[[3-fluoro-5-hydroxy-4-(1,1,4-trioxo-1,2,5-thiadiazolidin-2-yl)phenyl]carbamoyl-amino]piperidine-1-carboxylate | 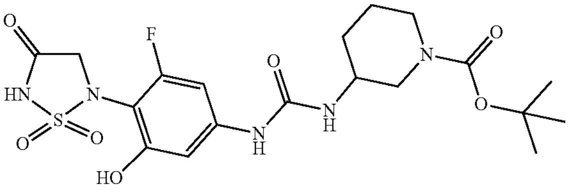 [SMILES: CC(C)(C)OC(=O)N1CCCC(NC(=O)Nc2cc(O)c(N3CC(=O)NS3(=O)=O)c(F)c2)C1] | $^1$H NMR (400 MHz, DMSO-$d_6$), δ: 9.22 (s, 1H), 8.54 (s, 1H), 6.81 (m, 1H), 6.66 (s, 1H), 6.23 (d, J = 7.5 Hz, 1H), 3.89 (s, 2H), 3.52 (s, 1H), 3.31 (s, 4H), 1.79 (m, 1H), 1.60 (m, 1H), 1.41 (s, 2H), 1.37 (s, 9H). 1 proton in exchange/488 |
| 107 | 1-[3-fluoro-5-hydroxy-4-(1,1,4-trioxo-1,2,5-thiadiazolidin-2-yl)phenyl]-3-[4-(hydroxymethyl)-cyclohexyl]urea | 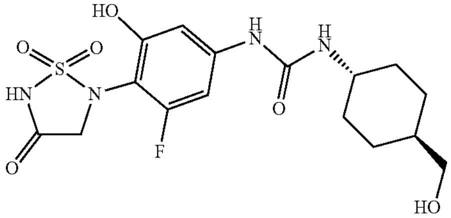 [SMILES: O=C1CN(c2c(O)cc(NC(=O)N[C@H]3CC[C@H](CO)CC3)cc2F)S(=O)(=O)N1] | $^1$H NMR (400 MHz, DMSO-$d_6$), δ: 10.19 (s, 1H), 8.52 (s, 1H), 6.85 (m, 1H), 6.76 (s, 1H), 6.06 (d, J = 7.8 Hz, 1H), 4.31 (s, 2H), 3.34 (s, 1H), 3.21 (d, J = 6.2 Hz, 2H), 1.87 (d, J = 12.2 Hz, 2H), 1.74 (d, J = 12.6 Hz, 2H), 1.29 (s, 1H), 1.11 (m, 2H), 0.94 (q, J = 12.7 Hz, 2H). 2 protons in exchange/417 |
| 108 | 1-[3-fluoro-5-hydroxy-4-(1,1,4-trioxo-1,2,5-thiadiazolidin-2-yl)phenyl]-3-[(1R,2S)-2-hydroxyindan-1-yl]urea | 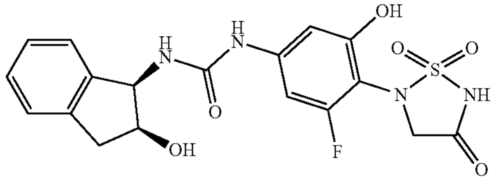 [SMILES: O=C1CN(c2c(O)cc(NC(=O)N[C@@H]3c4ccccc4C[C@@H]3O)cc2F)S(=O)(=O)N1] | $^1$H NMR (400 MHz, DMSO-$d_6$), δ: 9.28 (s, 1H), 8.98 (s, 1H), 7.19 (m, 4H), 6.89 (dd, J = 12.8, 2.3 Hz, 1H), 6.71 (m, 1H), 6.44 (d, J = 8.6 Hz, 1H), 5.28 (d, J = 4.3 Hz, 1H), 5.08 (dd, J = 8.5, 5.0 Hz, 1H), 4.44 (m, 1H), 3.91 (s, 2H), 3.06 (dd, J = 16.3, 4.8 Hz, 1H), 2.79 (d, J = 16.1 Hz, 1H). 1 proton in exchange/437 |
| 109 | 1-[(1S)-1-benzyl-2-hydroxy-ethyl]-3-[3-fluoro-5-hydroxy-4-(1,1,4-trioxo-1,2,5-thiadiazolidin-2-yl)phenyl]urea | 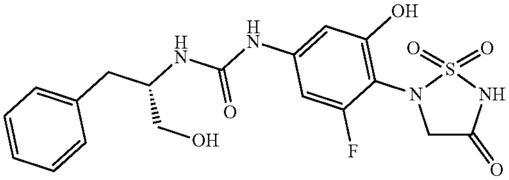 [SMILES: O=C1CN(c2c(O)cc(NC(=O)N[C@H](CO)Cc3ccccc3)cc2F)S(=O)(=O)N1] | $^1$H NMR (400 MHz, DMSO-$d_6$), δ: 10.30 (s, 1H), 8.73 (s, 1H), 7.24 (m, 5H), 6.81 (m, 2H), 6.14 (d, J = 8.3 Hz, 1H), 4.96 (s, 2H), 4.35 (s, 2H), 3.82 (m, 1H), 3.35 (m, 2H), 2.83 (dd, J = 13.5, 6.6 Hz, 1H), 2.70 (dd, J = 13.6, 7.3 Hz, 1H)/439 |
| 110 | 1-[3-fluoro-5-hydroxy-4-(1,1,4-trioxo-1,2,5-thiadiazolidin-2-yl)phenyl]-3-[(1S)-1-(hydroxymethyl)-3-methyl-butyl]urea | 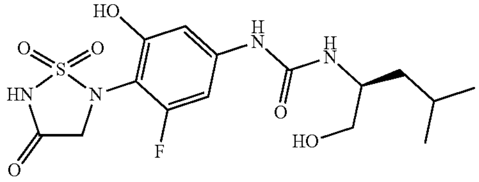 [SMILES: CC(C)C[C@@H](CO)NC(=O)Nc1cc(O)c(N2CC(=O)NS2(=O)=O)c(F)c1] | $^1$H NMR (400 MHz, DMSO-$d_6$) δ 9.16 (s, 1H), 8.57 (s, 1H), 6.81 (dd, J = 12.9, 2.4 Hz, 1H), 6.66 (s, 1H), 5.97 (d, J = 8.7 Hz, 1H), 4.72 (t, J = 5.4 Hz, 1H), 3.89 (s, 2H), 3.67 (m, 1H), 3.37 (m, 2H), 1.62 (m, 1H), 1.29 (m, 2H), 0.88 (m, 6H). 1 proton in exchange/405 |
| 111 | 1-[3-fluoro-5-hydroxy-4-(1,1,4-trioxo-1,2,5-thiadiazolidin-2-yl)phenyl]-3-[3-(hydroxymethyl)-1-bicyclo[1.1.1]pentanyl]urea | 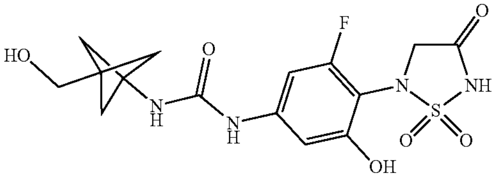 [SMILES: O=C1CN(c2c(O)cc(NC(=O)NC34CC(CO)(C3)C4)cc2F)S(=O)(=O)N1] | $^1$H NMR (400 MHz, DMSO-$d_6$), δ: 10.28 (s, 1H), 8.51 (s, 1H), 6.81 (m, 3H), 4.59 (m, 2H), 4.34 (s, 2H), 3.45 (s, 2H), 1.82 (s, 6H)/401 |

-continued

| Example No. | Name | Structure | $^1$H NMR description/LCMS (ESI+) m/z [MH]+ |
|---|---|---|---|
| 112 | 3-[[3-fluoro-5-hydroxy-4-(1,1,4-trioxo-1,2,5-thiadiazolidin-2-yl)phenyl]carbamoylamino]-N-isobutyl-bicyclo[1.1.1]pentane-1-carboxamide | 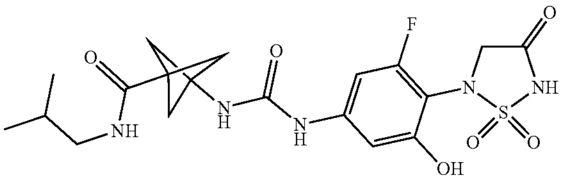 [SMILES: CC(C)CNC(=O)C12CC(NC(=O)Nc3cc(O)c(N4CC(=O)NS4(=O)=O)c(F)c3)(C1)C2] | $^1$H NMR (400 MHz, DMSO-$d_6$), δ: 10.27 (s, 1H), 8.55 (s, 1H), 7.69 (t, J = 6.0 Hz, 1H), 6.84 (m, 3H), 4.34 (s, 2H), 2.84 (t, J = 6.5 Hz, 2H), 2.13 (s, 6H), 1.69 (m, 1H), 0.81 (d, J = 6.7 Hz, 6H). 1 proton in exchange/470 |

Biological Assays

Example A. Primary Assay Used to Determine Potency of PTPN2 Enzymatic Activity Inhibition Compound activity was determined using GST-tagged PTPN2 protein (Cat #31592, ActiveMotif) (SEQ ID NO: 1) in an in vitro enzymatic reaction. The enzymatic reaction was carried out in assay buffer (50 mM HEPES Na salt pH 7.2-7.4, 2 mM EDTA, 100 mM NaCl, 52 ng/μL BSA, and 6 mM DTT). The compounds were dispensed on a 384 well Diamond Well Plate (Axigen, Cat #P-384-120SQ-C-S) using the Biomek FX liquid handling system at 100× solutions of compounds in DMSO. 2× PTPN2 (final concentration 0.004 ng/μL) was prepared in 1× Assay buffer and 25 μL of mixture per well was added into Reaction plate (Optiplate, black, Perkin Elmer, Cat #6007270). Add 25 μL of 1× buffer to Ctrl$^-$ (Substrate w/o PTPN2) wells followed by centrifugation at 100 g for 1 min. Next step the Compounds were added to Reaction plate using Biomek station via following steps: 3 ul of 100× compounds (in DMSO) were mixed with 27 μL of Assay Buffer, then 5 μL of this mixture was added to Reaction plate with 25 μL of PTPN2 Mix. Plates were centrifuged for 1 min at 100 g and incubated for another 10 minutes at room temperature. Finally, 20 μL of 2.5× Substrate (DiFUMP, Invitrogen™ Cat #D6567) mix was added into appropriate wells of Reaction plate to the final concentration of 2 μM, plate was centrifuged at 100 g for 1 min followed by incubation at RT for 60 min, and the Fluorescence Intensity was measured using a Microplate Reader (ClarioStar Plus, excitation 360 nm, emission 450 nm). The % inhibition was then used to calculate the $IC_{50}$ values. The $IC_{50}$ values are shown in Table A1, wherein "A" corresponds to $IC_{50}$<5.0 nm, "B" corresponds to 5.0 nm≤$IC_{50}$<10.0 nm, "C" corresponds to 10.0 nm≤$IC_{50}$<50.0 nm, "D" corresponds to 50.0 nm≤$IC_{50}$<100.0 nm, and "E" corresponds to 100.0 nm≤$IC_{50}$<500.0 nm, and "F" corresponds to 500.0 nm≤$IC_{50}$.

TABLE A1

| Primary PTPN2 inhibition | |
|---|---|
| Example No. | PTPN2 $IC_{50}$ (nM) |
| 1 | E |
| 2 | E |
| 3 | E |
| 4 | E |
| 5 | E |
| 6 | F |
| 7 | E |
| 8 | E |

TABLE A1-continued

| Primary PTPN2 inhibition | |
|---|---|
| Example No. | PTPN2 $IC_{50}$ (nM) |
| 9 | E |
| 10 | E |
| 11 | E |
| 12 | E |
| 13 | E |
| 14 | E |
| 15 | E |
| 16 | E |
| 17 | C |
| 18 | C |
| 19 | E |
| 20 | D |
| 21 | E |
| 22 | C |
| 23 | D |
| 24 | C |
| 25 | C |
| 26 | C |
| 27 | D |
| 28 | E |
| 31 | C |
| 32 | C |
| 35 | B |
| 36 | A |
| 37 | A |
| 39 | C |
| 41 | B |
| 42 | A |
| 45 | B |
| 46 | A |
| 47 | A |
| 48 | B |
| 51 | A |
| 53 | B |
| 54 | A |
| 55 | B |
| 56 | A |
| 57 | C |
| 58 | C |
| 59 | A |
| 60 | C |
| 62 | B |
| 63 | C |
| 65 | A |
| 66 | A |
| 67 | A |
| 68 | A |
| 70 | A |
| 71 | A |
| 93 | A |
| 98 | C |
| 99 | C |
| 100 | C |
| 101 | C |
| 102 | B |
| 103 | B |

TABLE A1-continued

| Primary PTPN2 inhibition | |
|---|---|
| Example No. | PTPN2 $IC_{50}$ (nM) |
| 104 | A |
| 105 | A |
| 106 | A |
| 107 | A |
| 108 | C |
| 109 | A |
| 110 | B |
| 111 | A |
| 112 | A |

Example B. Tumor Cells B16F10 Cellular Growth IFNγ-Induced Inhibition Assay

B16F10 mouse melanoma cells (ATCC Cat #CRL-6475) were seeded at a density of 500 cells per well in a 384-well clear bottom plate (Corning Cat #3712, Corning, N.Y.) in 40 µL total volume of DMEM+10% FBS (PanEco Cat #C420, Russia and Sigma Cat #F4135, St. Louis, Mo.). Cells were allowed to adhere overnight at 37° C., 5% $CO_2$. On the following day, 250× solutions of compounds in DMSO (Sigma Cat #D2650) were prepared into Cmpnds plate (Diamond Well Plate, Axigen, Cat #P-384-120SQ-C-S) (final concentration of 1×) and DMSO only controls were included. Dilution Plate (Diamond Well Plate (Axigen, Cat #P-384-120SQ-C-S) was prepared by adding 49 µL of culture medium per well: half of the plate with culture medium only, half with culture medium+IFNγ (5 ng/ml). A 1 µL aliquot of 250× compounds (Cmpnds plate) was added to 49 µL of culture medium (Dilution plate), then a 10 µL aliqut of the mixture was transferred to Reaction plate with 40 µL of cells followed by centrifugation at 240 g for 1 min. After 3 days of incubation, 10 µL of CellTiter-Glo (Promega) was added to the cells, plates were centrifuged at 240 g for 1 min, and luminescence signal was measured. For each compound, the percent growth inhibition at every compound dose level was calculated relative to the "DMSO/with IFNγ" control and used to determine the $IC_{50}$. The $IC_{50}$ values are shown in Table B1, wherein "A" corresponds to $IC_{50}$<5.0 µM, "B" corresponds to 5.0 µM≤$IC_{50}$<10.0 µM, "C" corresponds to 10.0 µM≤$IC_{50}$<50.0 µM, "D" corresponds to 50.0 µM≤$IC_{50}$<100.0 µM, and "E" corresponds to 100.0 µM≤$IC_{50}$; and the growth inhibition percentages are shown wherein "*" corresponds to percent growth inhibition <10.0%, "" corresponds to 10.0%≤percent growth inhibition <50.0%, "*" corresponds to 50.0%≤percent growth inhibition <75.0%, and "****" corresponds to 75.0%≤percent growth inhibition≤100.0%.

TABLE B1

| Growth Inhibition of B16F10 | | | | |
|---|---|---|---|---|
| Example No. | $IC_{50}$ no IFNγ (µM) | $IC_{50}$ + IFNγ (µM) | % Growth Inhibition at 100 µM no IFNγ | % Growth Inhibition at 100 µM + IFNγ |
| 1 | E | E | ** | ** |
| 2 | E | D | ** | *** |
| 3 | E | E | ** | ** |
| 4 | E | E | ** | ** |
| 5 | E | E | ** | *** |
| 7 | E | D | ** | *** |
| 8 | E | E | ** | ** |

TABLE B1-continued

| Growth Inhibition of B16F10 | | | | |
|---|---|---|---|---|
| Example No. | $IC_{50}$ no IFNγ (µM) | $IC_{50}$ + IFNγ (µM) | % Growth Inhibition at 100 µM no IFNγ | % Growth Inhibition at 100 µM + IFNγ |
| 11 | E | D | ** | *** |
| 12 | E | E | ** | ** |
| 13 | E | E | ** | ** |
| 14 | E | C | ** | *** |
| 15 | C | C | ** @ 40 µM | ** @ 40 µM |
| 16 | E | E | ** | ** |
| 17 | C | C | ** 40 µM | @ 40 µM |
| 18 | E | D | ** | *** |
| 19 | E | E | ** | ** |
| 20 | E | C | ** | *** |
| 21 | E | C | ** | *** |
| 22 | E | C | ** | *** |
| 23 | E | D | ** | *** |
| 24 | E | E | ** | *** |
| 25 | E | C | ** | *** |
| 26 | E | C | ** | *** |
| 27 | E | E | ** | ** |
| 28 | E | D | ** | *** |
| 35 | E | C | ** | **** |
| 36 | E | D | ** | *** |
| 37 | E | E | ** | ** |
| 39 | E | D | ** | *** |
| 41 | E | D | ** | *** |
| 42 | E | E | ** | ** |
| 45 | E | E | ** | ** |
| 46 | E | E | ** | ** |
| 47 | E | D | ** | *** |
| 48 | E | E | ** | ** |
| 51 | E | E | ** | ** |
| 53 | E | E | ** | ** |
| 54 | E | C | ** | *** |
| 55 | E | E | ** | ** |
| 56 | E | A | ** | **** |
| 57 | E | C | ** | *** |
| 58 | E | B | ** | **** |
| 59 | E | C | ** | *** |
| 62 | E | A | ** | **** |
| 63 | E | C | ** | **** |
| 98 | E | E | ** | ** |
| 99 | E | C | ** | *** |
| 100 | E | C | ** | *** |
| 101 | E | D | ** | *** |
| 102 | E | E | ** | ** |
| 103 | E | A | ** | **** |
| 104 | E | B | ** | **** |
| 105 | E | B | ** | **** |
| 106 | E | D | ** | *** |
| 107 | E | B | ** | *** |
| 108 | E | C | ** | *** |
| 109 | E | C | ** | *** |
| 110 | E | C | ** | *** |
| 111 | E | C | ** | **** |
| 112 | E | D | ** | ** |

Example C. Cytokines Release hPBMC Assay

Donor human PBMCs (120,000 cells/well in a 96 well flat-bottom plate (Greiner, #655061) were cultured in RPMI 1640 supplemented with 10% FBS at 37° ° C., 5% $CO_2$ in a humidified cell culture incubator for 0.5-1 hours. After the incubation, 10 µL/well 15× compound (or DMSO) in duplicates were added together with 20 µL/well of 7.5× anti-CD3 HIT3a activator (Invitrogen) to stimulate the PBMCs for 24 hours. Additionally, PBMCs with DMSO were incubated in the absence of anti-CD3 to evaluate its activation effect. After 24 hours of stimulation, supernatants were collected and IFNγ and IL-2 in supernatants were assessed using corresponding ELISA kits (Vector-Best, Russia). The IL-2 concentrations are shown in Tables C1 and C2, wherein "A" corresponds to IL-2<25.0 μg/mL, "B" corresponds to 25.0 μg/mL≤IL-2<50.0 μg/mL, "C" corresponds to 50.0 μg/mL≤IL-2<100.0 μg/mL, "D" corresponds to 100.0 μg/mL≤IL-2<250.0 μg/mL, and "E" corresponds to 250.0 μg/mL≤IL-2<500.0 μg/mL, and "F" corresponds to 500.0 μg/mL≤IL-2. The IFNγ concentrations are shown in Tables C1 and C2, wherein "A" corresponds to IFNγ<25.0 μg/mL, "B" corresponds to 25.0 μg/mL≤IFNγ<50.0 μg/mL, "C" corresponds to 50.0 μg/mL≤IFNγ<100.0 μg/mL, "D" corresponds to 100.0 μg/mL≤IFNγ<250.0 μg/mL, and "E" corresponds to 250.0 μg/mL≤IFNγ<500.0 μg/mL, and "F" corresponds to 500.0 μg/mL≤IFNγ.

TABLE C1

Cytokine data from the hPBMC function assays

| Example No. | IL-2 (pg/mL) no stimulation | IL-2 (pg/mL) anti-CD3 | IFNγ (pg/mL) no stimulation | IFNγ (pg/mL) anti-CD3 |
|---|---|---|---|---|
| Vehicle | 0.1 | B | 0.5 | E |
| 17 | | B | | F |
| 20 | | C | | F |
| 21 | | C | | E |
| 22 | | B | | F |
| 25 | | C | | F |
| 26 | | C | | F |
| 28 | | C | | E |
| 35 | | B | | E |

TABLE C2

Cytokine data from the hPBMC function assays

| Example No. | IL-2 (pg/mL) no stimulation | IL-2 (pg/mL) anti-CD3 | IFNγ (pg/mL) no stimulation | IFNγ (pg/mL) anti-CD3 |
|---|---|---|---|---|
| Vehicle | 2.5 | A | 0.5 | B |
| 15 | | B | | C |
| 36 | | B | | C |
| 39 | | B | | C |
| 41 | | A | | C |
| 42 | | B | | C |
| 46 | | B | | C |
| 47 | | A | | C |
| 54 | | A | | C |
| 55 | | A | | B |
| 56 | | B | | C |
| 57 | | B | | C |
| 58 | | A | | C |
| 59 | | B | | C |
| 63 | | B | | C |

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A compound of Formula (I-A-2-A):

(I-A-2-A)

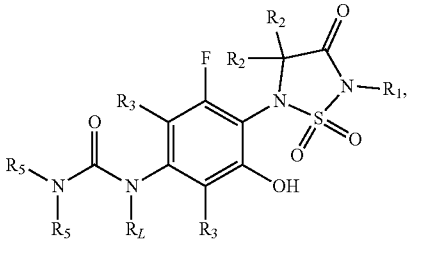

or a pharmaceutically acceptable salt, stereoisomer, solvate, or tautomer thereof, wherein:

$R_L$ is hydrogen;

$R_1$ is hydrogen;

each $R_2$ is hydrogen;

each $R_3$ is hydrogen;

each $R_5$ is independently selected from hydrogen, deuterium, $C_1$-$C_6$ alkyl, $C_2$-$C_6$ alkenyl, $C_2$-$C_6$ alkynyl, $C_3$-$C_{10}$ cycloalkyl, aryl, 3- to 10-membered heterocyclyl, and heteroaryl, wherein the alkyl, alkenyl, alkynyl, cycloalkyl, aryl, heterocyclyl, and heteroaryl are optionally substituted with one or more $R_6$;

or two $R_5$, together with the nitrogen atom to which they are attached, come together to form 3- to 10-membered heterocyclyl or heteroaryl, optionally substituted with one or more $R_6$;

each $R_6$ is independently selected from —C(O)$R_7$, —C(O)$NR_NR_7$, —C(O)O$R_7$, —$NR_NR_7$, —$NR_N$C(O)$R_7$, —OC(O)$R_7$, —S(O)$_2R_7$, halo, —CN, —$NO_2$, —OH, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, aryl, 3- to 10-membered heterocyclyl, and heteroaryl, wherein the alkyl, alkenyl, alkynyl, alkoxy, cycloalkyl, aryl, heterocyclyl, and heteroaryl are optionally substituted with one or more $R_7$;

each $R_7$ is independently selected from —C(O)O$R_8$, halo, —OH, —CN, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, aryl, 3- to 10-membered heterocyclyl, and heteroaryl, wherein the alkyl, alkenyl, alkynyl, alkoxy, cycloalkyl, aryl, heterocyclyl, and heteroaryl are optionally substituted with one or more $R_8$;

each $R_8$ is independently selected from —S(O)$R_9$, halo, —CN, —OH, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, aryl, 3- to 10-membered heterocyclyl, and heteroaryl, wherein the alkyl, alkenyl, alkynyl, alkoxy, cycloalkyl, aryl, heterocyclyl, and heteroaryl are optionally substituted with one or more $R_9$;

each $R_9$ is independently selected from halo, —CN, —OH, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, aryl, 3- to 10-membered heterocyclyl, and heteroaryl, wherein the alkyl, alkenyl, alkynyl, alkoxy, cycloalkyl, aryl, heterocyclyl, and heteroaryl are optionally substituted with one or more $R_{10}$;

each $R_{10}$ is independently selected from halo, —CN, —OH, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, $C_1$-$C_6$ haloalkoxy, $C_3$-$C_{10}$ cycloalkyl, aryl, 3- to 10-membered heterocyclyl, and heteroaryl, wherein the alkyl, alkenyl, alkynyl, alkoxy, cycloalkyl, aryl, heterocyclyl, and heteroaryl are optionally substituted with one or more $R_{11}$;

each $R_{11}$ is independently selected from halo, —CN, —OH, —$NO_2$, $C_1$-$C_6$ alkyl, $C_2$-$C_6$ alkenyl, $C_2$-$C_6$ alkynyl, $C_1$-$C_6$ haloalkyl, $C_1$-$C_6$ alkoxy, and $C_1$-$C_6$ haloalkoxy;

each $R_N$ is independently selected from hydrogen, deuterium, $C_1$-$C_6$ alkyl, $C_2$-$C_6$ alkenyl, and $C_2$-$C_6$ alkynyl.

2. A compound selected from:

| Example No. | Name |
|---|---|
| 35 | 1-[4-(1,1-dioxido-4-oxo-1,2,5-thiadiazolidin-2-yl)-3-fluoro-5-hydroxyphenyl]-3-phenylurea; |
| 36 | 1-[4-(1,1-dioxido-4-oxo-1,2,5-thiadiazolidin-2-yl)-3-fluoro-5-hydroxyphenyl]-3-(4-methylphenyl)urea; |
| 37 | 1-[4-(1,1-dioxido-4-oxo-1,2,5-thiadiazolidin-2-yl)-3-fluoro-5-hydroxyphenyl]-3-(4-methoxyphenyl)urea; |
| 38 | 1-[4-(1,1-dioxido-4-oxo-1,2,5-thiadiazolidin-2-yl)-3-fluoro-5-hydroxyphenyl]-3-[3-(trifluoromethyl)phenyl]urea; |
| 39 | 1-[4-(1,1-dioxido-4-oxo-1,2,5-thiadiazolidin-2-yl)-3-fluoro-5-hydroxyphenyl]-3-(2-methylphenyl)urea; |
| 40 | 1-[4-(1,1-dioxido-4-oxo-1,2,5-thiadiazolidin-2-yl)-3-fluoro-5-hydroxyphenyl]-3-(2-methoxyphenyl)urea; |
| 41 | 1-[4-(1,1-dioxido-4-oxo-1,2,5-thiadiazolidin-2-yl)-3-fluoro-5-hydroxyphenyl]-3-[4-(trifluoromethyl)phenyl]urea; |
| 42 | 1-[4-(1,1-dioxido-4-oxo-1,2,5-thiadiazolidin-2-yl)-3-fluoro-5-hydroxyphenyl]-3-(3-methylphenyl)urea; |
| 43 | 1-[4-(1,1-dioxido-4-oxo-1,2,5-thiadiazolidin-2-yl)-3-fluoro-5-hydroxyphenyl]-3-(3-methoxyphenyl)urea; |
| 44 | 1-[4-(1,1-dioxido-4-oxo-1,2,5-thiadiazolidin-2-yl)-3-fluoro-5-hydroxyphenyl]-3-pyridin-4-ylurea; |
| 45 | 1-{1-[(2-chlorobenzyl)sulfonyl]piperidin-4-yl}-3-[4-(1,1-dioxido-4-oxo-1,2,5-thiadiazolidin-2-yl)-3-fluoro-5-hydroxyphenyl]urea; |
| 46 | 1-(3-chlorophenyl)-3-[4-(1,1-dioxido-4-oxo-1,2,5-thiadiazolidin-2-yl)-3-fluoro-5-hydroxyphenyl]urea; |
| 47 | 1-(4-chlorophenyl)-3-[4-(1,1-dioxido-4-oxo-1,2,5-thiadiazolidin-2-yl)-3-fluoro-5-hydroxyphenyl]urea; |
| 48 | 1-(2-chlorophenyl)-3-[4-(1,1-dioxido-4-oxo-1,2,5-thiadiazolidin-2-yl)-3-fluoro-5-hydroxyphenyl]urea; |
| 49 | 1-(1H-benzimidazol-5-yl)-3-[4-(1,1-dioxido-4-oxo-1,2,5-thiadiazolidin-2-yl)-3-fluoro-5-hydroxyphenyl]urea; |
| 50 | 1-(3-tert-butyl-1-methyl-1H-pyrazol-5-yl)-3-[4-(1,1-dioxido-4-oxo-1,2,5-thiadiazolidin-2-yl)-3-fluoro-5-hydroxyphenyl]urea; |
| 51 | 1-{1-[(2-chlorophenyl)sulfonyl]piperidin-4-yl}-3-[4-(1,1-dioxido-4-oxo-1,2,5-thiadiazolidin-2-yl)-3-fluoro-5-hydroxyphenyl]urea; |
| 52 | 1-[4-(1,1-dioxido-4-oxo-1,2,5-thiadiazolidin-2-yl)-3-fluoro-5-hydroxyphenyl]-3-pyridin-3-ylurea; |
| 53 | 1-[4-(1,1-dioxido-4-oxo-1,2,5-thiadiazolidin-2-yl)-3-fluoro-5-hydroxyphenyl]-3-(4-fluorophenyl)urea; |
| 54 | 1-[4-(1,1-dioxido-4-oxo-1,2,5-thiadiazolidin-2-yl)-3-fluoro-5-hydroxyphenyl]-3-(3-fluorophenyl)urea; |
| 55 | 1-[4-(1,1-dioxido-4-oxo-1,2,5-thiadiazolidin-2-yl)-3-fluoro-5-hydroxyphenyl]-3-[2-(trifluoromethyl)phenyl]urea; |
| 56 | 1-cyclohexyl-3-[4-(1,1-dioxido-4-oxo-1,2,5-thiadiazolidin-2-yl)-3-fluoro-5-hydroxyphenyl]urea; |
| 57 | 1-[4-(1,1-dioxido-4-oxo-1,2,5-thiadiazolidin-2-yl)-3-fluoro-5-hydroxyphenyl]-3-(tetrahydrofuran-2-ylmethyl)urea; |
| 58 | 1-[4-(1,1-dioxido-4-oxo-1,2,5-thiadiazolidin-2-yl)-3-fluoro-5-hydroxyphenyl]-3-(3-methoxypropyl)urea; |

-continued

| Example No. | Name |
|---|---|
| 59 | 1-(3,4-dimethoxyphenyl)-3-[4-(1,1-dioxido-4-oxo-1,2,5-thiadiazolidin-2-yl)-3-fluoro-5-hydroxyphenyl]urea; |
| 60 | 1-benzyl-3-[4-(1,1-dioxido-4-oxo-1,2,5-thiadiazolidin-2-yl)-3-fluoro-5-hydroxyphenyl]urea; |
| 61 | 1-[4-(1,1-dioxido-4-oxo-1,2,5-thiadiazolidin-2-yl)-3-fluoro-5-hydroxyphenyl]-3-tricyclo[3.3.1.13,7]dec-1-ylurea; |
| 62 | 1-[4-(1,1-dioxido-4-oxo-1,2,5-thiadiazolidin-2-yl)-3-fluoro-5-hydroxyphenyl]-3-(3-methylbutyl)urea; |
| 63 | 1-[4-(1,1-dioxido-4-oxo-1,2,5-thiadiazolidin-2-yl)-3-fluoro-5-hydroxyphenyl]-3-(4-methoxybenzyl)urea; |
| 64 | 1-[1-(2-chlorobenzyl)-1H-pyrazol-4-yl]-3-[4-(1,1-dioxido-4-oxo-1,2,5-thiadiazolidin-2-yl)-3-fluoro-5-hydroxyphenyl]urea; |
| 65 | 1-[4-(1,1-dioxido-4-oxo-1,2,5-thiadiazolidin-2-yl)-3-fluoro-5-hydroxyphenyl]-3-[4-(morpholin-4-yl)phenyl]urea; |
| 66 | tert-butyl 4-[4-({[4-(1,1-dioxido-4-oxo-1,2,5-thiadiazolidin-2-yl)-3-fluoro-5-hydroxyphenyl]carbamoyl}amino)phenyl]piperazine-1-carboxylate; |
| 67 | 1-[4-(1,1-dioxido-4-oxo-1,2,5-thiadiazolidin-2-yl)-3-fluoro-5-hydroxyphenyl]-3-[4-(piperazin-1-yl)phenyl]urea hydrochloride; |
| 68 | 1-[4-(1,1-dioxido-4-oxo-1,2,5-thiadiazolidin-2-yl)-3-fluoro-5-hydroxyphenyl]-3-[4-methoxy-3-(trifluoromethyl)phenyl]urea; |
| 69 | 1-[4-(1,1-dioxido-4-oxo-1,2,5-thiadiazolidin-2-yl)-3-fluoro-5-hydroxyphenyl]-3-[4-(methylsulfonyl)phenyl]urea; |
| 70 | 1-[4-(1,1-dioxido-4-oxo-1,2,5-thiadiazolidin-2-yl)-3-fluoro-5-hydroxyphenyl]-3-[4-(propan-2-yl)phenyl]urea; |
| 71 | 1-[4-(1,1-dioxido-4-oxo-1,2,5-thiadiazolidin-2-yl)-3-fluoro-5-hydroxyphenyl]-3-[4-(trifluoromethoxy)phenyl]urea; |
| 72 | 1-[4-(1,1-dioxido-4-oxo-1,2,5-thiadiazolidin-2-yl)-3-fluoro-5-hydroxyphenyl]-3-(1-methylpiperidin-4-yl)urea; |
| 73 | N-[4-(1,1-dioxido-4-oxo-1,2,5-thiadiazolidin-2-yl)-3-fluoro-5-hydroxyphenyl]-3,4-dihydroquinoline-1(2H)-carboxamide; |
| 74 | N-[4-(1,1-dioxido-4-oxo-1,2,5-thiadiazolidin-2-yl)-3-fluoro-5-hydroxyphenyl]-3,4-dihydroisoquinoline-2(1H)-carboxamide; |
| 75 | (3S)-N-[4-(1,1-dioxido-4-oxo-1,2,5-thiadiazolidin-2-yl)-3-fluoro-5-hydroxyphenyl]-3-(morpholin-4-ylmethyl)-3,4-dihydroisoquinoline-2(1H)-carboxamide; |
| 76 | 3-[4-(1,1-dioxido-4-oxo-1,2,5-thiadiazolidin-2-yl)-3-fluoro-5-hydroxyphenyl]-1-methyl-1-phenylurea; |
| 77 | 1-[4-(1,1-dioxido-4-oxo-1,2,5-thiadiazolidin-2-yl)-3-fluoro-5-hydroxyphenyl]-3-(1-methyl-1,2,3,4-tetrahydroquinolin-7-yl)urea; |
| 88 | 1-cyclopentyl-3-[4-(1,1-dioxido-4-oxo-1,2,5-thiadiazolidin-2-yl)-3-fluoro-5-hydroxyphenyl]urea; |
| 89 | 1-[4-(1,1-dioxido-4-oxo-1,2,5-thiadiazolidin-2-yl)-3-fluoro-5-hydroxyphenyl]-3-(4-methylcyclohexyl)urea; |
| 90 | 1-(4-tert-butylcyclohexyl)-3-[4-(1,1-dioxido-4-oxo-1,2,5-thiadiazolidin-2-yl)-3-fluoro-5-hydroxyphenyl]urea; |
| 91 | 1-[4-(1,1-dioxido-4-oxo-1,2,5-thiadiazolidin-2-yl)-3-fluoro-5-hydroxyphenyl]-3-(trans-4-hydroxycyclohexyl)urea; |
| 92 | 1-cycloheptyl-3-[4-(1,1-dioxido-4-oxo-1,2,5-thiadiazolidin-2-yl)-3-fluoro-5-hydroxyphenyl]urea; |
| 93 | 1-[4-(1,1-dioxido-4-oxo-1,2,5-thiadiazolidin-2-yl)-3-fluoro-5-hydroxyphenyl]-3-(2-fluorophenyl)urea; |
| 94 | 1-[4-(1,1-dioxido-4-oxo-1,2,5-thiadiazolidin-2-yl)-3-fluoro-5-hydroxyphenyl]-3-[3-(piperidin-1-yl)propyl]urea; |
| 95 | 1-[4-(1,1-dioxido-4-oxo-1,2,5-thiadiazolidin-2-yl)-3-fluoro-5-hydroxyphenyl]-3-[3-(morpholin-4-yl)propyl]urea; |
| 98 | tert-butyl 4-[3-fluoro-5-hydroxy-4-(1,1,4-trioxo-1,2,5-thiadiazolidin-2-yl)phenyl]carbamoyl-amino]piperidine-1-carboxylate; |
| 99 | 1-[3-fluoro-5-hydroxy-4-(1,1,4-trioxo-1,2,5-thiadiazolidin-2-yl)phenyl]-3-(4-piperidyl)urea; |
| 100 | 1-(2-azaspiro[4.5]decan-4-ylmethyl)-3-[3-fluoro-5-hydroxy-4-(1,1,4-trioxo-1,2,5-thiadiazolidin-2-yl)phenyl]urea; |
| 101 | tert-butyl 4-[3-fluoro-5-hydroxy-4-(1,1,4-trioxo-1,2,5-thiadiazolidin-2-yl)phenyl]carbamoyl-amino]methyl]-2-azaspiro[4.5]decane-2-carboxylate; |
| 102 | 1-[3-fluoro-5-hydroxy-4-(1,1,4-trioxo-1,2,5-thiadiazolidin-2-yl)phenyl]-3-[(2-isopentyl-2-azaspiro[4.5]decan-4-yl)methyl]urea; |
| 103 | 1-[3-fluoro-5-hydroxy-4-(1,1,4-trioxo-1,2,5-thiadiazolidin-2-yl)phenyl]-3-[(1S)-2-hydroxy-1-phenylethyl]urea; |
| 104 | 1-[3-fluoro-5-hydroxy-4-(1,1,4-trioxo-1,2,5-thiadiazolidin-2-yl)phenyl]-3-(3-piperidyl)urea; |
| 105 | 1-[3-fluoro-5-hydroxy-4-(1,1,4-trioxo-1,2,5-thiadiazolidin-2-yl)phenyl]-3-(2-hydroxycyclohexyl)urea; |
| 106 | tert-butyl 3-[3-fluoro-5-hydroxy-4-(1,1,4-trioxo-1,2,5-thiadiazolidin-2-yl)phenyl]carbamoylamino]piperidine-1-carboxylate; |
| 107 | 1-[3-fluoro-5-hydroxy-4-(1,1,4-trioxo-1,2,5-thiadiazolidin-2-yl)phenyl]-3-[4-(hydroxymethyl)-cyclohexyl]urea; |
| 108 | 1-[3-fluoro-5-hydroxy-4-(1,1,4-trioxo-1,2,5-thiadiazolidin-2-yl)phenyl]-3-[(1R,2S)-2-hydroxyindan-1-yl]urea; |

-continued

| Example No. | Name |
|---|---|
| 109 | 1-[(1S)-1-benzyl-2-hydroxy-ethyl]-3-[3-fluoro-5-hydroxy-4-(1,1,4-trioxo-1,2,5-thiadiazolidin-2-yl)phenyl]urea; |
| 110 | 1-[3-fluoro-5-hydroxy-4-(1,1,4-trioxo-1,2,5-thiadiazolidin-2-yl)phenyl]-3-[(1S)-1-(hydroxymethyl)-3-methyl-butyl]urea; |
| 111 | 1-[3-fluoro-5-hydroxy-4-(1,1,4-trioxo-1,2,5-thiadiazolidin-2-yl)phenyl]-3-[3-(hydroxymethyl)-1-bicyclo[1.1.1]pentanyl]urea; |
| 112 | 3-[[3-fluoro-5-hydroxy-4-(1,1,4-trioxo-1,2,5-thiadiazolidin-2-yl)phenyl]carbamoylamino]-N-isobutyl-bicyclo[1.1.1]pentane-1-carboxamide |

or a pharmaceutically acceptable salt, stereoisomer, solvate, or tautomer thereof.

3. A pharmaceutical composition comprising a compound of claim 1 or pharmaceutically acceptable salt, solvate, hydrate, stereoisomer, or tautomer thereof, and a pharmaceutically acceptable carrier.

4. The pharmaceutical composition of claim 3, further comprising an additional pharmaceutically active agent.

5. A method of inhibiting a protein tyrosine phosphatase enzyme, comprising administering to a subject in need of a treatment for cancer a compound of claim 1 or a pharmaceutical composition of claim 3.

6. A method of treating a disease or disorder associated with the inhibition of protein tyrosine phosphatase enzyme, the method comprising administering to a subject in need of a treatment for cancer a compound of claim 1 or a pharmaceutical composition of claim 3.

7. A method of treating cancer, comprising administering to a subject in need of a treatment for cancer a compound of claim 1 or a pharmaceutical composition of claim 3.

8. The method of claim 7, wherein the cancer is selected from bladder cancer, bone cancer, brain cancer, breast cancer, cardiac cancer, cervical cancer, colon cancer, colorectal cancer, esophageal cancer, fibrosarcoma, gastric cancer, gastrointestinal cancer, head, spine and neck cancer, Kaposi's sarcoma, kidney cancer, leukemia, liver cancer, lymphoma, melanoma, multiple myeloma, pancreatic cancer, penile cancer, testicular germ cell cancer, thymoma carcinoma, thymic carcinoma, lung cancer, ovarian cancer, prostate cancer, marginal zone lymphoma (MZL), follicular lymphoma (FL), diffuse large B-cell lymphoma (DLBCL), and chronic lymphocytic leukemia/small lymphocytic lymphoma (CLL/SLL).

9. The method of claim 7, wherein the cancer is melanoma.

10. A method of treating a metabolic disease, comprising administering to a subject in need of a treatment for metabolic disease a compound of claim 1 or a pharmaceutical composition of claim 3.

11. The method of claim 10, wherein the metabolic disease is selected from non-alcoholic steatohepatitis (NASH), non-alcoholic fatty liver disease (NAFLD), liver fibrosis, obesity, heart disease, atherosclerosis, arthritis, cystinosis, diabetes, metabolic syndrome, phenylketonuria, proliferative retinopathy, or Kearns-Sayre disease.

12. The method of claim 11, wherein the diabetes is Type I diabetes.

13. The method of claim 11, wherein the diabetes is Type II diabetes.

14. The method of claim 11, wherein the diabetes is gestational diabetes.

15. The method of claim 5, wherein the protein tyrosine phosphatase enzyme is protein tyrosine phosphatase non-receptor type 1 (PTPN1), or protein tyrosine phosphatase non-receptor type 2 (PTPN2).

* * * * *